(12) United States Patent
Brown et al.

(10) Patent No.: US 10,150,752 B2
(45) Date of Patent: Dec. 11, 2018

(54) SUBSTITUTED TRIAZOLE DERIVATIVES AS OXYTOCIN ANTAGONISTS

(71) Applicant: Ixchelsis Limited, Sandwich, Kent (GB)

(72) Inventors: Alan Daniel Brown, Sandwich (GB); Andrew Antony Calabrese, Cockeysville, MD (US); David Ellis, Sandwich (GB)

(73) Assignee: Ixchelsis Limited, Sandwich, Kent (GB)

( * ) Notice: Subject to any disclaimer, the term of this patent is extended or adjusted under 35 U.S.C. 154(b) by 0 days.

(21) Appl. No.: 15/195,480

(22) Filed: Jun. 28, 2016

(65) Prior Publication Data

US 2017/0114040 A1 Apr. 27, 2017

Related U.S. Application Data

(60) Continuation of application No. 14/691,319, filed on Apr. 20, 2015, now Pat. No. 9,394,278, which is a continuation of application No. 13/478,384, filed on May 23, 2012, now Pat. No. 9,023,872, which is a division of application No. 12/466,785, filed on May 15, 2009, now Pat. No. 8,207,198, which is a division of application No. 11/335,940, filed on Jan. 20, 2006, now Pat. No. 7,557,131.

(60) Provisional application No. 60/649,892, filed on Feb. 2, 2005.

(30) Foreign Application Priority Data

Jan. 20, 2005 (GB) .................................. 0501190.3

(51) Int. Cl.
*C07D 401/14* (2006.01)

(52) U.S. Cl.
CPC .................................. *C07D 401/14* (2013.01)

(58) Field of Classification Search
CPC .................................................. C07D 401/14
USPC .......................................... 546/193; 514/318
See application file for complete search history.

(56) References Cited

U.S. PATENT DOCUMENTS

| | | | |
|---|---|---|---|
| 5,463,071 | A | 10/1995 | Himmelsbach et al. |
| 6,407,094 | B1 | 6/2002 | Adam et al. |
| 7,514,437 | B2 | 4/2009 | Borthwick et al. |
| 7,557,131 | B2 | 7/2009 | Brown et al. |
| 8,207,198 | B2 | 6/2012 | Brown et al. |
| 9,023,872 | B2 | 5/2015 | Brown et al. |
| 9,394,278 | B2 | 7/2016 | Brown et al. |
| 2004/0167188 | A1 | 8/2004 | Xin et al. |
| 2004/0214818 | A1 | 10/2004 | Tobe et al. |
| 2004/0214870 | A1 | 10/2004 | Xin et al. |

FOREIGN PATENT DOCUMENTS

| | | |
|---|---|---|
| AU | 5398494 | 1/1993 |
| DE | 4124942 | 1/1993 |
| EP | 0138464 | 9/1984 |
| EP | 0396282 | 4/1990 |
| EP | 0608858 | 8/1994 |
| EP | 1206935 | 7/2000 |
| EP | 1293503 | 5/2001 |
| WO | WO 97/36585 | 4/1997 |
| WO | WO 97/36876 | 4/1997 |
| WO | WO 97/36881 | 10/1997 |
| WO | WO 97/36897 | 10/1997 |
| WO | WO 98/28980 | 7/1998 |
| WO | WO 99/30697 | 6/1999 |
| WO | WO 01/07032 | 2/2001 |
| WO | WO 01/36395 | 5/2001 |
| WO | WO 01/76582 | 10/2001 |
| WO | WO 01/87855 A1 | 11/2001 |
| WO | WO 03/089412 | 10/2003 |
| WO | WO 03/093242 | 11/2003 |
| WO | WO 04/037809 | 5/2004 |
| WO | WO 05/028452 | 3/2005 |
| WO | WO 05/063754 | 7/2005 |
| WO | WO 05/082866 | 9/2005 |
| WO | WO 05/105779 | 11/2005 |

OTHER PUBLICATIONS

Akerlund, "Vascularization of human endometrium. Uterine blood flow in healthy condition and in primary dysmenorrhea," Sep. 1994 Annals New York Academy of Sciences, 734:47-46.
Arletti et al., "Influence of Oxytocin on Feeding Behavior in the Rat," 1989 Peptides, vol. 10: 89-93.
Georgia Search Report dated Dec. 26, 2008, Patent Application AP 2006 01085.
Gimpl et al., "The Oxytocin Receptor System: Structure, Function, and Regulation" Apr. 2001 Physiological Reviews, 81(2): 629-683.
Jain et al., "Polymorphism in Pharmacy" 1986 Indian Drugs, 23(6): 315-329.

(Continued)

*Primary Examiner* — Patricia L Morris
(74) *Attorney, Agent, or Firm* — Mueting, Raasch & Gabhardt, P.A.

(57) ABSTRACT

The present invention relates to substituted triazoles of formula (I), uses thereof, processes for the preparation thereof and compositions containing said compounds. These inhibitors have utility in a variety of therapeutic areas including sexual dysfunction.

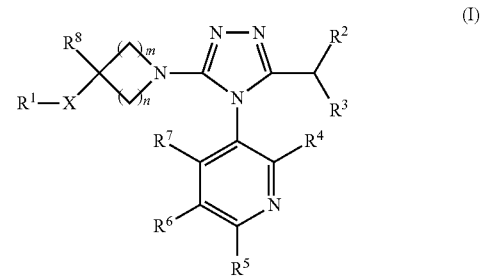

28 Claims, 1 Drawing Sheet

(56) References Cited

OTHER PUBLICATIONS

De Jong et al., "Oxytocin Involvement in SSRI-Induced Delayed Ejaculation: A Review of Animal Studies" 2007, vol. 4: 14-28.
McDougle et al., "Possible Role of Neuropeptides in Obsessive Compulsive Disorder" 1999 Psychoneuroendocrinology, vol. 24: 1-24.
Nicholson et al., "Oxytocin and Prostatic Function" 1995 Advances in Experimental Medicine and Biology, vol. 395: 529-538.
Reinheimer et al., "Barusiban, A New Highly Potent and Long-Acting Oxytocin Antagonist: Pharmacokinetic and Pharmacodynamic Comparison with Atosiban in a Cynomolgus Monkey Model of Preterm Labor" 2005 Journal of Clinical Endocrinology and Metabolism, 90(4): 2275-2281.
Thibonnier, "Development and Therapeutic Indications of Orally-Active Non-Peptide Vasopressin Receptor Antagonists" 1998 Expert Opinion on Investigational Drugs, 7(5): 729-740.
Uckert et al, "In Vitro Functional Responses of Isolated Human Vaginal Tissue to Selective Phosphodiesterase Inhibitors" 2005 World Journal of Urology, vol. 23: 398-404.
Vippagunta et al., "Crystalline Solids" 2001 Advanced Drug Delivery Reviews vol. 48: 3-26.

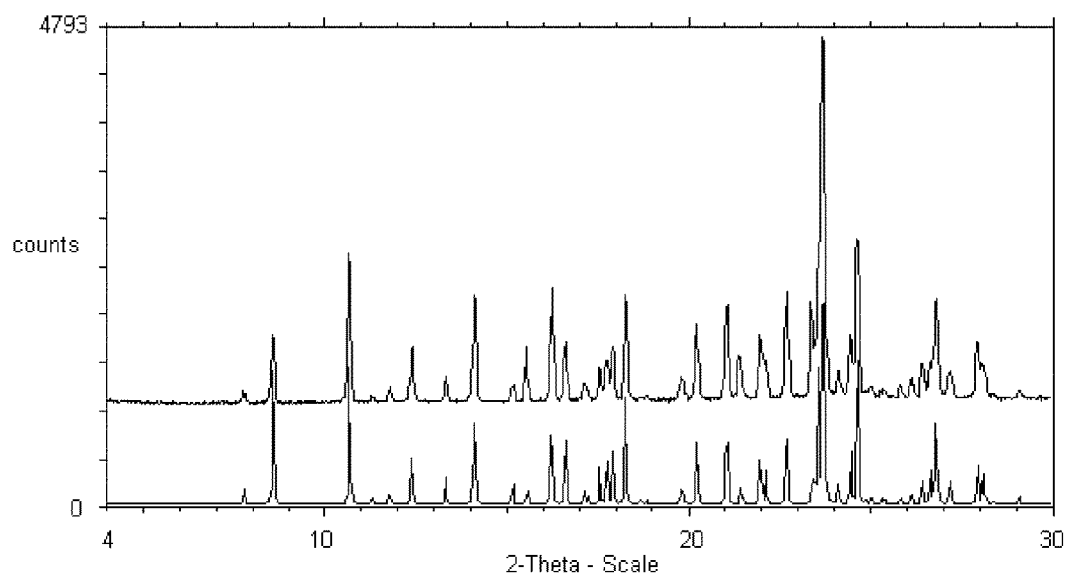

SUBSTITUTED TRIAZOLE DERIVATIVES AS OXYTOCIN ANTAGONISTS

This application is a continuation of U.S. application Ser. No. 14/691,319, filed Apr. 20, 2015, which is a continuation of U.S. application Ser. No. 13/478,384, filed May 23, 2012, now U.S. Pat. No. 9,023,872, which is a divisional of U.S. application Ser. No. 12/466,785, filed May 15, 2009, now U.S. Pat. No. 8,207,198, which is a divisional of U.S. application Ser. No. 11/335,940, filed Jan. 20, 2006, now U.S. Pat. No. 7,557,131, which claims priority from United Kingdom Application Number 0501190.3, filed Jan. 20, 2005, and U.S. Application No. 60/649,892 filed Feb. 2, 2005.

The present invention relates to a class of substituted triazoles with activity as oxytocin antagonists, uses thereof, processes for the preparation thereof and compositions containing said inhibitors. These inhibitors have utility in a variety of therapeutic areas including sexual dysfunction, particularly premature ejaculation (P.E.).

BRIEF DESCRIPTION OF THE FIGURE

FIG. 1 shows a comparison of the measured and calculated patterns for a pure phase of Example 25A.

The present invention provides for compounds of formula (I):

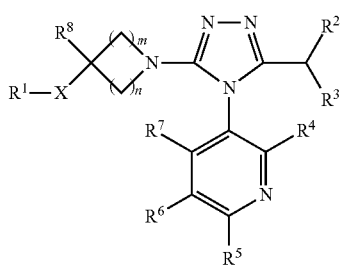

wherein:
m is in the range of 1 to 4 and n is 1 or 2 provided that m+n is in the range of 2 to 5;
X is selected from O, NH, N($C_1$-$C_6$)alkyl, NC(O)($C_1$-$C_6$)alkyl, N($SO_2$($C_1$-$C_6$)alkyl), S and $SO_2$;
$R^1$ is selected from:
(i) a phenyl or naphthyl ring;
(ii) a 5 to 6 membered aromatic heterocyclic ring containing 1 to 3 heteroatoms independently selected from N, O and S and N-oxides thereof;
(iii) a 9 to 10 membered bicyclic aromatic heterocyclic ring containing 1 to 4 heteroatoms independently selected from N, O and S and N-oxides thereof; and
(iv) 2-pyridonyl;
each of which is optionally substituted with one or more substituents independently selected from halo, ($C_1$-$C_6$)alkyl, ($C_1$-$C_6$)alkoxy, ($C_1$-$C_6$)alkoxy($C_1$-$C_6$)alkyl, cyano, $CF_3$, NH($C_1$-$C_6$)alkyl, N(($C_1$-$C_6$)alkyl)$_2$, CO($C_1$-$C_6$)alkyl, C(O)NH($C_1$-$C_6$)alkyl, C(O)N(($C_1$-$C_6$)alkyl)$_2$, C(O)OH and C(O)$NH_2$;
$R^2$ is selected from:
(i) H or hydroxy;
(ii) ($C_1$-$C_6$)alkyl, which is optionally substituted by O($C_1$-$C_6$)alkyl or phenyl;
(iii) O($C_1$-$C_6$)alkyl, which is optionally substituted by O($C_1$-$C_6$)alkyl;
(iv) NH($C_1$-$C_6$)alkyl, said alkyl group being optionally substituted by O($C_1$-$C_6$)alkyl;
(v) N(($C_1$-$C_6$)alkyl)$_2$, one or both of said alkyl groups being optionally substituted by O($C_1$-$C_6$)alkyl;
(vi) a 5 to 8 membered N-linked saturated or partially saturated heterocycle containing 1 to 3 heteroatoms, each independently selected from N, O and S, wherein at least one heteroatom is N and said ring may optionally incorporate one or two carbonyl groups; said ring being optionally substituted with one or more groups selected from CN, halo, ($C_1$-$C_6$)alkyl, O($C_1$-$C_6$)alkyl, NH($C_1$-$C_6$)alkyl, N(($C_1$-$C_6$)alkyl)$_2$, C(O)($C_1$-$C_6$)alkyl, C(O)NH($C_1$-$C_6$)alkyl, C(O)N(($C_1$-$C_6$)alkyl)$_2$, C(O)OH, C(O)$NH_2$ and C(O)O$CH_2$Ph; and
(vii) a 5 to 7 membered N-linked aromatic heterocycle containing 1 to 3 heteroatoms each independently selected from N, O and S, wherein at least one heteroatom is N; said ring being optionally substituted with one or more groups selected from CN, halo, ($C_1$-$C_6$)alkyl, O($C_1$-$C_6$)alkyl, NH($C_1$-$C_6$)alkyl, N(($C_1$-$C_6$)alkyl)$_2$, C(O)($C_1$-$C_6$)alkyl, C(O)NH($C_1$-$C_6$)alkyl, C(O)N(($C_1$-$C_6$)alkyl)$_2$, C(O)OH, C(O)$NH_2$ and C(O)O$CH_2$Ph;
$R^3$ is selected from H, ($C_1$-$C_6$)alkyl and ($C_1$-$C_6$)alkoxy($C_1$-$C_6$)alkyl;
$R^4$, $R^5$, $R^6$ and $R^7$ are each independently selected from H, halo, hydroxy, CN, ($C_1$-$C_6$)alkyl, NH($C_1$-$C_6$)alkyl, N(($C_1$-$C_6$)alkyl)$_2$ and O($C_1$-$C_6$)alkyl; and
$R^8$ is selected from H, ($C_1$-$C_6$)alkyl, ($C_1$-$C_6$)alkoxy($C_1$-$C_6$)alkyl, $CH_2$OH, $CH_2NH_2$, $CH_2$NH($C_1$-$C_6$)alkyl, $CH_2$N(($C_1$-$C_6$)alkyl)$_2$, CN, C(O)$NH_2$, C(O)NH($C_1$-$C_6$)alkyl and C(O)N(($C_1$-$C_6$)alkyl)$_2$;
a tautomer thereof or a pharmaceutically acceptable salt, solvate or polymorph of said compound or tautomer.

Unless otherwise indicated, alkyl and alkoxy groups may be straight or branched and contain 1 to 6 carbon atoms and typically 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

Halo means fluoro, chloro, bromo or iodo and is in particular fluoro or chloro.

A heterocycle may be saturated, partially saturated or aromatic. Examples of saturated heterocyclic groups are tetrahydrofuranyl, thiolanyl, pyrrolidinyl, pyrrolinyl, imidazolidinyl, imidazolinyl, sulfolanyl, dioxolanyl, dihydropyranyl, tetrahydropyranyl, piperidinyl, pyrazolinyl, pyrazolidinyl, dioxanyl, morpholinyl, dithianyl, thiomorpholinyl, piperazinyl, azepinyl, oxazepinyl, thiazepinyl, thiazolinyl and diazapanyl. Examples of aromatic heterocyclic groups are pyrrolyl, furanyl, thiophenyl, pyrazolyl, imidazolyl, isoxazolyl, oxazolyl, isothiazolyl, thiazolyl, 1,2,3-triazolyl, 1,2,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl and triazinyl. Examples of bicyclic aromatic heterocyclic groups are benzofuranyl, benzothiophenyl, indolyl, benzimidazolyl, indazolyl, benzotriazolyl, quinolinyl and isoquinolinyl.

Ph means phenyl.

Unless otherwise indicated, the term substituted means substituted by one or more defined groups. In the case where groups may be selected from a number of alternative groups, the selected groups may be the same or different.

In one embodiment, the present invention provides for compounds of formula (I) wherein:

m is in the range of 1 to 4 and n is 1 or 2 provided that m+n is in the range of 2 to 5;

X is selected from O, NH, N($C_1$-$C_6$)alkyl, and N($SO_2$($C_1$-$C_6$)alkyl);

$R^1$ is selected from:
(i) a phenyl ring;
(ii) a 5 to 6 membered aromatic heterocyclic ring containing 1 to 3 nitrogen atoms; and
(iii) 2-pyridonyl;

each of which is optionally substituted with one or more substituents independently selected from halo, ($C_1$-$C_6$)alkyl, ($C_1$-$C_6$)alkoxy, ($C_1$-$C_6$)alkoxy($C_1$-$C_6$)alkyl, cyano, $CF_3$, NH($C_1$-$C_6$)alkyl, N(($C_1$-$C_6$)alkyl)$_2$, CO($C_1$-$C_6$)alkyl, C(O)O($C_1$-$C_6$)alkyl, C(O)NH($C_1$-$C_6$)alkyl, C(O)N(($C_1$-$C_6$)alkyl)$_2$, C(O)OH and C(O)NH$_2$;

$R^2$ is selected from:
(i) H or hydroxy;
(ii) ($C_1$-$C_3$)alkyl, which is optionally substituted by O($C_1$-$C_3$)alkyl;
(iii) O($C_1$-$C_3$)alkyl, which is optionally substituted by O($C_1$-$C_3$)alkyl;
(iv) NH($C_1$-$C_3$)alkyl, said alkyl group being optionally substituted by O($C_1$-$C_3$)alkyl;
(v) N(($C_1$-$C_3$)alkyl)$_2$, one or both of said alkyl groups being optionally substituted by O($C_1$-$C_3$)alkyl;
(vi) a 5 to 6 membered N-linked saturated heterocycle containing 1 to 2 nitrogen atoms; said ring may optionally incorporate one or two carbonyl groups; said ring being optionally substituted by C(O)NH$_2$ or C(O)OCH$_2$Ph; and
(vii) a 5 to 6 membered N-linked aromatic heterocycle containing 1 to 3 heteroatoms each independently selected from N, O and S, wherein at least one heteroatom is N;

$R^3$ is selected from H, ($C_1$-$C_6$)alkyl and ($C_1$-$C_6$)alkoxy($C_1$-$C_6$)alkyl;

$R^4$, $R^5$, $R^6$ and $R^7$ are each independently selected from H, halo, hydroxy, CN, ($C_1$-$C_6$)alkyl, NH($C_1$-$C_6$)alkyl, N(($C_1$-$C_6$)alkyl)$_2$ and O($C_1$-$C_6$)alkyl; and $R^8$ is selected from H, ($C_1$-$C_3$)alkyl, ($C_1$-$C_3$)alkoxy($C_1$-$C_3$)alkyl, CH$_2$OH, CH$_2$NH$_2$, CH$_2$NH($C_1$-$C_3$)alkyl, CH$_2$N(($C_1$-$C_3$)alkyl)$_2$, CN, C(O)NH$_2$, C(O)NH($C_1$-$C_3$)alkyl and C(O)N(($C_1$-$C_3$)alkyl)$_2$;

a tautomer thereof or a pharmaceutically acceptable salt, solvate or polymorph of said compound or tautomer.

In a further embodiment, the present invention provides for compounds of formula (I) wherein:

m is in the range of 1 to 3 and n is 1 or 2;

X is selected from O, NH, N($C_1$-$C_3$)alkyl, and N($SO_2$($C_1$-$C_3$)alkyl);

$R^1$ is selected from:
(i) a phenyl ring;
(ii) a 5 to 6 membered aromatic heterocyclic ring containing 1 to 3 nitrogen atoms; and
(iii) 2-pyridonyl;

each of which is optionally substituted with one or more substituents independently selected from halo, ($C_1$-$C_6$)alkyl, ($C_1$-$C_6$)alkoxy, ($C_1$-$C_6$)alkoxy($C_1$-$C_6$)alkyl, cyano, $CF_3$, NH($C_1$-$C_6$)alkyl, N(($C_1$-$C_6$)alkyl)$_2$, O($C_1$-$C_6$)alkyl, C(O)O($C_1$-$C_6$)alkyl, C(O)NH($C_1$-$C_6$)alkyl, C(O)N(($C_1$-$C_6$)alkyl)$_2$, C(O)OH and C(O)NH$_2$;

$R^2$ is selected from:
(i) H or hydroxy;
(ii) ($C_1$-$C_3$)alkyl, which is optionally substituted by O($C_1$-$C_3$)alkyl;
(iii) O($C_1$-$C_3$)alkyl, which is optionally substituted by O($C_1$-$C_3$)alkyl;
(iv) NH($C_1$-$C_3$)alkyl, said alkyl group being optionally substituted by O($C_1$-$C_3$)alkyl; and
(v) N(($C_1$-$C_3$)alkyl)$_2$, one or both of said alkyl groups being optionally substituted by O($C_1$-$C_3$)alkyl;

$R^3$ is selected from H, ($C_1$-$C_6$)alkyl and ($C_1$-$C_6$)alkoxy($C_1$-$C_6$)alkyl;

$R^4$, $R^5$, $R^6$ and $R^7$ are each independently selected from H, halo, hydroxy, ($C_1$-$C_6$)alkyl and O($C_1$-$C_6$)alkyl; and $R^8$ is selected from H, methyl, ethyl, isopropyl, methoxymethyl, methoxyethyl, CH$_2$OH, CH$_2$NH$_2$, CH$_2$NHCH$_3$, CH$_2$N(CH$_3$)$_2$, CN, C(O)NH$_2$, C(O)NHCH$_3$, and C(O)N(CH$_3$)$_2$;

a tautomer thereof or a pharmaceutically acceptable salt, solvate or polymorph of said compound or tautomer.

In yet a further embodiment, the present invention provides for compounds of formula (I) wherein:

m is 1 or 2 and n is 1 or 2;

X is selected from O, NH, NCH$_3$ and N(SO$_2$CH$_3$);

$R^1$ is selected from phenyl, pyridinyl, pyrimidinyl, pyridazinyl, pyrazinyl, pyrazolyl and 2-pyridonyl each of which is optionally substituted with one to three substituents independently selected from halo, ($C_1$-$C_6$)alkyl, ($C_1$-$C_6$)alkoxy, ($C_1$-$C_6$)alkoxy($C_1$-$C_6$)alkyl, cyano, $CF_3$, N(($C_1$-$C_6$)alkyl)$_2$, C(O)N(($C_1$-$C_6$)alkyl)$_2$, and C(O)NH$_2$;

$R^2$ is selected from:
(i) H or hydroxy;
(ii) ($C_1$-$C_3$)alkyl, which is optionally substituted by O($C_1$-$C_3$)alkyl; and
(iii) O($C_1$-$C_3$)alkyl, which is optionally substituted by O($C_1$-$C_3$)alkyl;

$R^3$ is H or ($C_1$-$C_3$)alkyl;

$R^4$, $R^5$, $R^6$ and $R^7$ are each independently selected from H, chloro, fluoro, hydroxy, methyl and methoxy; and $R^8$ is H or methyl;

a tautomer thereof or a pharmaceutically acceptable salt, solvate or polymorph of said compound or tautomer.

In yet a further embodiment, the present invention provides for compounds of formula (I) wherein:

m and n are both 1, or m and n are both 2, or m is 1 and n is 2;

X is O or NCH$_3$;

$R^1$ is selected from phenyl, pyridinyl, pyrimidinyl, pyridazinyl, pyrazinyl, pyrazolyl and 2-pyridonyl, each of which is optionally substituted with one to three substituents independently selected from chloro, fluoro, methyl, ethyl, isopropyl, methoxy, cyano, $CF_3$, N(CH$_3$)$_2$, C(O)N(CH$_3$)$_2$, and C(O)NH$_2$;

$R^2$ is selected from H, hydroxy, methyl, methoxy and ethoxy;

$R^3$ is H or CH$_3$;

$R^4$ is H or methyl;

$R^5$ is hydroxy or methoxy;

$R^6$ and $R^7$ are both H; and $R^8$ is H or methyl;

a tautomer thereof or a pharmaceutically acceptable salt, solvate or polymorph of said compound or tautomer.

In yet a further embodiment, the present invention provides for compounds of formula (I) wherein:

m and n are both 1, or m and n are both 2, or m is 1 and n is 2;

X is O;

$R^1$ is selected from phenyl, pyridinyl, pyrimidinyl, pyridazinyl, pyrazinyl, pyrazolyl and 2-pyridonyl, each of which is optionally substituted with one to three substituents independently selected from chloro, fluoro, methyl, ethyl, isopropyl, methoxy, cyano, $CF_3$, N(CH$_3$)$_2$, C(O)N(CH$_3$)$_2$, and C(O)NH$_2$;

$R^2$ is selected from H, methyl, methoxy and ethoxy;
$R^3$, $R^4$, $R^6$, $R^7$ and $R^8$ are H; and
$R^5$ is methoxy;
a tautomer thereof or a pharmaceutically acceptable salt, solvate or polymorph of said compound or tautomer.

In one embodiment, m is in the range of 1 to 3 and n is 1 or 2. In a further embodiment, m is 1 or 2 and n is 1 or 2. In yet a further embodiment, m and n are both 1, or m and n are both 2, or m is 1 and n is 2.

In one embodiment, X is selected from O, NH, $N(C_1-C_6)$ alkyl, and $N(SO_2(C_1-C_6)$alkyl). In a further embodiment, X is selected from O, NH, $N(C_1-C_3)$alkyl, and $N(SO_2(C_1-C_3)$ alkyl). In yet a further embodiment, X is selected from O, NH, $NCH_3$ and $N(SO_2CH_3)$. In yet a further embodiment, X is O or $NCH_3$. In yet a further embodiment, X is O.

In one embodiment, $R^1$ is selected from:
(i) a phenyl or naphthyl ring;
(ii) a 5 to 6 membered aromatic heterocyclic ring containing 1 to 3 hetero atoms independently selected from N, O and S and N-oxides thereof;
(iii) a 9 to 10 membered bicyclic aromatic heterocyclic ring containing 1 to 4 nitrogen atoms; and
(iv) 2-pyridonyl;
each of which is optionally substituted with one or more substituents independently selected from halo, $(C_1-C_6)$alkyl, $(C_1-C_6)$alkoxy, $(C_1-C_6)$alkoxy$(C_1-C_6)$alkyl, cyano, $CF_3$, $NH(C_1-C_6)$alkyl, $N((C_1-C_6)$alkyl$)_2$, $CO(C_1-C_6)$alkyl, $C(O)O(C_1-C_6)$alkyl, $C(O)NH(C_1-C_6)$alkyl, $C(O)N((C_1-C_6)$alkyl$)_2$, $C(O)OH$ and $C(O)NH_2$.

In a further embodiment, $R^1$ is selected from:
(i) a phenyl ring;
(ii) a 5 to 6 membered aromatic heterocyclic ring containing 1 to 3 nitrogen atoms; and
(iii) 2-pyridonyl;
each of which is optionally substituted with one or more substituents independently selected from halo, $(C_1-C_6)$alkyl, $(C_1-C_6)$alkoxy, $(C_1-C_6)$alkoxy$(C_1-C_6)$alkyl, cyano, $CF_3$, $NH(C_1-C_6)$alkyl, $N((C_1-C_6)$alkyl$)_2$, $CO(C_1-C_6)$alkyl, $C(O)O(C_1-C_6)$alkyl, $C(O)NH(C_1-C_6)$alkyl, $C(O)N((C_1-C_6)$alkyl$)_2$, $C(O)OH$ and $C(O)NH_2$.

In yet a further embodiment, $R^1$ is selected from:
(i) a phenyl ring;
(ii) a 5 to 6 membered aromatic heterocyclic ring containing 1 to 3 nitrogen atoms; and
(iii) 2-pyridonyl;
each of which is optionally substituted with one or more substituents independently selected from halo, $(C_1-C_6)$alkyl, $(C_1-C_6)$alkoxy, $(C_1-C_6)$alkoxy$(C_1-C_6)$alkyl, cyano, $CF_3$, $NH(C_1-C_6)$alkyl, $N((C_1-C_6)$alkyl$)_2$, $CO(C_1-C_6)$alkyl, $C(O)O(C_1-C_6)$alkyl, $C(O)NH(C_1-C_6)$alkyl, $C(O)N((C_1-C_6)$alkyl$)_2$, $C(O)OH$ and $C(O)NH_2$.

In yet a further embodiment, $R^1$ is selected from:
(i) a phenyl ring;
(ii) a 5 to 6 membered aromatic heterocyclic ring containing 1 to 3 nitrogen atoms; and
(iii) 2-pyridonyl;
each of which is optionally substituted with one or more substituents independently selected from halo, $(C_1-C_6)$alkyl, $(C_1-C_6)$alkoxy, $(C_1-C_6)$alkoxy$(C_1-C_6)$alkyl, cyano, $CF_3$, $N((C_1-C_6)$alkyl$)_2$, $C(O)N((C_1-C_6)$alkyl$)_2$, and $C(O)NH_2$.

In yet a further embodiment, $R^1$ is selected from phenyl, pyridinyl, pyrimidinyl, pyridazinyl, pyrazinyl, pyrazolyl and 2-pyridonyl, each of which is optionally substituted with one or more substituents independently selected from halo, $(C_1-C_6)$alkyl, $(C_1-C_6)$alkoxy, $(C_1-C_6)$alkoxy$(C_1-C_6)$alkyl, cyano, $CF_3$, $N((C_1-C_6)$alkyl$)_2$, $C(O)N((C_1-C_6)$alkyl$)_2$, and $C(O)NH_2$.

In yet a further embodiment, $R^1$ is selected from phenyl, pyridinyl, pyrimidinyl, pyridazinyl, pyrazinyl, pyrazolyl and 2-pyridonyl, each of which is optionally substituted with one to three substituents independently selected from halo, $(C_1-C_6)$alkyl, $(C_1-C_6)$alkoxy, $(C_1-C_6)$alkoxy$(C_1-C_6)$alkyl, cyano, $CF_3$, $N((C_1-C_6)$alkyl$)_2$, $C(O)N((C_1-C_6)$alkyl$)_2$, and $C(O)NH_2$.

In yet a further embodiment, $R^1$ is selected from phenyl, pyridinyl, pyrimidinyl, pyridazinyl, pyrazinyl, pyrazolyl and 2-pyridonyl, each of which is optionally substituted with one to three substituents independently selected from chloro, fluoro, methyl, ethyl, isopropyl, methoxy, cyano, $CF_3$, $N(CH_3)_2$, $C(O)N(CH_3)_2$, and $C(O)NH_2$.

In yet a further embodiment, $R^1$ is selected from phenyl, pyridinyl, pyrimidinyl, pyridazinyl, pyrazinyl and 2-pyridonyl, each of which is optionally substituted with one to three substituents independently selected from chloro, fluoro, methyl, ethyl, isopropyl, methoxy, cyano, $CF_3$, $N(CH_3)_2$, $C(O)N(CH_3)_2$, and $C(O)NH_2$.

In one embodiment, $R^2$ is selected from:
(i) H or hydroxy;
(ii) $(C_1-C_3)$alkyl, which is optionally substituted by $O(C_1-C_3)$alkyl;
(iv) $O(C_1-C_3)$alkyl, which is optionally substituted by $O(C_1-C_3)$alkyl;
(v) $NH(C_1-C_3)$alkyl, said alkyl group being optionally substituted by $O(C_1-C_3)$alkyl;
(vi) $N((C_1-C_3)$alkyl$)_2$, wherein one or both of said alkyl groups may be optionally substituted by $O(C_1-C_3)$alkyl;
(vii) a 5 to 6 membered N-linked saturated heterocycle containing 1 to 2 nitrogen atoms; said ring may optionally incorporate one or two carbonyl groups; said ring being optionally substituted by $C(O)NH_2$ or $C(O)OCH_2Ph$; and
(viii) a 5 to 6 membered N-linked aromatic heterocycle containing 1 to 3 heteroatoms each independently selected from N, O and S, wherein at least one heteroatom is N.

In a further embodiment, $R^2$ is selected from:
(i) H or hydroxy;
(ii) $(C_1-C_3)$alkyl, which is optionally substituted by $O(C_1-C_3)$alkyl;
(iii) $O(C_1-C_3)$alkyl, which is optionally substituted by $O(C_1-C_3)$alkyl;
(iv) $NH(C_1-C_3)$alkyl, said alkyl group being optionally substituted by $O(C_1-C_3)$alkyl; and
(v) $N((C_1-C_3)$alkyl$)_2$, wherein one or both of said alkyl groups may be optionally substituted by $O(C_1-C_3)$alkyl.

In yet a further embodiment, $R^2$ is selected from:
(i) H or hydroxy;
(ii) $(C_1-C_3)$alkyl, which is optionally substituted by $O(C_1-C_3)$alkyl; and
(iii) $O(C_1-C_3)$alkyl, which is optionally substituted by $O(C_1-C_3)$alkyl.

In yet a further embodiment, $R^2$ is selected from H, hydroxy, methyl, methoxy and ethoxy. In yet a further embodiment, $R^2$ is selected from H, methyl, methoxy and ethoxy.

In one embodiment, $R^3$ is H or $(C_1-C_3)$alkyl. In a further embodiment, $R^3$ is H or $CH_3$. In yet a further embodiment, $R^3$ is H.

In one embodiment, $R^4$, $R^5$, $R^6$ and $R^7$ are each independently selected from H, halo, hydroxy, $(C_1-C_6)$alkyl and $O(C_1-C_6)$alkyl. In a further embodiment, $R^4$, $R^5$, $R^6$ and $R^7$ are each independently selected from H, halo, hydroxy, ($C_1$-$C_3$)alkyl and O($C_1$-$C_3$)alkyl. In yet a further embodiment, $R^4$, $R^5$, $R^6$ and $R^7$ are each independently selected from H, chloro, fluoro, hydroxy, methyl and methoxy. In yet a further embodiment, $R^4$ is H or methyl; $R^5$ is hydroxy or methoxy; and $R^6$ and $R^7$ are both H. In yet a further embodiment, $R^4$, $R^6$ and $R^7$ are H and $R^5$ is methoxy.

In one embodiment, $R^8$ is selected from H, ($C_1$-$C_3$)alkyl, ($C_1$-$C_3$)alkoxy($C_1$-$C_3$)alkyl, $CH_2OH$, $CH_2NH_2$, $CH_2NH$ ($C_1$-$C_3$)alkyl, $CH_2N((C_1$-$C_3)alkyl)_2$, CN, $C(O)NH_2$, $C(O)NH(C_1$-$C_3)alkyl$ and $C(O)N((C_1$-$C_3)alkyl)_2$. In a further embodiment, $R^8$ is selected from H, methyl, ethyl, isopropyl, methoxymethyl, methoxyethyl, $CH_2OH$, $CH_2NH_2$, $CH_2NHCH_3$, $CH_2N(CH_3)_2$, CN, $C(O)NH_2$, $C(O)NHCH_3$, and $C(O)N(CH_3)_2$.

In yet a further embodiment, $R^8$ is selected from H, methyl, ethyl, methoxymethyl, methoxyethyl and CN. In yet a further embodiment, $R^8$ is H or methyl. In yet a further embodiment, $R^8$ is H.

It is to be understood that the invention covers all combinations of particular embodiments of the invention as described hereinabove, consistent with the definition of the compounds of formula (I).

Representative compounds of formula (I) are:

5-[3-[4-(3-fluoro-2-methylphenoxy)piperidin-1-yl]-5-(methoxymethyl)-4H-1,2,4-triazol-4-yl]-2-methoxypyridine;

2-methoxy-5-{3-(methoxymethyl)-5-[4-(2-methyl phenoxy)piperidn-1-yl]-4H-1,2,4-triazol-4-yl}pyridine;

5-[3-[4-(5-fluoro-2-methylphenoxy)piperidin-1-yl]-5-(methoxymethyl)-4H-1,2,4-triazol-4-yl]-2-methoxypyridine;

5-{3-[4-(3-fluoro-2-methylphenoxy)piperidin-1-yl]-5-methyl-4H-1,2,4-triazol-4-yl}-2-methoxypyridine;

5-[3-[4-(2-chlorophenoxy)piperidin-1-yl]-5-(methoxymethyl)-4H-1,2,4-triazol-4-yl]-2-methoxypyridine;

3-{3-[3-(4-fluoro-2-methylphenoxy)azetidin-1-yl]-5-methyl-4H-1,2,4-triazol-4-yl}-6-methoxy-2-methylpyridine;

5-[3-[4-(4-fluoro-2-methylphenoxy)piperidin-1-yl]-5-(methoxymethyl)-4H-1,2,4-triazol-4-yl]-2-methoxypyridine;

5-{3-[4-(4-fluoro-2-methylphenoxy)piperidin-1-yl]-5-methyl-4H-1,2,4-triazol-4-yl}-2-methoxypyridine;

2-methoxy-5-{3-methyl-5-[4-(2-methylphenoxy)piperidin-1-yl]-4H-1,2,4-triazol-4-yl}pyridine;

5-{3-[4-(2-chlorophenoxy)piperidin-1-yl]-5-methyl-4H-1,2,4-triazol-4-yl}-2-methoxypyridine;

5-[3-[4-(3,4-difluorophenoxy)piperidin-1-yl]-5-(methoxymethyl)-4H-1,2,4-triazol-4-yl]-2-methoxypyridine;

5-{3-[3-(2-ethyl-4-fluorophenoxy)azetidin-1-yl]-5-methyl-4H-1,2,4-triazol-4-yl}-2-methoxypyridine;

5-[3-[3-(2-chloro-4-fluorophenoxy)azetidin-1-yl]-5-(methoxymethyl)-4H-1,2,4-triazol-4-yl]-2-methoxypyridine;

5-{3-[4-(3,5-difluorophenoxy)piperidin-1-yl]-5-methyl-4H-1,2,4-triazol-4-yl}-2-methoxypyridine;

5-[3-[3-(2,3-dimethylphenoxy)azetidin-1-yl]-5-(methoxymethyl)-4H-1,2,4-triazol-4-yl]-2-methoxypyridine;

5-[3-[4-(3,5-difluorophenoxy)piperidin-1-yl]-5-(methoxymethyl)-4H-1,2,4-triazol-4-yl]-2-methoxypyridine;

5-{3-[3-(4-fluoro-2-methylphenoxy)azetidin-1-yl]-5-methyl-4H-1,2,4-triazol-4-yl}-2-methoxypyridine;

5-{3-[3-(2,3-dimethylphenoxy)azetidin-1-yl]-5-methyl-4H-1,2,4-triazol-4-yl}-2-methoxypyridine;

2-methoxy-5-(3-(methoxymethyl)-5-{3-[3-(trifluoromethyl)phenoxy]azetidin-1-yl}-4H-1,2,4-triazol-4-yl)pyridine;

5-{3-[3-(2-chloro-4-fluorophenoxy)azetidin-1-yl]-5-methyl-4H-1,2,4-triazol-4-yl}-2-methoxypyridine;

2-methoxy-5-(3-(methoxymethyl)-5-{4-[(3-methylpyridin-4-yl)oxy]piperidin-1-yl}-4H-1,2,4-triazol-4-yl)pyridine;

3-({1-[4-(6-methoxypyridin-3-yl)-5-methyl-4H-1,2,4-triazol-3-yl]piperidin-4-yl}oxy)-2-methylbenzonitrile;

2-methoxy-5-{3-[4-(3-methoxy-2-methylphenoxy)piperidin-1-yl]-5-methyl-4H-1,2,4-triazol-4-yl}pyridine; and 5-[3-[3-(3-chlorophenoxy)azetidin-1-yl]-5-(methoxymethyl)-4H-1,2,4-triazol-4-yl]-2-methoxypyridine;

and tautomers thereof and pharmaceutically acceptable salts, solvates and polymorphs of said compounds or tautomers.

Pharmaceutically acceptable salts of the compounds of formula (I) comprise the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002). All references cited herein are incorporated by reference in their entirety for all purposes.

Pharmaceutically acceptable salts of compounds of formula (I) may be prepared by one or more of three methods:

(i) by reacting the compound of formula (I) with the desired acid or base;

(ii) by removing an acid- or base-labile protecting group from a suitable precursor of the compound of formula (I) using the desired acid or base; or (iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288, by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in "Pro-drugs as Novel Delivery Systems", Vol. 14, ACS Symposium Series (T. Higuchi and W. Stella) and "Bioreversible Carriers in Drug Design", Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H. Bundgaard (Elsevier, 1985).

Some examples of prodrugs in accordance with the invention include
(i) where the compound of formula I contains a carboxylic acid functionality, an ester thereof, for example, a compound wherein the hydrogen of the carboxylic acid functionality of the compound of formula (I) is replaced by $(C_1-C_8)$alkyl; and
(ii) where the compound of formula (I) contains a primary or secondary amino functionality, an amide thereof, for example, a compound wherein, as the case may be, one or both hydrogens of the amino functionality of the compound of formula (I) is/are replaced by $(C_1-C_{10})$alkanoyl.

Further examples of replacement groups in accordance with the foregoing examples and examples of other prodrug types may be found in the aforementioned references. Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include
(i) where the compound of formula (I) contains a methyl group, an hydroxymethyl derivative thereof (—$CH_3$→—$CH_2OH$):
(ii) where the compound of formula (I) contains an alkoxy group, an hydroxy derivative thereof (—OR→—OH);
(iii) where the compound of formula (I) contains a tertiary amino group, a secondary amino derivative thereof (—$NR^1R^2$→—$NHR^1$ or —$NHR^2$);
(iv) where the compound of formula (I) contains a secondary amino group, a primary derivative thereof (—$NHR^1$→—$NH_2$);
(v) where the compound of formula (I) contains a phenyl moiety, a phenol derivative thereof (-Ph→-PhOH); and
(vi) where the compound of formula (I) contains an amide group, a carboxylic acid derivative thereof (—$CONH_2$→COOH).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, a keto group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

The present invention includes all crystal forms of the compounds of formula (I) including racemates and racemic mixtures (conglomerates) thereof. Stereoisomeric conglomerates may be separated by conventional techniques known to those skilled in the art—see, for example, "Stereochemistry of Organic Compounds" by E. L. Eliel and S. H. Wilen (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$ $^{13}C$ and $^{14}C$, chlorine, such as $^{36}Cl$, fluorine, such as $^{18}F$, iodine, such as $^{123}I$ and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing compounds of formula (I) in accordance with the invention, it is open to a person skilled in the art to routinely select the form of intermediate which provides the best combination of features for this purpose. Such features include the melting point, solubility, processability and yield of the intermediate form and the resulting ease with which the product may be purified on isolation.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques. Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999). Other means of topical administration include delivery by electroporation, iontophoresis, phonophoresis, sonophoresis and microneedle or needle-free (e.g. Powderject™, Bioject™ etc.) injection. Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound (s) of the invention comprising, for example, ethanol, aqueous ethanol, or a suitable alternative agent for dispersing, solubilising, or extending release of the active, a propellant (s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 2 to 30 mg of the compound of formula (I). The overall daily dose will typically be in the range 50 to 100 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis. Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration. Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148 and are hereto incorporated by reference without any limitation herein.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 50 mg to 100 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

Processes

Compounds of general formula (I) wherein m, n, X and $R^1$ to $R^8$ are as described herein can be prepared as described in Scheme 1.

Scheme 1

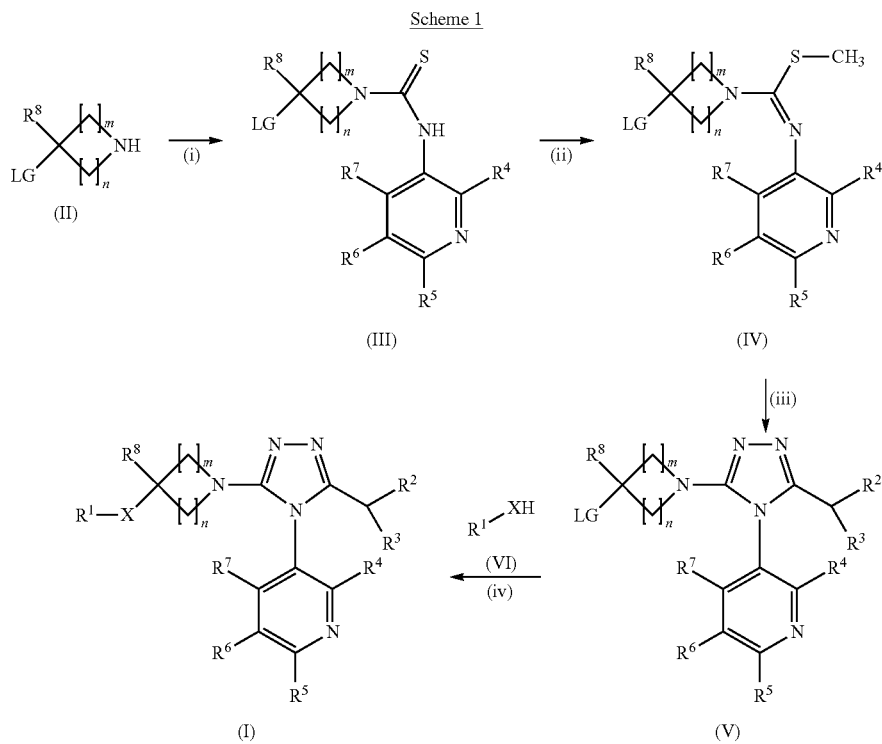

LG represents a suitable leaving group such as mesylate or tosylate and is typically mesylate. When LG is mesylate compounds of general formula (II) can be prepared as described in WO 97/25322 at p64.

Compounds of general formula (III) can be prepared from compounds of general formula (II) by process step (i), wherein thiourea formation is achieved by reaction of compound (II) with a suitable aminopyridine in the presence of a suitable thiocarbonyl transfer agent such 1'1-thiocarbonyldi-2(1H)-pyridone (J. Org. Chem. 1986, 51, 2613) or 1,1''-thiocarbonyl diimidazole, typically 1'1-thiocarbonyldi-2(1H)-pyridone, and a suitable base such as triethylamine, pyridine or Hünig's base, in a suitable solvent such as dichloromethane or tetrahydrofuran, under ambient conditions for 18 to 24 hours. Typical conditions comprise of
  a) reacting 1 equivalent of suitable aminopyridine and 1 equivalent of 1'1-thiocarbonyldi-2(1H)-pyridone in dichloromethane at 0 to 25° C. for 1 hour, then
  b) adding 1 equivalent of compound (II) and 1 equivalent of triethylamine in dichloromethane and stirring under ambient conditions for 18 hours.

Alternatively, process step (i) may involve the formation of a urea by coupling of compound (II) with a suitable aminopyridine, in the presence of a suitable carbonyl transfer agent such as N,N'-carbonyldiimidazole, followed by subsequent sulfonation using a suitable sulfonating agent such as Lawesson's reagent.

In a further embodiment compounds of general formula (III) can be prepared as described in Scheme 2.

Compounds of general formula (IV) can be prepared from compounds of general formula (III) by process step (ii) which comprises methylation of the thiourea (III) using a suitable methylating agent such as methyl iodide or methyl p-toluenesulfonate, in the presence of a suitable base such as potassium tert-butoxide in a suitable solvent such as tetrahydrofuran or diethyl ether, between 0° C. and the reflux temperature of the solvent for about 18 hrs. Typical conditions comprise reacting 1 equivalent of compound (III), 1 to 1.2 equivalents potassium tert-butoxide, 1 to 1.2 equivalents methyl p-toluenesulfonate, in tetrahydrofuran, under ambient conditions for 1 to 18 hrs.

Compounds of general formula (V) can be prepared from compounds of general formula (IV) by process step (iii) which comprises reaction of compounds of general formula (IV) with a suitable hydrazide $R^2R^3CHCONHNH_2$, optionally in the presence of a suitable acid catalyst such as trifluoroacetic acid or para-toluenesulfonic acid, in a suitable solvent such as tetrahydrofuran or n-butanol, at a temperature between room temperature and the reflux temperature of the solvent. Typical conditions comprise reacting 1 equivalent of compound (IV), an excess of hydrazide $R^2R^3CHCONHNH_2$ and trifluoroacetic acid (catalytic amount) in tetrahydrofuran, heated under reflux for 1 to 18 hours.

Alternatively, compounds of formula (V) may be prepared from compounds of formula (III) using process steps (ii) and (iii) as a one-pot synthesis.

Compounds of formula (VI) are commercially available or known in the literature.

Compounds of general formula (I) can be prepared from compounds of general formula (V) and (VI) by process step (iv) wherein compound (VI) is treated with a suitable strong base such sodium hydride or potassium tert-butoxide followed by reaction with compound (V), in a suitable solvent such as N,N-dimethylformamide or dimethylsulfoxide, at a temperature between room temperature and the reflux temperature of the solvent, for 18 to 40 hours. Typical conditions comprise reacting 2 equivalents of compound (VI), 2 equivalents of sodium hydride, and 1 equivalent of compound (V), in N,N-dimethylformamide, heated at 100° C. for up to 40 hours.

Scheme 2

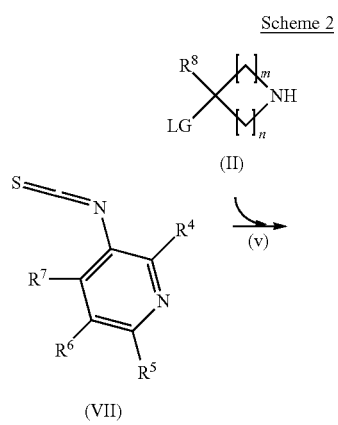

(v)

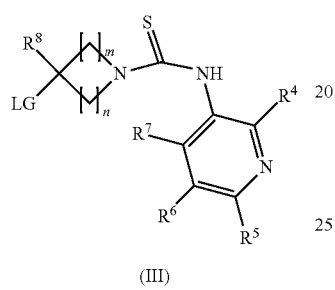

Compounds of formula (VII) can be prepared as described in J. Org. Chem. (1980), 45, 4219. Compounds of formula (II) can be prepared as described in WO 97/25322 at p64.

Compounds of formula (III) can be prepared from compounds of formula (II) and (VII) by process step (v) wherein compounds (VII) and (II) are reacted together, optionally in the presence of a suitable base such as triethylamine, pyridine or Hünig's base, in a suitable solvent such as dichloromethane or tetrahydrofuran, under ambient conditions for 2 to 24 hours. Typical conditions comprise reacting 1 equivalent of compound (VI) and 1 equivalent of compound (II) in dichloromethane, under ambient conditions for 2 to 24 hours.

Alternatively compounds of formula (I) can also be prepared as described in Scheme 3.

Scheme 3

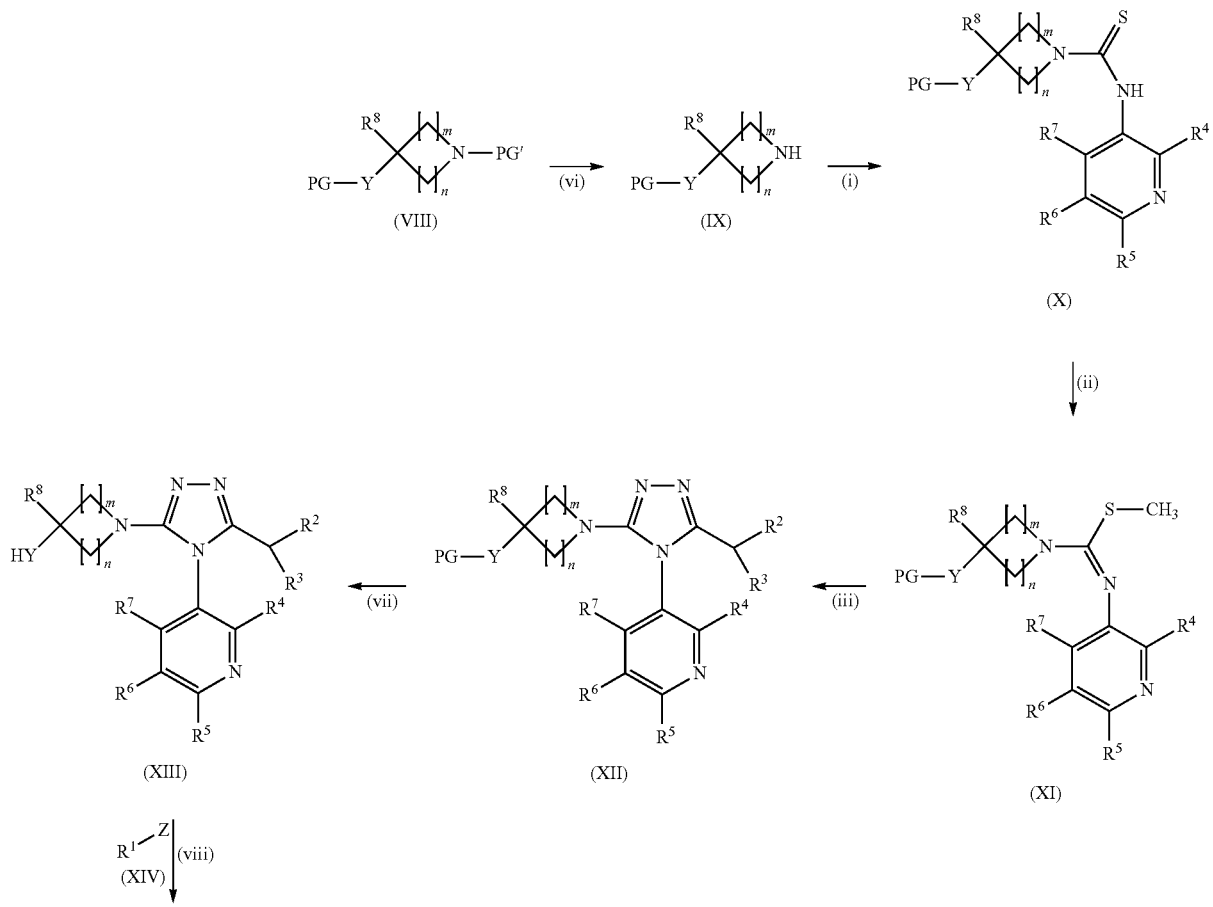

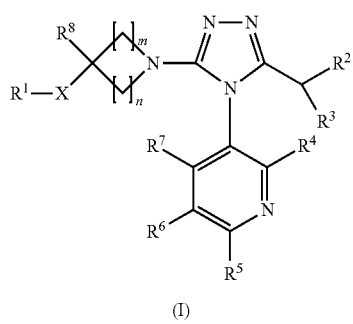

(I)

Y represents O or N(C₁-C₆)alkyl.

Z represent a suitable functional group such as OH or halogen. When Y=O, Z is typically OH; when Y=N(C₁-C₆)alkyl, Z is typically halogen, in particular chloro or bromo.

PG represents a suitable protecting group. When Y=O, PG is typically acyl or benzyl.

When Y=N(C₁-C₆)alkyl, PG is typically Boc or CBz.

PG' represents a suitable amine protecting group such as benzyl or Boc

Compounds of formula (VIII) can be prepared by analogy with the methods used by M. G. Banwell (*J. Org. Chem.* 2003, 68, 613).

Compounds of general formula (IX) can be prepared from compounds of general formula (VIII) by process step (vi) which comprises deprotection of the amino group using standard methodology as described in "Protecting Groups in Organic Synthesis" by T. W. Greene and P. Wutz. Typical conditions comprise reacting 1 equivalent of compound (VIII) in the presence of a suitable catalyst, such as 10% Pd/C, in a suitable solvent, such as ethanol/water (90:10) or tetrahydrofuran, under 60 psi of hydrogen at room temperature for 2 to 18 hours.

Compounds of general formula (X) can be prepared from compounds of general formula (IX) by process step (i) as described in Scheme 1.

Alternatively, compounds of formula (X) can be prepared from compounds of formula (IX) and (VII) by process step (v), as described in Scheme 2.

Compounds of general formula (XI) can be prepared from compounds of general formula (X) by process step (ii) as described in Scheme 1.

Compounds of general formula (XII) can be prepared from compounds of general formula (XI) by process step (iii) as described in Scheme 1.

Compounds of formula (XIII) may be prepared from compounds of general formula (XII) by process step (vii) which comprises deprotection of Y using standard methodology as described in "Protecting Groups in Organic Synthesis" by T. W. Greene and P. Wutz.

When PG=acyl, typical conditions comprise reacting 1 equivalent of compound (XI) and 2.5 to 3 equivalents of potassium carbonate in dichloromethane under ambient conditions for 18 hours.

When PG=benzyl, typical conditions comprise reacting 1 equivalent of compound (XI) in the presence of a suitable catalyst, such as 10% Pd/C, in a suitable solvent, such as ethanol/water (90:10) or tetrahydrofuran, under 60 psi of hydrogen at room temperature for 2 to 18 hours.

Compounds of formula (I) can be prepared from compounds of general formula (XIII) and R¹Z (XIV) by process step (viii).

When Z=OH compounds of formula (I) can be obtained by a suitable reaction, typically a Mitsunobu reaction, between compounds (XIII) and (XIV) in the presence of a suitable phosphine, such as tri-n-butyl phosphine or triphenyl phosphine, and a suitable azo compound, such as diisopropylazodicarboxylate or di-tert-butyl azodicarboxylate, in a solvent such as dichloromethane, tetrahydrofuran or N,N-dimethylformamide, at temperatures between 25 to 115° C., for 1 to 48 hours. Typical conditions comprise reacting 1 equivalent of compound (I), 2 equivalents of compound (XIV), 3 equivalents of triphenylphosphine and 2 equivalents of di-tert-butyl azodicarboxylate, in dichloromethane, at 25° C. for 4 hours.

When X=N(C₁-C₆)alkyl and Z=halogen (e.g. Cl), compounds of formula (I) can be obtained by a suitable reaction, typically a N-alkylation, between compounds (XIII) and (XIV), in the presence of a suitable base such as N,N-diisopropylethylamine or triethylamine, in a suitable solvent such as N,N-dimethylformamide or dimethylsulfoxide, at elevated temperature for 1 to 18 hours. Typical conditions comprise reacting 1 equivalent of compound (XIII), 1 to 1.2 equivalents of compound (XIV) and 1 to 2 equivalents of N,N-diisopropylethylamine, in dimethylsulfoxide at elevated temperature for 16 hours.

Compounds of formula (I) can alternatively be prepared as described in Scheme 4.

Scheme 4

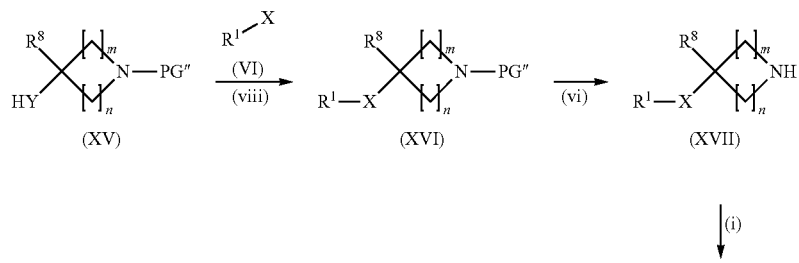

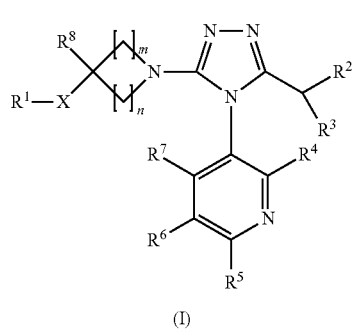

(I)

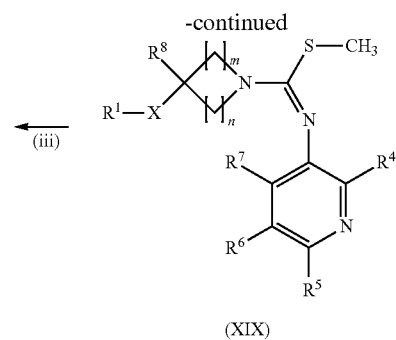

(XIX)

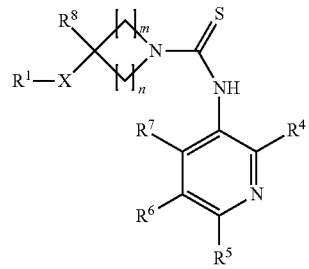

(XVIII)

Y represents O or N(C$_1$-C$_6$)alkyl.

PG″ represents a suitable amine protecting group, typically benzyl.

When Y=O, compounds of general formula (XV) are commercially available.

When Y=N(C$_1$-C$_6$)alkyl, compounds of formula (XV) can be prepared as described in WO 03/089412 at page 22.

Compounds of general formula (XVI) may be prepared from compounds of formula (XV) and (VI) by process step (viii) as described in Scheme 3.

Compounds of general formula (XVII) may be prepared from compounds of formula (XVI) by process step (vi) as described in Scheme 3.

Compounds of general formula (XVIII) may be prepared from compounds of formula (XVII) by process step (i) as described in Scheme 1.

Alternatively, compounds of formula (XVIII) can be prepared from compounds of formula (XVII) and (VII) by process step (v), as described in Scheme 2.

Compounds of general formula (XIX) may be prepared from compounds of formula (XVIII) by process step (ii) as described in Scheme 1.

Compounds of general formula (I) may be prepared from compounds of formula (XIX) by process step (iii) as described in Scheme 1.

Alternatively, compounds of general formula (I) may be prepared from compounds of formula (XVIII) by combination of process steps (ii) and (iii), in a one-pot synthesis, as described in Scheme 1.

In a further embodiment, where X=O and m, n, and R$^1$ to R$^8$ are as described herein, compounds of formula (I) can be prepared as described in Scheme 5.

Scheme 5

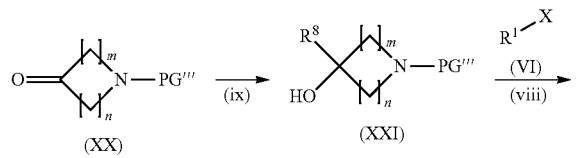

(XX)        (XXI)

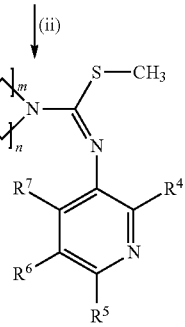

(XXII)

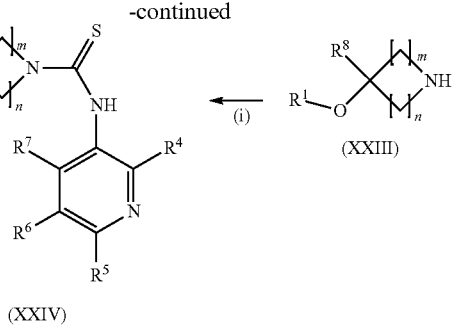

(XXIV)

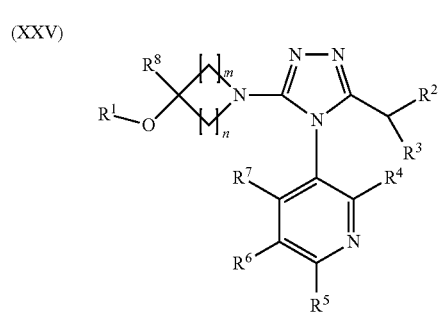

(XXV)

(I)

PG″ is a suitable protecting amine group, typically diphenylmethyl.

Compounds of formula (XX) are commercially available.

Compounds of formula (XXI) may be prepared from compounds of formula (XX) by process step (ix) which comprises reaction of ketone (XX) with an "activated" alkyl (organometallic alkyl such as R$^8$MgI, R$^8$MgCl or R$^8$Li) to give the corresponding tertiary alcohol of formula (XXI). Typical conditions comprise reacting 1 equivalent of compound (XX) and 2 to 2.5 equivalents of R$^8$MgI in a suitable solvent such as tetrahydrofuran or diethyl ether, at 0 to 25° C. for 1 to 8 hours.

Compounds of formula (XXII) may be prepared from compounds of formula (XXI) and (VI) by process step (viii) as described in Scheme 3.

Compounds of formula (XXIII) may be prepared from compounds of formula (XXII) by process step (vi) as described in Scheme 3.

Compounds of formula (XXIV) may be prepared from compounds of formula (XXIII) by process step (i) as described in Scheme 1.

Compounds of formula (XXV) may be prepared from compounds of formula (XXIV) by process step (ii) as described in Scheme 1.

Compounds of formula (I) may be prepared from compounds of formula (XXV) by process step (iii) as described in Scheme 1.

Alternatively, Scheme 6 provides a route to the preparation of compounds of formula (I).

Compounds of formula (XXX) can be prepared from compounds of general formula (XXIX) by process step (ii) as described in Scheme 1.

Compounds of formula (I) can be prepared from compounds of general formula (XXX) and (VI) by process step (iv) as described in Scheme 1.

All of the above reactions and the preparations of novel starting materials disclosed in the preceding methods are conventional and appropriate reagents and reaction conditions for their performance or preparation as well as procedures for isolating the desired products will be well known to those skilled in the art with reference to literature precedents and the examples and preparations hereto.

The compounds of the invention are useful because they have pharmacological activity in mammals, including humans. More particularly, they are useful in the treatment or prevention of a disorder in which modulation of the levels

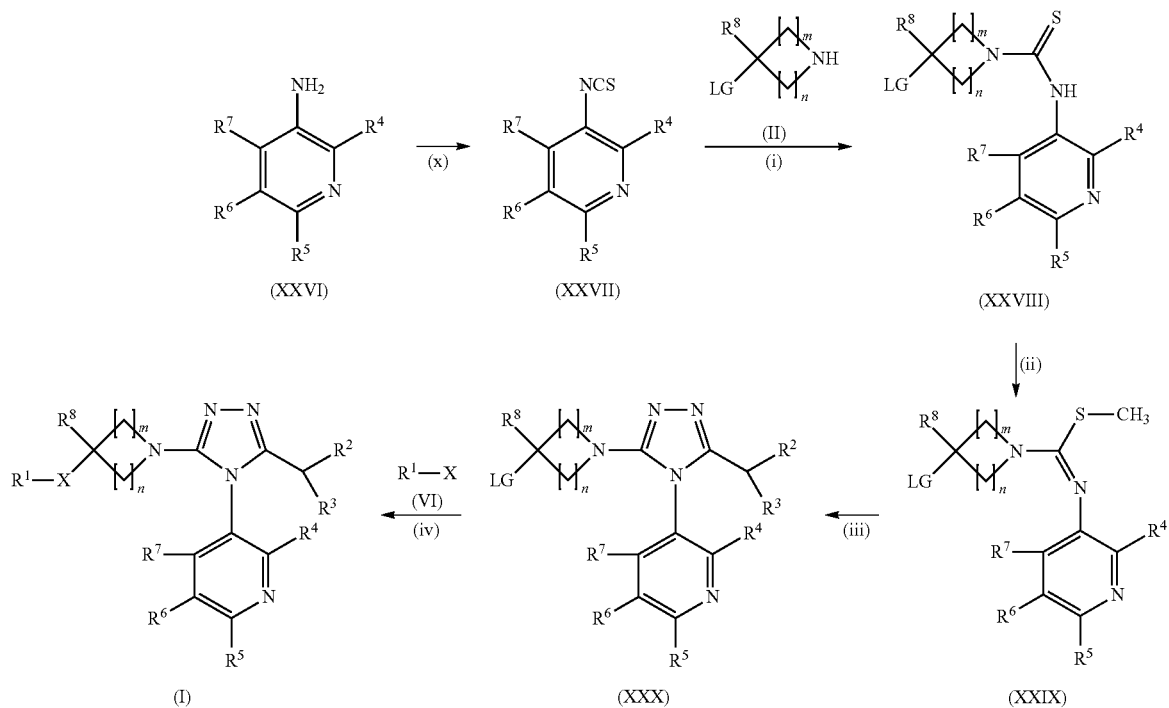

Scheme 6

Compounds of formula (XXVI) may be prepared as described in WO 04/062665 at p46.

Compounds of formula (XXVII) may be prepared from compounds of formula (XXVI) by process step (x) which comprises treatment of compound (XXVI) with a suitable thiocarbonyl transfer agent thiourea such 1'1-thiocarbonyldi-2(1H)-pyridone (J. Org. Chem. 1986, 51, 2613), in a suitable solvent such as dichloromethane or tetrahydrofuran, under ambient conditions for 1 to 18 hours. Typical conditions comprise reacting 1.0 equivalent of compound (XXVI) and 1.0 equivalent of 1'1-thiocarbonyldi-2(1H)-pyridone in dichloromethane at room temperature for 18 hours.

Compounds of formula (XXVIII) can be prepared from compounds of general formula (XXVII) by process step (i) as described in Scheme 1.

Compounds of formula (XXIX) can be prepared from compounds of general formula (XXVIII) by process step (ii) as described in Scheme 1.

of oxytocin could provide a beneficial effect. Disease states that may be mentioned include sexual dysfunction, particularly premature ejaculation, preterm labour, complications in labour, appetite and feeding disorders, benign prostatic hyperplasia, premature birth, dysmenorrhoea, congestive heart failure, arterial hypertension, liver cirrhosis, nephrotic hypertension, occular hypertension, obsessive compulsive disorder and neuropsychiatric disorders.

Sexual dysfunction (SD) is a significant clinical problem which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman et al, *J. Urology*, 1999, 161, 5-11).

FSD can be defined as the difficulty or inability of a woman to find satisfaction in sexual expression. FSD is a collective term for several diverse female sexual disorders (Leiblum, S. R. (1998). Definition and classification of female sexual disorders. *Int. J. Impotence Res.*, 10, S104-S106; Berman, J. R., Berman, L. & Goldstein, I. (1999). Female sexual dysfunction: Incidence, pathophysiology, evaluations and treatment options. *Urology*, 54, 385-391). The woman may have lack of desire, difficulty with arousal or orgasm, pain with intercourse or a combination of these problems. Several types of disease, medications, injuries or psychological problems can cause FSD. Treatments in development are targeted to treat specific subtypes of FSD, predominantly desire and arousal disorders.

The categories of FSD are best defined by contrasting them to the phases of normal female sexual response: desire, arousal and orgasm (Leiblum, S. R. (1998). Definition and classification of female sexual disorders, *Int. J. Impotence Res.*, 10, S104-S106). Desire or libido is the drive for sexual expression. Its manifestations often include sexual thoughts either when in the company of an interested partner or when exposed to other erotic stimuli. Arousal is the vascular response to sexual stimulation, an important component of which is genital engorgement and includes increased vaginal lubrication, elongation of the vagina and increased genital sensation/sensitivity. Orgasm is the release of sexual tension that has culminated during arousal.

Hence, FSD occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders. Although the compounds of the invention will improve the genital response to sexual stimulation (as in female sexual arousal disorder), in doing so it may also improve the associated pain, distress and discomfort associated with intercourse and so treat other female sexual disorders.

Thus, in accordance with a further aspect of the invention, there is provided the use of a compound of the invention in the preparation of a medicament for the treatment or prophylaxis of hypoactive sexual desire disorder, sexual arousal disorder, orgasmic disorder and sexual pain disorder, more preferably for the treatment or prophylaxis of sexual arousal disorder, orgasmic disorder, and sexual pain disorder, and most preferably in the treatment or prophylaxis of sexual arousal disorder.

Hypoactive sexual desire disorder is present if a woman has no or little desire to be sexual, and has no or few sexual thoughts or fantasies. This type of FSD can be caused by low testosterone levels, due either to natural menopause or to surgical menopause. Other causes include illness, medications, fatigue, depression and anxiety.

Female sexual arousal disorder (FSAD) is characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants eg SSRIs or antihypertensive agents.

Sexual pain disorders (includes dyspareunia and vaginismus) is characterised by pain resulting from penetration and may be caused by medications which reduce lubrication, endometriosis, pelvic inflammatory disease, inflammatory bowel disease or urinary tract problems.

The prevalence of FSD is difficult to gauge because the term covers several types of problem, some of which are difficult to measure, and because the interest in treating FSD is relatively recent. Many women's sexual problems are associated either directly with the female ageing process or with chronic illnesses such as diabetes and hypertension.

Because FSD consists of several subtypes that express symptoms in separate phases of the sexual response cycle, there is not a single therapy. Current treatment of FSD focuses principally on psychological or relationship issues. Treatment of FSD is gradually evolving as more clinical and basic science studies are dedicated to the investigation of this medical problem. Female sexual complaints are not all psychological in pathophysiology, especially for those individuals who may have a component of vasculogenic dysfunction (eg FSAD) contributing to the overall female sexual complaint. There are at present no drugs licensed for the treatment of FSD. Empirical drug therapy includes oestrogen administration (topically or as hormone replacement therapy), androgens or mood-altering drugs such as buspirone or trazodone. These treatment options are often unsatisfactory due to low efficacy or unacceptable side effects.

The Diagnostic and Statistical Manual (DSM) IV of the American Psychiatric Association defines Female Sexual Arousal Disorder (FSAD) as being:

"a persistent or recurrent inability to attain or to maintain until completion of the sexual activity adequate lubrication-swelling response of sexual excitement. The disturbance must cause marked distress or interpersonal difficulty."

The arousal response consists of vasocongestion in the pelvis, vaginal lubrication and expansion and swelling of the external genitalia. The disturbance causes marked distress and/or interpersonal difficulty.

FSAD is a highly prevalent sexual disorder affecting pre-, peri- and post menopausal (±HRT) women. It is associated with concomitant disorders such as depression, cardiovascular diseases, diabetes and UG disorders.

The primary consequences of FSAD are lack of engorgement/swelling, lack of lubrication and lack of pleasurable genital sensation. The secondary consequences of FSAD are reduced sexual desire, pain during intercourse and difficulty in achieving an orgasm.

Male sexual dysfunction (MSD) is generally associated with either erectile dysfunction, also known as male erectile dysfunction (MED) and/or ejaculatory disorders such as premature ejaculation, anorgasmia (unable to achieve orgasm) or desire disorders such as hypoactive sexual desire disorder (lack of interest in sex).

PE is a relatively common sexual dysfunction in men. It has been defined in several different ways but the most widely accepted is the Diagnostic and Statistical Manual of Mental Disorders IV one which states:

"PE is a lifelong persistent or recurrent ejaculation with minimal sexual stimulation before, upon or shortly after penetration and before the patient wishes it. The clinician must take into account factors that affect duration of the excitement phase, such as age, novelty of the sexual partner or stimulation, and frequency of sexual activity. The disturbance causes marked distress of interpersonal difficulty."

The International Classification of Diseases 10 definition states:
"There is an inability to delay ejaculation sufficiently to enjoy lovemaking, manifest as either of the following: (1) occurrence of ejaculation before or very soon after the beginning of intercourse (if a time limit is required: before or within 15 seconds of the beginning of intercourse); (2) ejaculation occurs in the absence of sufficient erection to make intercourse possible. The problem is not the result of prolonged abstinence from sexual activity"

Other definitions which have been used include classification on the following criteria:
  Related to partner's orgasm
  Duration between penetration and ejaculation
  Number of thrust and capacity for voluntary control Psychological factors may be involved in PE, with relationship problems, anxiety, depression, prior sexual failure all playing a role.

Ejaculation is dependent on the sympathetic and parasympathetic nervous systems. Efferent impulses via the sympathetic nervous system to the vas deferens and the epididymis produce smooth muscle contraction, moving sperm into the posterior urethra. Similar contractions of the seminal vesicles, prostatic glands and the bulbouretheral glands increase the volume and fluid content of semen. Expulsion of semen is mediated by efferent impulses originating from a population of lumber spinothalamic cells in the lumbosacral spinal cord (Coolen & Truitt, *Science*, 2002, 297, 1566) which pass via the parasympathetic nervous system and cause rhythmic contractions of the bulbocavernous, ischiocavernous and pelvic floor muscles. Cortical control of ejaculation is still under debate in humans. In the rat the medial pre-optic area and the paraventricular nucleus of the hypothalamus seem to be involved in ejaculation.

Ejaculation comprises two separate components—emission and ejaculation. Emission is the deposition of seminal fluid and sperm from the distal epididymis, vas deferens, seminal vesicles and prostrate into the prostatic urethra. Subsequent to this deposition is the forcible expulsion of the seminal contents from the urethral meatus. Ejaculation is distinct from orgasm, which is purely a cerebral event. Often the two processes are coincidental.

A pulse of oxytocin in peripheral serum accompanies ejaculation in mammals. In man oxytocin but not vasopressin plasma concentrations are significantly raised at or around ejaculation. Oxytocin does not induce ejaculation itself; this process is 100% under nervous control via α1-adrenoceptor/sympathetic nerves originating from the lumbar region of the spinal cord. The systemic pulse of oxytocin may have a role in the peripheral ejaculatory response. It could serve to modulate the contraction of ducts and glandular lobules throughout the male genital tract, thus influencing the fluid volume of different ejaculate components for example. Oxytocin released centrally into the brain could influence sexual behaviour, subjective appreciation of arousal (orgasm) and latency to subsequent ejaculation.

Accordingly, one aspect of the invention provides for the use of a compound of formula (I), without the proviso, in the preparation of a medicament for the prevention or treatment of sexual dysfunction, preferably male sexual dysfunction, most preferably premature ejaculation.

It has been demonstrated in the scientific literature that the number of oxytocin receptors in the uterus increases during pregnancy, most markedly before the onset of labour (Gimp) & Fahrenholz, 2001, *Physiological Reviews*, 81 (2), 629-683.). Without being bound by any theory it is known that the inhibition of oxytocin can assist in preventing preterm labour and in resolving complications in labour.

Accordingly, another aspect of the invention provides for the use of a compound of formula (I), without the proviso, in the preparation of a medicament for the prevention or treatment of preterm labour and complications in labour.

Oxytocin has a role in feeding; it reduces the desire to eat (Arletti et al., *Peptides*, 1989, 10, 89). By inhibiting oxytocin it is possible to increase the desire to eat. Accordingly oxytocin inhibitors are useful in treating appetite and feeding disorders.

Accordingly, a further aspect of the invention provides for the use of a compound of formula (I), without the proviso, in the preparation of a medicament for the prevention or treatment of appetite and feeding disorders.

Oxytocin is implicated as one of the causes of benign prostatic hyperplasia (BPH). Analysis of prostate tissue have shown that patients with BPH have increased levels of oxytocin (Nicholson & Jenkin, *Adv. Exp. Med. & Biol.*, 1995, 395, 529). Oxytocin antagonists can help treat this condition.

Accordingly, another aspect of the invention provides for the use of a compound of formula (I), without the proviso, in the preparation of a medicament for the prevention or treatment of benign prostatic hyperplasia.

Oxytocin has a role in the causes of dysmenorrhoea due to its activity as a uterine vasoconstrictor (Akerlund, *Ann. NY Acad. Sci.*, 1994, 734, 47). Oxytocin antagonists can have a therapeutic effect on this condition.

Accordingly, a further aspect of the invention provides for the use of a compound of formula (I), without the proviso, in the preparation of a medicament for the prevention of treatment of dysmenorrhoea.

It is to be appreciated that all references herein to treatment include curative, palliative and prophylactic treatment.

The compounds of the present invention may be co-administered with one or more agents selected from:
1) One or more selective serotonin reuptake inhibitors (SSRIs) such as dapoxetine, paroxetine, 3-[(dimethylamino)methyl]-4-[4-(methylsulfanyl)phenoxy]benzenesulfonamide (Example 28, WO 0172687), 3-[(dimethylamino)methyl]-4-[3-methyl-4-(methylsulfanyl)phenoxy]benzenesulfonamide (Example 12, WO 0218333), N-methyl-N-({3-[3-methyl-4-(methylsulfanyl)phenoxy]-4-pyridinyl}methypamine (Example 38, PCT Application no PCT/1602/01032).
2) One or more local anaesthetics;
3) one or more α-adrenergic receptor antagonists (also known as α-adrenoceptor blockers, α-receptor blockers or α-blockers); suitable $\alpha_1$-adrenergic receptor antagonists include: phentolamine, prazosin, phentolamine mesylate, trazodone, alfuzosin, indoramin, naftopidil, tamsulosin, phenoxybenzamine, rauwolfa alkaloids, Recordati 15/2739, SNAP 1069, SNAP 5089, RS17053, SL 89.0591, doxazosin, Example 19 of WO9830560, terazosin and abanoquil; suitable $\alpha_2$-adrenergic receptor antagonists include dibenarnine, tolazoline, trimazosin, efaroxan, yohimbine, idazoxan clonidine and dibenarnine; suitable non-selective α-adrenergic receptor antagonists include dapiprazole; further α-adrenergic receptor antagonists are described in PCT application WO99/30697 published on 14 Jun. 1998 and U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference;

4) one or more cholesterol lowering agents such as statins (e.g. atorvastatin/Lipitor-trade mark) and fibrates;
5) one or more of a serotonin receptor agonist, antagonist or modulator, more particularly agonists, antagonists or modulators for example 5HT1A, 5HT2A, 5HT2C, 5HT3, 5HT6 and/or 5HT7 receptors, including those described in WO-09902159, WO-00002550 and/or WO-00028993;
6) one or more NEP inhibitors, preferably wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, sampatrilat) suitable NEP inhibitor compounds are described in EP-A-1097719; IC50 values against NEP and ACE may be determined using methods described in published patent application EP1097719-A1, paragraphs [0368] to [0376];
7) one or more of an antagonist or modulator for vasopressin receptors, such as relcovaptan (SR 49059), conivaptan, atosiban, VPA-985, CL-385004, Vasotocin.
8) Apomorphine—teachings on the use of apomorphine as a pharmaceutical may be found in U.S. Pat. No. 5,945,117;
9) Dopamine agonists (in particular selective D2, selective D3, selective D4 and selective D2-like agents) such as Pramipexole (Pharmacia Upjohn compound number PNU95666), ropinirole, apomorphine, surmanirole, quinelorane, PNU-142774, bromocriptine, carbergoline, Lisuride;
10) Melanocortin receptor agonists (e.g. Melanotan II and PT141) and selective MC3 and MC4 agonists (e.g. THIQ);
11) Mono amine transport inhibitors, such as Noradrenaline (norepinephrine) re-uptake inhibitors (NRIs), especially selective NRIs such as reboxetine, either in its racemic (R,R/S,S) or optically pure (S,S) enantiomeric form, particularly (S,S)-reboxetine, other Serotonin Re-uptake Inhibitors (SRIs) (e.g. paroxetine, dapoxetine) or Dopamine Re-uptake Inhibitors (DRIs);
12) 5-$HT_{1A}$ antagonists (e.g. robalzotan); and
13) PDE inhibitors such as PDE2 (e.g. erythro-9-(2-hydroxyl-3-nonyl)-adenine) and Example 100 of EP 0771799-incorporated herein by reference) and in particular a PDE5 inhibitor such as the pyrazolo [4,3-d]pyrimidin-7-ones disclosed in EP-A-0463756; the pyrazolo [4,3-d]pyrimidin-7-ones disclosed in EP-A-0526004; the pyrazolo [4,3-d]pyrimidin-7-ones disclosed in published international patent application WO 93/06104; the isomeric pyrazolo [3,4-d]pyrimidin-4-ones disclosed in published international patent application WO 93/07149; the quinazolin-4-ones disclosed in published international patent application WO 93/12095; the pyrido [3,2-d]pyrimidin-4-ones disclosed in published international patent application WO 94/05661; the purin-6-ones disclosed in published international patent application WO 94/00453; the pyrazolo [4,3-d]pyrimidin-7-ones disclosed in published international patent application WO 98/49166; the pyrazolo [4,3-d]pyrimidin-7-ones disclosed in published international patent application WO 99/54333; the pyrazolo [4,3-d]pyrimidin-4-ones disclosed in EP-A-0995751; the pyrazolo [4,3-d]pyrimidin-7-ones disclosed in published international patent application WO 00/24745; the pyrazolo [4,3-d]pyrimidin-4-ones disclosed in EP-A-0995750; the compounds disclosed in published international application WO95/19978; the compounds disclosed in published international application WO 99/24433 and the compounds disclosed in published international application WO 93/07124; the pyrazolo [4,3-d]pyrimidin-7-ones disclosed in published international application WO 01/27112; the pyrazolo [4,3-d]pyrimidin-7-ones disclosed in published international application WO 01/27113; the compounds disclosed in EP-A-1092718 and the compounds disclosed in EP-A-1092719.

Preferred PDE5 inhibitors for use with the invention:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756);

5-(2-ethoxy-5-morpholinoacetylphenyl)-1-methyl-3-n-propyl-1,6-dihydro-7H-pyrazolo[4,3-d]pyrimidin-7-one (see EP-A-0526004);

3-ethyl-5-[5-(4-ethylpiperazin-1-ylsulphonyl)-2-n-propoxyphenyl]-2-(pyridin-2-yl)methyl-2,6-dihydro-7H-pyrazolo [4,3-d]pyrimidin-7-one (see WO98/49166);

3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333);

(+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333);

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8);

5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15);

5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66);

5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124);

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132);

(6R,12aR)-2,3,6,7,12,12a-hexahydro-2-methyl-6-(3,4-methylenedioxyphenyl) pyrazino[2',1':6,1]pyrido[3,4-b]indole-1,4-dione (IC-351), i.e. the compound of examples 78 and 95 of published international application WO95/19978, as well as the compound of examples 1, 3, 7 and 8;

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; and the compound of example 11 of published international application WO93/07124 (EISAI); and compounds 3 and 14 from Rotella D P, *J. Med. Chem.*, 2000, 43, 1257.

Still further PDE5 inhibitors for use with the invention include:

4-bromo-5-(pyridylmethylamino)-6-[3-(4-chlorophenyl)-propoxy]-3(2H)pyridazinone; 1-[4-[(1,3-benzodioxol-5-ylmethyl)amiono]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)amino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer) and Sch-51866.

The contents of the published patent applications and journal articles and in particular the general formulae of the therapeutically active compounds of the claims and exemplified compounds therein are incorporated herein in their entirety by reference thereto.

More preferred PDE5 inhibitors for use with the invention are selected from the group:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil);

(6R,12aR)-2,3,6,7,12,12a-hexahydro-2-methyl-6-(3,4-methylenedioxyphenyl) pyrazino[2',1':6,1]pyrido[3,4-b]indole-1,4-dione (IC-351);

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); and 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one or 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one and pharmaceutically acceptable salts thereof.

A particularly preferred PDE5 inhibitor is 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) (also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine) and pharmaceutically acceptable salts thereof. Sildenafil citrate is a preferred salt.

Preferred agents for coadministration with the compounds of the present invention are PDE5 inhibitors, selective serotonin reuptake inhibitors (SSRIs), vasopressin $V_{1A}$ antagonists, α-adrenergic receptor antagonists, NEP inhibitors, dopamine agonists and melanocortin receptor agonists as described above. Particularly preferred agents for coadministration are PDE5 inhibitors, SSRIs, and $V_{1A}$ antagonists as described herein.

The compounds of the formula (I) can be administered alone but will generally be administered in admixture with a suitable pharmaceutical excipient, diluent or carrier selected with regard to the intended route of administration and standard pharmaceutical practice.

The present invention provides for a composition comprising a compound of formula (I) and a pharmaceutically acceptable diluent or carrier.

A suitable assay for determining the oxytocin antagonist activity of a compound is detailed herein below.

Oxytocin Receptor Beta-Lactamase Assay

Materials
Cell culture/Reagents
A: cell culture
Nutrient Mixture
F12 Ham's
Foetal Bovine Serum (FBS)
Geneticin
Zeocin
Trypsin/EDTA
PBS (phosphate buffered saline)
HEPES
B: reagents
Oxytocin
OT receptor-specific antagonist
Molecular grade Dimethyl Sulphoxide (DMSO)
Trypan Blue Solution 0.4%
CCF4-AM (Solution A)
Pluronic F127s (Solution B)
24% PEG, 18% TR40 (Solution C)
Probenecid (Dissolved at 200 mM in 200 mM NaOH, Solution D)
Methods:
Cell Culture: Cells used are CHO-OTR/NFAT-β-Lactamase. The NFAT-β-lactamase expression construct was transfected into the CHO-OTR cell line and clonal populations were isolated via fluorescence activated cell sorting (FACS). An appropriate clone was selected to develop the assay.
Growth Medium
90% F12 Nutrient Mix, 15 mM HEPES
10% FBS
400 μg/ml Geneticin
200 μg/ml Zeocin
2 mM L-Glutamine
Assay Media
99.5% F12 Nutrient Mix, 15 mM HEPES
0.5% FBS Recovery of cells—A vial of frozen cells is thawed rapidly in 37° C. water bath and the cell suspension transferred into a T225 flask with 50 ml of fresh growth medium and then incubated at 37° C., 5% $CO_2$ in an incubator until the cells adhered to the flask Replace media with 50 ml of fresh growth media the following day.

Culturing cells—CHO-OTR-NFAT-βLactamase cells were grown in growth medium. Cells were harvested when they reached 80-90% confluence removing the medium and washing with pre-warmed PBS. PBS was then removed and Trypsin/EDTA added (3 mls for T225 $cm^2$ flask) before incubating for 5 min in 37° C./5% $CO_2$ incubator. When cells were detached, pre-warmed growth media was added (7 mls for T225 $cm^2$ flask) and the cells re-suspended and mixed gently by pipetting to achieve single cell suspension. The cells were split into T225 flask at 1:10 (for 3 days growth) and 1:30 (for 5 days growth) ratio in 35 ml growth medium.

β-Lactamase Assay Method

Day 1: Cell Plate Preparation

Cells grown at 80-90% confluence were harvested and counted. Suspensions of cells at 2×105 cells/ml in growth medium were prepared and 30 μl of cells suspension added in 384-well, black clear-bottom plates. A blank plate containing diluents from each reagent was used for background subtraction.

Plates were incubated at 37° C., 5% $CO_2$ overnight.

Day 2: Cells Stimulation

10 μl antagonist/compound (diluted in assay media containing 1.25% DMSO=antagonist diluent) was added to appropriate wells and incubated for 15 minutes at 37° C., 5% $CO_2$ 10 μl oxytocin, made up in assay media, was added to all wells and incubated for 4 hours at 37° C., 5% $CO_2$.

A separate 384-well cell plate was used to generate an oxytocin dose response curve. (10 μl antagonist diluent was added to every well. 10 μl of oxytocin was then added. The cells are then treated as per antagonist/compound cell plates).

Preparation of 1 ml of 6× Loading Buffer with Enhanced Loading Protocol (this requires scale-up according to number of plates to be screened).

12 μl of solution A (1 mM CCF4-AM in Dry DMSO) was added to 60 μl of solution B (100 mg/ml Pluronic-F127 in DMSO+0.1% Acetic Acid) and vortexed.

The resulting solution was added to 9250 of solution C (24% w/w PEG400, 18% TR40 v/v in water).

75 μl of solution D was added (200 mM probenecid in 200 mM NaOH).

10 μl of 6× Loading Buffer was added to all wells and incubated for 1.5 hrs 2 hrs at room temperature in the dark.

The plates were read using an LJL Analyst, Excitation 405 nm, Emission 450 nm and 530 nm, gain optimal, lagtime 0.40 μs integration, 4 flashes, bottom reading.

Using the assay described above, the compounds of the present invention all exhibit oxytocin antagonist activity, expressed as a Ki value, of less than 1 μM. Preferred examples have Ki values of less than 200 nM and particularly preferred examples have Ki values of less than 50 nM. The compound of Example 48 has a Ki value of 1.8 nM. The compound of Example 43 has a Ki value of 4.2 nM. The compound of Example 25 has a Ki value of 9 nM. The compound of Example 28 has a Ki value of 13.8 nM.

The invention is illustrated by the following non-limiting examples in which the following abbreviations and definitions are used:

Arbocel® Filtration agent, from J. Rettenmaier & Sohne, Germany
 APCI+ Atmospheric Pressure Chemical Ionisation (positive scan)
 $CDCl_3$ Chloroform-di
 d Doublet
 dd Doublet of doublets
 DMSO Dimethylsulfoxide
 ES+ Electrospray ionisation positive scan.
 eq Equivalent
 $^1$H NMR Proton Nuclear Magnetic Resonance Spectroscopy
 HRMS High resolution mass spectrum
 LCMS Liquid chromatography-mass spectroscopy
 LRMS Low resolution mass spectrum
 MS (Low Resolution) Mass Spectroscopy
 m Multiplet
 PXRD Powder X-Ray Diffraction
 m/z Mass spectrum peak
 q Quartet
 s Singlet
 t Triplet
 δ Chemical shift Preparation 1: Azetidin-3-yl methanesulfonate hydrochloride

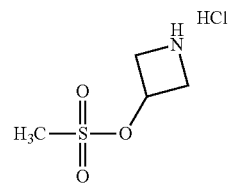

A mixture of 1-(diphenylmethyl)azetidin-3-yl methanesulfonate (WO 97/25322, p64), (20 g, 63 mmol) and chloroethylchloroformate (10 mL, 95 mmol) in dichloromethane (100 mL) was heated under reflux for 2.5 hours. The reaction mixture was then concentrated in vacuo and the residue was re-dissolved in methanol (100 mL) and heated under reflux for a further 2.5 hours. The mixture was then cooled to room temperature and concentrated in vacuo to afford the title compound as a white solid in quantitative yield, 9.6 g. $^1$H NMR (400 MHz, DMSO-$d_6$) δ: 3.28 (s, 3H), 4.06 (m, 2H), 4.31 (m, 2H), 5.34 (m, 1H)

Preparation 2: 1-{[(6-Methoxypyridin-3-yl)amino]carbonothioyl}azetidin-3-yl methanesulfonate

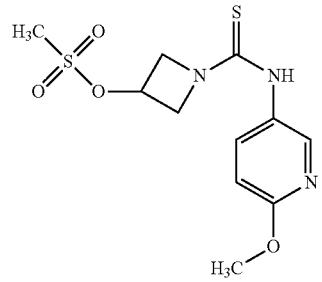 [SMILES: COc1ccc(NC(=S)N2CC(OS(C)(=O)=O)C2)cn1]

A solution of 5-amino-2-methoxypyridine (6.4 g, 51.5 mmol) in dichloromethane (20 mL) was added to an ice-cooled solution of 1'1-thiocarbonyldi-2(1H)-pyridone (12.05 g, 51.5 mmol) in dichloromethane (100 mL) and the mixture was stirred for 1 hour. The product of preparation 1 (9.6 g, 51.5 mmol) and triethylamine (7.24 mL, 51.5 mmol) were then added and the mixture was stirred for 18 hours. The reaction mixture was then filtered and the filtrate was washed with 10% citric acid, sodium hydrogen carbonate solution and brine. The organic solution was dried over magnesium sulfate, concentrated in vacuo and the residue was purified by column chromatography on silica gel, eluting with dichloromethane:methanol, 100:0 to 95:5, to afford the title compound as a pink solid in 29% yield, 4.7 g. $^1$H NMR (400 MHz, DMSO-$d_6$) δ: 2.48 (s, 3H), 3.82 (s, 3H), 4.17 (m, 2H), 4.48 (m, 2H), 5.35 (m, 1H), 6.78 (d, 1H), 7.73 (dd, 1H), 8.08 (d, 1H); LRMS APCI m/z 318 [M+H]$^+$

Preparation 3: Methyl N-(6-methoxypyridin-3-yl)-3-[(methylsulfonyl)oxy]azetidine-1-carbimidothioate

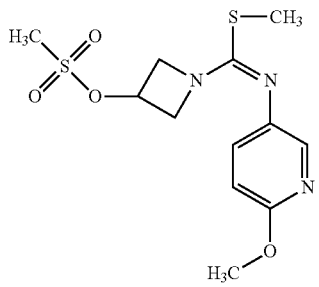 [SMILES: COc1ccc(/N=C(/SC)N2CC(OS(C)(=O)=O)C2)cn1]

Potassium tert-butoxide (1.8 g, 16.3 mmol) was added to a solution of the product of preparation 2 (4.3 g, 13.6 mmol) in tetrahydrofuran (100 mL) and the mixture was stirred at room temperature for 30 minutes. Methyl p-toluenesulfonate (3.63 g, 16.3 mmol) was then added and the mixture was stirred for 18 hours at room temperature. The reaction mixture was then diluted with water and brine and extracted with diethyl ether (2×50 mL). The combined organic solution was then dried over magnesium sulfate, concentrated in vacuo, and the residue was purified by column chromatography on silica gel, eluting with dichloromethane:methanol, 100:0 to 95:5, to afford the title compound the title compound as a red oil in 82% yield, 3.76 g. $^1$H NMR (400 MHz, CDCl$_3$) δ: 2.20 (s, 3H), 3.05 (s, 3H), 3.90 (s, 3H), 4.18 (m, 2H), 4.35 (m, 2H), 5.23 (m, 1H), 6.65 (d, 1H), 7.20 (dd, 1H), 7.75 (d, 1H); LRMS APCI m/z 332 [M+H]$^+$

Preparation 4: 1-[4-(6-Methoxypyridin-3-yl)-5-methyl-4H-1,2,4-triazol-3-yl]azetidin-3-yl methanesulfonate

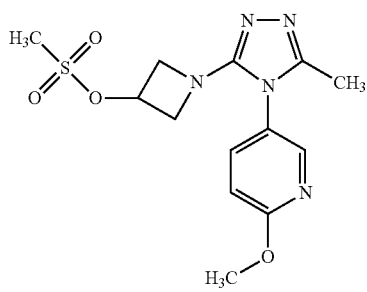

A mixture of the product of preparation 3 (1.5 g, 4.5 mmol), acethydrazide (671 mg, 9 mmol) and trifluoroacetic acid (3 drops, cat) in tetrahydrofuran (50 mL) was heated under reflux for 4 hours. The cooled mixture was then diluted with a mixture of water and brine, 30:70, and extracted with ethyl acetate (3×50 mL). The combined organic solution was dried over magnesium sulfate, concentrated in vacuo and the residue was purified by column chromatography on silica gel, eluting with dichloromethane:methanol, 100:0 to 97.5:2.5, to afford the title compound as a pale brown oil in 50% yield, 720 mg. $^1$H NMR (400 MHz, CDCl$_3$) δ: 2.24 (s, 3H), 3.04 (s, 3H), 4.02 (s, 3H), 4.14 (m, 2H), 4.37 (m, 2H), 5.30 (m, 1H), 6.91 (d, 1H), 7.72 (dd, 1H), 7.18 (d, 1H); LRMS APCI m/z 340 [M+H]$^+$

Preparation 5: 2-Methoxyacetylhydrazide

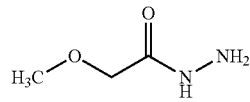

Hydrazine monohydrate (9.85 mL, 202 mmol) was added to a solution of methyl methoxyacetate (10 mL, 101 mmol) in methanol (50 mL) and the mixture was heated at 70° C. for 18 hours. The reaction mixture was then cooled to room temperature and concentrated in vacuo. The residue was azeotroped with toluene (×2) to give a white solid. The solid was triturated with diethyl ether and the resulting solid was dried under vacuum, at 50° C. for 30 minutes, to afford the title compound as a white solid in 95% yield, 9.98 g. $^1$H NMR (400 MHz, DMSO-d$_6$) δ: 3.26 (s, 3H), 3.79 (s, 2H), 4.22 (bs, 2H), 8.97 (bs, 1H)

Preparation 6: 1-[5-(Methoxymethyl)-4-(6-methoxypyridin-3-yl)-4H-1,2,4-triazol-3-yl]azetidin-3-vi methanesulfonate

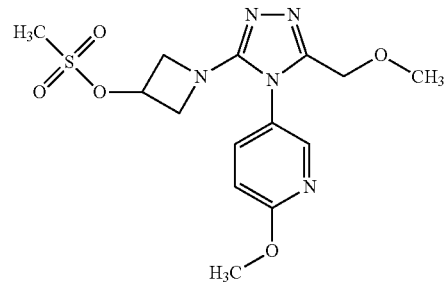

A mixture of the product of preparation 3 (1 g, 3 mmol), the product of preparation 5 (629 mg, 6 mmol) and trifluoroacetic acid (3 drops) in tetrahydrofuran (20 mL) was heated under reflux for 8 hours. The cooled mixture was then diluted with a mixture of water and brine, 30:70, and extracted with ethyl acetate (3×30 mL). The combined organic solution was dried over magnesium sulfate, concentrated in vacuo and the residue was purified by column chromatography on silica gel, eluting with dichloromethane:methanol, 100:0 to 95:5, to afford the title compound as a pale brown oil in 72% yield, 800 mg. $^1$H NMR (400 MHz, CDCl$_3$) δ: 3.03 (s, 3H), 3.27 (s, 3H), 3.98 (s, 3H), 4.06 (m, 2H), 4.20 (m, 2H), 4.32 (s, 2H), 5.23 (m, 1H), 6.84 (d, 1H), 7.60 (dd, 1H), 8.17 (d, 1H); LRMS APCI m/z 370 [M+H]$^+$ Preparation 7: 1-[5-Isopropyl-4-(6-methoxypyridin-3-yl)-4H-1,2,4-triazol-3-yl]azetidin-3-yl methanesulfonate

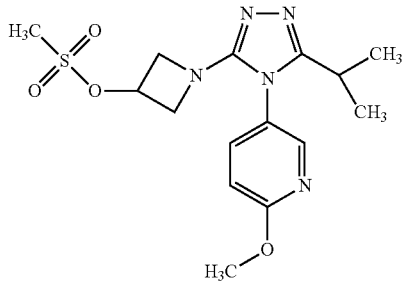 [SMILES: COc1ccc(-n2c(C(C)C)nnc2N2CC(OS(C)(=O)=O)C2)cn1]

The title compound was prepared from the product of preparation 3 and 2-methylpropanoic acid hydrazide (Bio-organic & Medicinal Chemistry, 2003, 11, 1381), using the same method as that described for preparation 6, in 30% yield. $^1$H NMR (400 MHz, CDCl$_3$) δ: 1.22 (d, 6H), 2.67 (m, 1H), 3.02 (s, 3H), 3.97 (m, 2H), 3.99 (s, 3H), 4.06 (m, 2H), 5.18 (m, 1H), 6.87 (d, 1H), 7.45 (dd, 1H), 8.08 (d, 1H); LRMS APCI m/z 368[M+H]$^+$ Preparation 8: 1-(Diphenylmethyl)-3-methylazetidin-3-ol

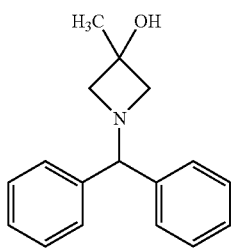 [SMILES: CC1(O)CN(C(c2ccccc2)c2ccccc2)C1]

Methyl magnesium iodide (3M in diethyl ether, 1.4 mL, 4.2 mmol) was added dropwise to an ice-cold solution of 1-(diphenylmethyl)-3-azetidinone (1 g, 4.20 mmol) in diethyl ether (25 mL) and the mixture was stirred for 1 hour at 0° C. The crude reaction mixture was then purified directly by column chromatography on silica gel, eluting with dichloromethane:methanol, 100:0 to 95:5, to afford the title compound the title compound as a pale yellow oil in 68% yield, 730 mg. $^1$H NMR (CDCl$_3$, 400 MHz) δ: 1.54 (s, 3H), 3.02 (m, 2H), 3.22 (m, 2H), 4.39 (s, 1H), 7.20 (m, 4H), 7.26 (m, 4H), 7.41 (m, 2H); LRMS ESI$^+$ m/z 254 [M+H]$^+$ Preparation 9: 1-(Diphenylmethyl)-3-(3-fluorophenoxy)-3-methylazetidine

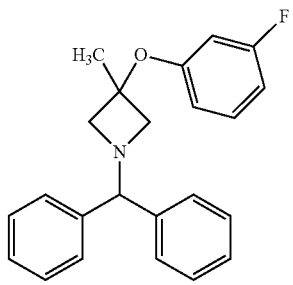 [SMILES: CC1(Oc2cccc(F)c2)CN(C(c2ccccc2)c2ccccc2)C1]

A mixture of 3-fluorophenol (0.2 mL, 2.2 mmol) and triphenylphosphine (648 mg, 2.5 mmol) in toluene (8 mL) was warmed to 95° C. A mixture of the product of preparation 8 (500 mg, 2 mmol) and di-isopropylazodicarboxylate (0.5 mL, 2.47 mmol) in toluene (4 mL) was then added and reaction mixture was stirred at 95° C. for 18 hours. The cooled reaction mixture was then concentrated in vacuo and the residue was purified by column chromatography on silica gel, eluting with dichloromethane:methanol, 95:5, to afford the title compound as a yellow oil in 93% yield. $^1$H NMR (CDCl$_3$, 400 MHz) δ: 1.77 (s, 3H), 3.25 (m, 2H), 3.50 (m, 2H), 4.45 (s, 1H), 6.40 (d, 1H), 6.46 (d, 1H), 6.63 (t, 1H), 6.98 (m, 1H), 7.19 (m, 4H), 7.32 (m, 4H), 7.48 (m, 2H); LRMS APCI$^+$ m/z 348 [M+H]$^+$ Preparation 10: 3-(3-Fluorophenoxy)-3-methylazetidine hydrochloride

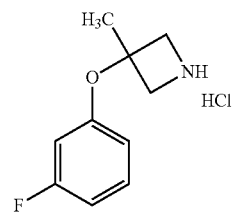

1-Chloroethyl chloroformate (0.3 mL, 2.76 mmol) was added to an ice-cooled solution of the product of preparation 9 (1.34 g, 4.43 mmol) in dichloromethane (10 mL) and mixture was heated under reflux for 3 hours. The reaction mixture was then concentrated in vacuo and the residue was re-dissolved in methanol. This solution was then heated under reflux for 3 hours. The reaction mixture was then cooled, concentrated in vacuo and the residue was purified by column chromatography on silica gel, eluting with dichloromethane:methanol, 95:5, to afford the title compound as a crystalline solid in 60% yield, 200 mg.

$^1$H NMR (DMSO-d$_6$, 400 MHz) δ: 3.35 (s, 3H), 4.18 (m, 4H), 6.65 (m, 2H), 6.84 (t, 1H), 7.35 (m, 1H); LRMS ESI$^+$ m/z 182 [M+H]$^+$

Preparation 11: 3-(3-Fluorophenoxy)-N-(6-methoxypyridin-3-yl)-3-methylazetidine-1-carbothioamide

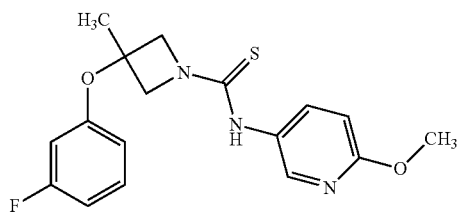 [SMILES: COc1ccc(NC(=S)N2CC(C)(Oc3cccc(F)c3)C2)cn1]

5-Isothiocyanato-2-methoxypyridine [(172.9 mg, 1.04 mmol), *J. Org. Chem.* (1980), 45, 4219] was added to a solution of the product of preparation 10 (200 mg, 1.04 mmol) in dichloromethane (3 mL) and the mixture was stirred at room temperature for 18 hours. The reaction mixture was concentrated in vacuo to afford the crude title compound in quantitative yield. This material was used in further reactions without any purification. $^1$H NMR (DMSO-$d_6$, 400 MHz) δ: 1.77 (s, 3H), 4.04 (s, 3H), 4.33 (m, 2H), 4.50 (m, 2H), 6.50 (m, 2H), 6.74 (m, 2H), 7.23 (m, 1H), 7.44 (dd, 1H), 8.10 (m, 1H); LRMS ESI$^+$ m/z 348 [M+H]$^+$

Preparation 12: Methyl 3-(3-fluorophenoxy)-N-(6-methoxypyridin-3-yl)-3-methylazetidine-1-carbimidothioate

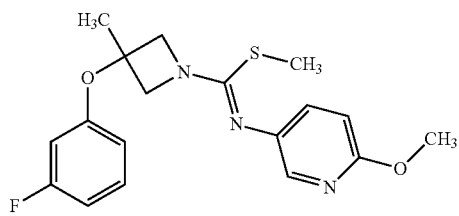 [SMILES: COc1ccc(/N=C(\SC)N2CC(C)(Oc3cccc(F)c3)C2)cn1]

The title compound was prepared from the product of preparation 11, using the same method as that described for preparation 3, as a pale yellow oil in 46% yield. $^1$H NMR (CDCl$_3$, 400 MHz) δ: 1.78 (s, 3H), 2.36 (s, 3H), 3.97 (s, 3H), 4.30 (m, 2H), 4.58 (m, 2H), 6.43 (m, 2H), 6.75 (m, 2H), 7.17 (d, 1H), 7.24 (m, 1H), 7.78 (d, 1H); LRMS ESI$^+$ m/z 362 [M+H]$^+$

Preparation 13: 3-Isothiocyanato-6-methoxy-2-methylpyridine

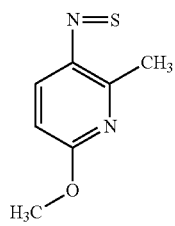

A solution of 6-methoxy-2-methyl-3-pyridylamine [(500 mg, 3.6 mmol), WO 04/062665, p46] in dichloromethane (10 mL) was added to an ice-cold solution of 1'1-thiocarbonyldi-2(1H)-pyridone (840 mg, 3.6 mmol) in dichloromethane (10 mL) and the mixture was stirred for 18 hours. The reaction mixture was then concentrated in vacuo and the residue was purified by column chromatography on silica gel, eluting with dichloromethane to afford the title compound as a yellow solid in 79% yield. $^1$H NMR (CDCl$_3$, 400 MHz) δ: 2.52 (s, 3H), 3.92 (s, 3H), 6.56 (d, 1H), 7.38 (d, 1H); LRMS ESI$^+$ m/z 181 [M+H]$^+$

Preparation 14: 1-{[(6-Methoxy-2-methylpyridin-3-yl)amino]carbonothioyl}azetidin-3-vi methanesulfonate

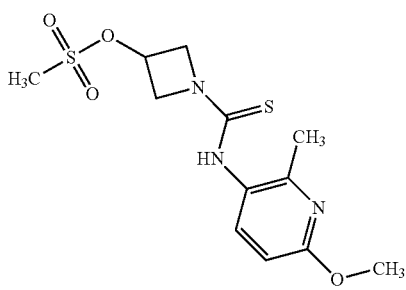

A mixture of the product of preparation 1 (535 mg, 2.84 mmol), preparation 13 (515 mg, 2.84 mmol) and triethylamine (0.4 mL, 2.84 mmol) in dichloromethane was stirred for at room temperature for 18 hours. The reaction mixture was then filtered and the residue was partitioned between ethyl acetate and brine. The combined organic solution was dried over magnesium sulfate and concentrated in vacuo to afford the title compound as a pale yellow solid in 71% yield, 670 mg. $^1$H NMR (CDCl$_3$, 400 MHz) δ: 2.44 (s, 3H), 3.08 (s, 3H), 3.95 (s, 3H), 4.20 (m, 2H), 4.40 (m, 2H), 5.20 (m, 1H), 6.62 (d, 1H), 7.49 (d, 1H); LRMS ESI$^+$ m/z 332 [M+H]$^+$

Preparation 15: Methyl N-(6-methoxy-2-methylpyridin-3-yl)-3-[(methylsulfonyl)oxy]azetidine-1-carbimidothioate

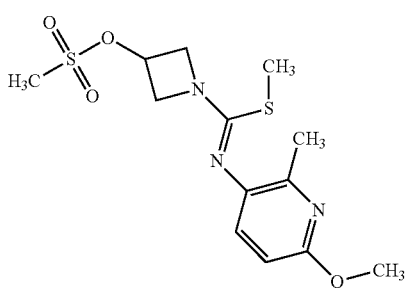

The title compound was prepared from the product of preparation 14 using the same method as that described for preparation 3, as a brown oil in 98% yield.
$^1$H NMR (CDCl$_3$, 400 MHz) δ: 2.34 (s, 3H), 2.46 (s, 3H), 3.06 (s, 3H), 3.90 (s, 3H), 4.16 (m, 2H), 4.30 (m, 2H), 5.20 (m, 1H), 6.53 (d, 1H), 7.10 (d, 1H); LRMS ESI$^+$ m/z 346 [M+H]$^+$

Preparation 16: 1-[4-(6-Methoxy-2-methylpyridin-3-yl)-5-methyl-4H-1,2,4-triazol-3-yl]azetidin-3-yl methanesulfonate

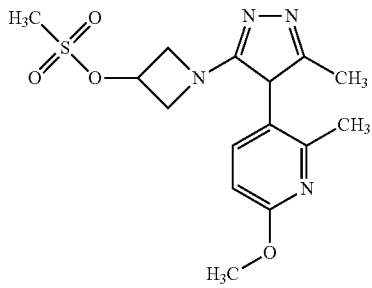

The title compound was prepared from the product of preparation 15 and acethydrazide, using the same method as that described for preparation 4, in 35% yield. $^1$H NMR (CDCl$_3$, 400 MHz) δ: 2.12 (s, 3H), 2.22 (s, 3H), 3.06 (s, 3H), 3.95 (s, 3H), 4.03 (m, 2H), 4.10 (m, 2H), 5.20 (m, 1H), 6.70 (d, 1H), 7.37 (d, 1H); LRMS ESI$^+$ m/z 346 [M+H]$^+$

Preparation 17: Piperidin-4-yl acetate

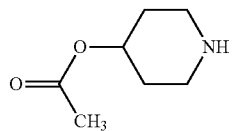

10% Pd/C (500 mg) was added to a solution of 1-benzylpiperidin-4-yl acetate [(11 g, 47 mmol), *J. Org. Chem.* 68(2), 613-616; 2003] in a mixture of ethanol and water (90:10, 110 mL), and the mixture was stirred at 60° C., under 60 psi of hydrogen gas for 18 hours. The reaction mixture was then filtered through Arbocel®, washing through with ethanol, and the filtrate was concentrated in vacuo to afford the title product in 92% yield, 7.2 g.

$^1$H NMR (CDCl$_3$, 400 MHz) δ: 1.60 (m, 2H), 1.81-2.18 (m, 5H), 2.78 (m, 2H), 2.95-3.18 (m, 2H), 4.82 (m, 1H); LRMS APCI$^+$ m/z 145 [M+H]$^+$

Preparation 18: 1-{[(6-Methoxypyridin-3-yl)amino]carbonothioyl}piperidin-4-yl acetate

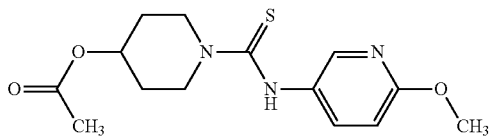

The title compound was prepared from 5-amino-2-methoxypyridine, 1'1-thiocarbonyldi-2(1H)-pyridone and the product of preparation 17, using the same method as that described for preparation 2, in 19% yield. $^1$H NMR (CDCl$_3$, 400 MHz) δ: 1.78-1.85 (m, 2H), 1.98-2.08 (m, 2H), 2.18 (s, 3H), 3.79-3.87 (m, 2H), 3.95 (s, 3H), 4.02-4.12 (m, 2H), 5.01-5.09 (m, 1H), 6.89 (d, 1H), 6.99 (s, 1H), 7.58 (d, 1H), 7.97 (s, 1H); LRMS APCI m/z 310 [M+H]$^+$

Preparation 19: 4-Hydroxy-N-(6-methoxypyridin-3-yl)piperidine-1-carbothioamide

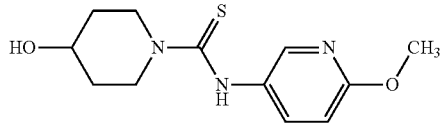 [SMILES: COc1ccc(NC(=S)N2CCC(O)CC2)cn1]

The title compound was prepared from piperidin-4-ol, 5-amino-2-methoxypyridine, and 1'1-thiocarbonyldi-2(1H)-pyridone, using the same method as that described for preparation 2, in 67% yield. $^1$H NMR (400 MHz, CDCl$_3$) δ: 1.59-1.79 (m, 2H), 1.90-2.04 (m, 2H), 3.64-3.76 (m, 2H), 3.93 (s, 3H), 4.00-4.10 (m, 1H), 4.14-4.22 (m, 1H), 6.78 (d, 1H), 7.04-7.20 (s, 1H), 7.62 (d, 1H), 7.98 (s, 1H) LRMS APCI m/z 268 [M+H]$^+$

Preparation 20: 1-[4-(6-Methoxypyridin-3-yl)-5-methyl-4H-1,2,4-triazol-3-yl]piperidin-4-yl acetate

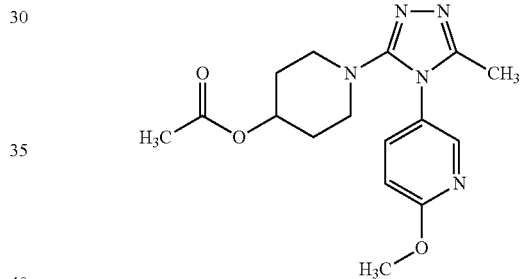

Potassium tert-butoxide (0.91 g, 8.10 mmol) was added to a solution of the product of preparation 18 (2.28 g, 7.36 mmol) in tetrahydrofuran (20 mL) and the mixture was stirred at room temperature for 30 minutes. Methyl p-toluenesulfonate (1.81 g, 8.10 mmol) was added and the mixture was stirred for 18 hours. The reaction mixture was then concentrated in vacuo and the residue was re-dissolved in dichloromethane. The solution was washed with sodium hydrogen carbonate solution and brine, dried over magnesium sulfate and concentrated in vacuo to give an oil. The oil was dissolved in tetrahydrofuran (5 mL), trifluoroacetic acid (0.28 mL, 3.68 mmol) and acethydrazide (1.09 g, 14.7 mmol) were added and the mixture was heated under reflux for 18 hours. The cooled reaction mixture was then concentrated in vacuo and the residue was dissolved in dichloromethane and washed with sodium hydrogen carbonate solution and brine. The organic solution was dried over magnesium sulfate and concentrated in vacuo to afford the title compound as an oil in 49% yield, 1.2 g.

$^1$H NMR (CDCl$_3$, 400 MHz) δ: 1.57-1.70 (m, 2H), 1.79-1.90 (m, 2H), 2.01 (s, 3H), 2.22 (s, 3H), 2.94-3.01 (m, 2H), 3.22-3.31 (m, 2H), 3.99 (s, 3H), 4.80-4.92 (m, 1H), 6.89 (d, 1H), 7.52 (d, 1H), 8.12 (s, 1H)

Preparation 21: 1-[4-(6-Methoxypyridin-3-yl)-5-methyl-4H-1,2,4-triazol-3-yl]piperidin-4-ol

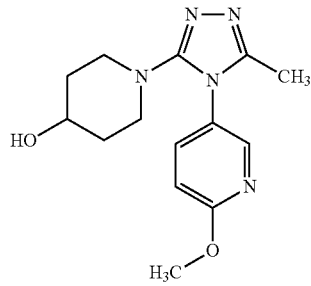 [SMILES: COc1ccc(-n2c(C)nnc2N2CCC(O)CC2)cn1]

A mixture of the product of preparation 20 (1.2 g, 3.62 mmol) and 1M potassium carbonate solution (10 mL, 10 mmol) in methanol (20 mL) was stirred at room temperature for 24 hours. The reaction mixture was then concentrated in vacuo and the aqueous residue was extracted with dichloromethane. The organic solution was washed with brine, dried over sodium sulfate and concentrated in vacuo. Purification by column chromatography on silica gel, eluting with dichloromethane:methanol, 100:0 to 90:10, to afford the title compound as a solid in 45% yield, 472.5 mg. $^1$H NMR (CDCl$_3$, 400 MHz) δ: 1.41-1.55 (m, 2H), 1.71 (s, 1H), 1.80-1.90 (m, 2H), 2.22 (s, 3H), 2.85-2.94 (m, 2H), 3.22-3.31 (m, 2H), 3.77-3.82 (m, 1H), 3.99 (s, 3H), 6.89 (d, 1H), 7.52 (d, 1H), 8.12 (s, 1H); LRMS APCI m/z 332 [M+H]$^+$ Preparation 22: 3-[(1-Benzylpiperidin-4-yl)oxy]-2-methylpyridine

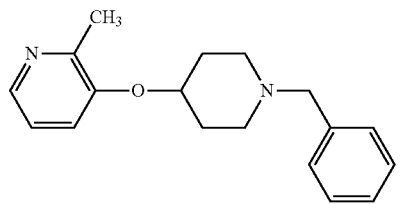 [SMILES: Cc1ncccc1OC1CCN(Cc2ccccc2)CC1]

1-Benzyl-4-hydroxypiperidine (1.5 g, 7.8 mmol) and 3-hydroxy-2-methylpyridine (1.75 g, 16 mmol) were added to mixture of polymer supported triphenylphosphine (1 g, 3 mmol) and di-tert-butyl azodicarboxylate (3.61 g, 16 mmol) in dichloromethane (10 mL) and the mixture was stirred at room temperature for 3 hours. Trifluoroacetic acid (16 mL) was then added and the mixture was stirred for a further hour then concentrated in vacuo. The residue was suspended in dichloromethane and basified with 2M sodium hydroxide solution (5 mL). The organic layer was separated, washed with brine, dried over magnesium sulfate and concentrated in vacuo. Purification of the residue by column chromatography on silica gel, eluting with dichloromethane:methanol: 0.88 ammonia, 90:10:1, to afford the title compound as a liquid in 51% yield, 1.12 g. $^1$H NMR (CDCl$_3$, 400 MHz) δ: 1.79-1.88 (m, 2H), 1.90-2.01 (m, 2H), 2.25-2.41 (m, 2H), 2.44 (s, 3H), 2.64-2.78 (m, 2H), 3.53 (s, 2H), 4.28-4.39 (m, 1H), 7.00-7.09 (m, 2H), 7.19-7.38 (m, 5H), 8.14 (m, 1H); LRMS APCI m/z 283 [M+H]$^+$ Preparation 23: 2-Methyl-3-(piperidin-4-yloxy)pyridine

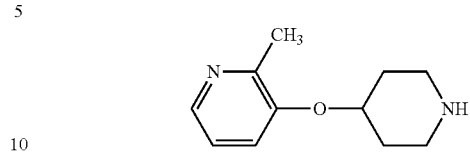

10% Pd/C (100 mg, cat) was added to a solution of the product of preparation 22 (1.12 g, 3.96 mmol) in a mixture of ethanol and water (90:10, 11 mL) and the mixture was stirred at 60° C., under 60 psi of hydrogen gas for 18 hours. The reaction mixture was then filtered through Arbocel®, and the filtrate was concentrated in vacuo. The residue was re-dissolved in ethanol/water (90:10, 11 mL) and 10% Pd/C (100 mg, cat) was added. The reaction mixture was then stirred at 60° C., under 60 psi of hydrogen gas. After 18 hours, the mixture was filtered through Arbocel®, washing through with ethanol, and the filtrate was concentrated in vacuo. Trituration of the residue with diethyl ether afforded the title compound as a solid in 74% yield, 565 mg. $^1$H NMR (CDCl$_3$, 400 MHz) δ: 2.10-2.20 (m, 2H), 2.30-2.41 (m, 2H), 2.49 (s, 3H), 3.29-3.40 (m, 4H), 4.61-4.70 (m, 1H), 7.02-7.13 (m, 2H), 8.12 (m, 1H); LRMS APCI$^+$ m/z 193 [M+H]$^+$ Preparation 24: N-(6-Methoxypyridin-3-yl)-4-[(2-methylpyridin-3-yl)oxy]piperidine-1-carbothioamide

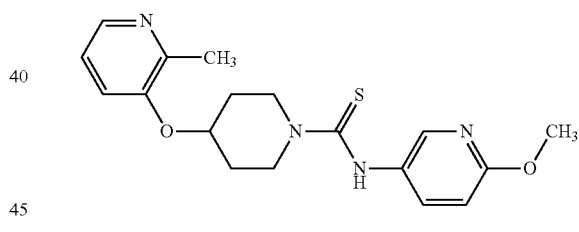

5-Isothiocyanato-2-methoxypyridine [(172.9 mg, 1.04 mmol), J. Org. Chem. (1980), 45, 4219] was added to a solution of the product of preparation 23 (200 mg, 1.04 mmol) in dichloromethane (3 mL) and the mixture was stirred at room temperature for 72 hours. The resulting precipitate was filtered off, washing through with water, dichloromethane and diethyl ether, to afford a portion of the title compound. The filtrate was then diluted with water and acidified with 10% citric acid. The aqueous layer was separated, basified with sodium hydrogen carbonate solution and extracted with dichloromethane. The organic layer was washed with brine, dried over sodium sulfate and concentrated in vacuo to afford further title compound as a white solid. The two solids were combined to give 48% overall yield (180 mg). $^1$H NMR (DMSO-d$_6$, 400 MHz) δ: 1.69-1.81 (m, 2H), 1.95-2.09 (m, 2H), 2.48 (s, 3H), 3.83 (s, 3H), 3.87-3.98 (m, 2H), 4.05-4.19 (m, 2H), 4.83-4.90 (m, 1H), 7.44-7.51 (m, 1H), 7.56-7.62 (m, 1H), 7.79-7.85 (m, 1H), 7.93 (s, 1H), 8.19 (d, 1H), 9.32 (s, 1H); LRMS APCI m/z 359 [M+H]$^+$

Preparation 25: 2-[(1-Benzylpiperidin-4-yl)oxy]-3-methylpyridine

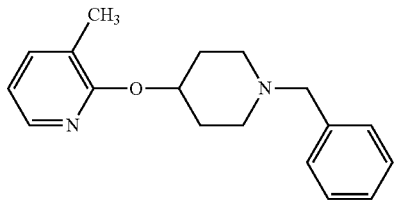 [SMILES: Cc1cccnc1OC1CCN(Cc2ccccc2)CC1]

Potassium tert-butoxide (1.08 g, 8.62 mmol) was added to a solution of 1-benzyl-4-hydroxypiperidine (1.5 g, 7.84 mmol) in dimethylsulfoxide (5 mL) and the mixture was stirred at room temperature for 1 hour. 2-Fluoro-3-methylpyridine (957 mg, 8.62 mmol) was then added and the reaction mixture was stirred at room temperature for 3 hours. The mixture was partitioned between ethyl acetate and water, and the organic layer was separated and washed with sodium hydrogen carbonate solution and brine. The organic solution was then dried over magnesium sulfate concentrated in vacuo and the residue was purified by column chromatography on silica gel, eluting with dichloromethane:methanol, 100:0 to 70:30, to afford the title compound as a solid in 85% yield, 1.9 g. $^1$H NMR (CDCl$_3$, 400 MHz): 1.79-1.94 (m, 2H), 1.98-2.09 (m, 2H), 2.17 (s, 3H), 2.37-2.47 (m, 2H), 2.68-2.77 (m, 2H), 3.61-3.51 (bs, 2H), 5.12-5.20 (m, 1H), 6.74 (m, 1H), 7.24-7.37 (m, 6H), 7.95 (m, 1H); LRMS APCI m/z 283 [M+H]$^+$

Preparation 26: 4-[(1-Benzylpiperidin-4-yl)oxy]pyridine

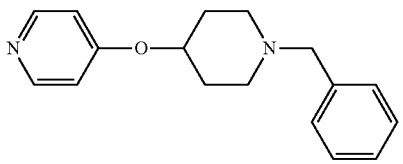 [SMILES: c1ccc(CN2CCC(Oc3ccncc3)CC2)cc1]

The title compound was prepared from 1-benzyl-4-hydroxypiperidine and 4-chloropyridine (979 mg, 8.62 mmol), using the same method as that described for preparation 25, as an oil in 52% yield. $^1$H NMR (CDCl$_3$, 400 MHz): 1.81-1.96 (m, 2H), 1.98-2.18 (m, 2H), 2.30-2.48 (m, 2H), 2.70-2.83 (m, 2H), 3.52-3.70 (m, 2H), 4.40-4.50 (m, 1H), 6.72-6.80 (m, 2H), 7.22-7.39 (m, 5H), 8.40 (m, 2H); LRMS APCI m/z 269 [M+H]$^+$

Preparation 27: tert-butyl 4-[(2,3-dimethylpyridin-4-yl)oxy]piperidine-1-carboxylate

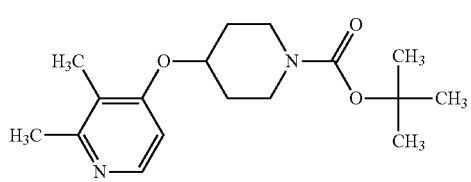 [SMILES: Cc1nccc(OC2CCN(C(=O)OC(C)(C)C)CC2)c1C]

Potassium tert-butoxide (4.70 g, 42 mmol) was added to a solution of 1-Boc-4-hydroxypiperidine (4.05 g, 20.1 mmol) in dimethylsulfoxide (20 mL) and the mixture was stirred at room temperature for 1 hour. 4-Chloro-2,3-dimethylpyridine (3.58 g, 20.1 mmol) was then added and the reaction mixture was stirred at 50° C. for 18 hours. The mixture was partitioned between ethyl acetate and water, and the organic layer was separated and washed with sodium hydrogen carbonate solution and brine. The organic solution was then dried over magnesium sulfate concentrated in vacuo and the residue was purified by column chromatography on silica gel, eluting with dichloromethane:methanol: 0.88 ammonia, 100:0:0 to 94:6:0.6, to afford the title compound as an oil in 39% yield, 2.4 g.
$^1$H NMR (CDCl$_3$, 400 MHz) δ: 1.44 (s, 9H), 1.75-1.85 (m, 2H), 1.87-1.95 (m, 2H), 2.15 (s, 3H), 2.50 (s, 3H), 3.42-3.53 (m, 2H), 3.56-3.65 (m, 2H), 4.57-4.62 (m, 1H), 6.64 (d, 1H), 8.21 (d, 1H); LRMS APCI m/z 307 [M+H]$^+$

Preparation 28: tert-Butyl 4-[(3-methylpyridin-4-yl)oxy]piperidine-1-carboxylate

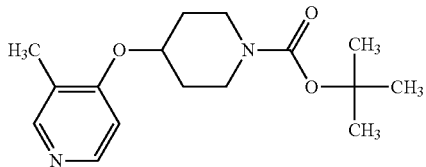 [SMILES: Cc1cnccc1OC1CCN(C(=O)OC(C)(C)C)CC1]

The title compound was prepared from 1-Boc-4-hydroxypiperidine and 4-chloro-3-methylpyridine hydrochloride, using a similar method to preparation 27. The reaction mixture was stirred for 72 hours to afford the title compound the desired product in 87% yield. $^1$H NMR(CDCl$_3$, 400 MHz) δ: 1.44 (s, 9H), 1.75-1.85 (m, 2H), 1.87-1.97 (m, 2H), 2.18 (s, 3H), 3.42-3.53 (m, 2H), 3.56-3.65 (m, 2H), 4.57-4.65 (m, 1H), 6.72 (d, 1H), 8.29 (s, 1H), 8.35 (d, 1H); LRMS APCI m/z 293 [M+H]$^+$

Preparation 29: 3-Methyl-2-(piperidin-4-yloxy)pyridine

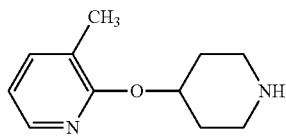

The title compound was prepared from the product of preparation 25, using the same method as that of preparation 17, as a gum in 62% yield. $^1$H NMR (CDCl$_3$, 400 MHz) δ: 1.79-1.94 (m, 2H), 1.96-2.20 (m, 5H), 2.89-3.00 (m, 2H), 3.18-3.26 (m, 2H), 5.24-5.35 (m, 1H), 6.74 (m, 1H), 7.38 (m, 1H), 7.95 (m, 1H); LRMS APCI m/z 193 [M+H]$^+$

Preparation 30: 4-(Piperidin-4-yloxy)pyridine

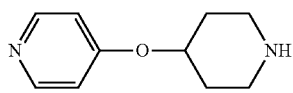 [SMILES: c1cc(OC2CCNCC2)ccn1]

The title compound was prepared from the product of preparation 26, using the same method as that described for preparation 23, as a solid in 82% yield.
¹H NMR (CDCl₃, 400 MHz) δ: 1.94-2.02 (m, 2H), 2.20-2.29 (m, 2H), 3.06-3.18 (m, 2H), 3.22-3.32 (m, 2H), 4.60-4.67 (m, 1H), 6.80 (d, 2H), 8.43 (d, 2H); LRMS APCI⁺ m/z 179 [M+H]⁺

Preparation 31:
2,3-Dimethyl-4-(piperidin-4-yloxy)pyridine dihydrochloride

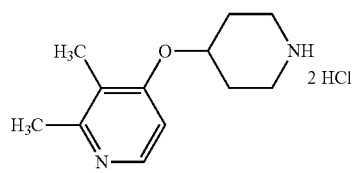

A solution of the product of preparation 27 (1.3 g, 4.24 mmol) in hydrochloric acid (4M in dioxan, 5 mL) was stirred for 2 hours at room temperature. The reaction mixture was then concentrated in vacuo and the residue as azeotroped with toluene to afford the title compound as a white solid in 91% yield, 800 mg. ¹H NMR (DMSO-d₆, 400 MHz) δ: 1.91-2.02 (m, 2H), 2.15-2.24 (m, 5H), 2.48 (s, 3H), 3.09-3.17 (m, 2H), 3.18-3.24 (m, 2H), 5.09-5.15 (m, 1H), 7.59 (d, 1H), 8.58 (d, 1H), 9.19-9.38 (m, 2H); LRMS APCI⁺ m/z 207 [M+H]⁺

Preparation 32:
3-Methyl-4-(piperidin-4-yloxy)pyridine dihydrochloride

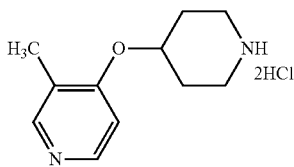

The title compound was prepared from the product of preparation 28, using the same method as that described for 31, as a white solid in 82% yield. ¹H NMR (DMSO-d₆, 400 MHz): 1.92-2.05 (m, 2H), 2.16-2.24 (m, 5H), 3.11-3.19 (m, 4H), 5.15-5.17 (m, 1H), 7.73 (d, 1H), 8.64 (s, 1H), 8.72 (m, 1H), 9.39-9.57 (m, 2H); LRMS APCI⁺ m/z 193 [M+H]⁺

Preparation 33: N-(6-Methoxypyridin-3-yl)-4-[(3-methylpyridin-2-yl)oxy]piperidine-1-carbothioamide

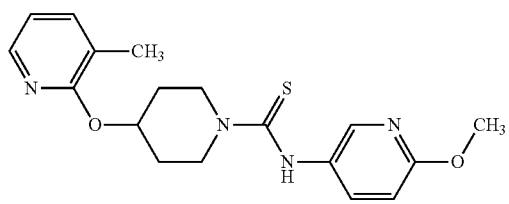 [SMILES: COc1ccc(NC(=S)N2CCC(Oc3ncccc3C)CC2)cn1]

The title compound was prepared from the product of preparation 29 and 5-isothiocyanato-2-methoxypyridine (*J. Org. Chem.* (1980), 45, 4219), using a similar method to that of preparation 24. Tlc analysis showed the reaction to be complete after 18 hours (c.f. 72 hours in preparation 24), affording the desired product as a solid in 58% yield. ¹H NMR (CDCl₃, 400 MHz): 1.93-2.00 (m, 2H), 2.05-2.18 (m, 2H), 2.20 (s, 3H), 3.95 (s, 3H), 4.02-4.09 (m, 4H), 5.40-5.45 (m, 1H), 6.72-6.81 (m, 2H), 7.01 (bs, 1H), 7.40 (m, 1H), 7.59 (m, 1H), 7.95-7.99 (m, 2H); LRMS APCI m/z 359 [M+H]⁺

Preparation 34: N-(6-Methoxypyridin-3-yl)-4-(pyridin-4-yloxy)piperidine-1-carbothioamide

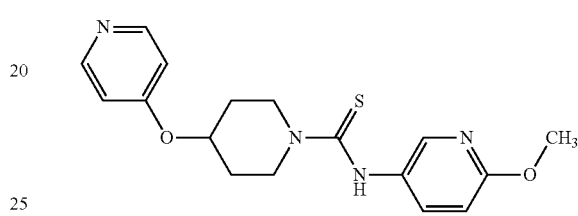

5-Isothiocyanato-2-methoxypyridine [(829 mg, 4.99 mmol), *J. Org. Chem.* (1980), 45, 4219] was added to a solution of the product of preparation 30 (890 mg, 4.99 mmol) in dichloromethane (10 mL) and the mixture was stirred at room temperature for 20 hours. The resulting precipitate was filtered off, washing through with diethyl ether, to afford the title compound as a white solid in 43% yield, 738 mg. ¹H NMR (CDCl₃, 400 MHz) δ: 1.95-2.05 (m, 2H), 2.06-2.15 (m, 2H), 3.93-4.01 (m, 5H), 4.03-4.12 (m, 2H), 4.72-4.79 (m, 1H), 6.75-6.85 (m, 3H), 7.12 (m, 1H), 7.58 (m, 1H), 7.98 (m, 1H), 8.40-8.44 (m, 2H); LRMS APCI m/z 345 [M+H]⁺

Preparation 35: N-(6-Methoxypyridin-3-yl)-4-(2-methylphenoxy)piperidine-1-carbothioamide

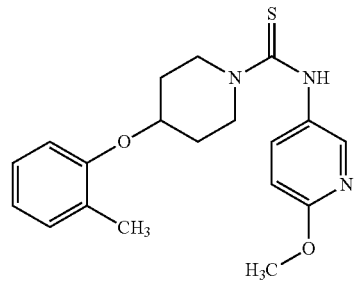 [SMILES: COc1ccc(NC(=S)N2CCC(Oc3ccccc3C)CC2)cn1]

5-Isothiocyanato-2-methoxypyridine [(829 mg, 4.99 mmol), *J. Org. Chem.* (1980), 45, 4219] was added to a solution of 4-(2-methylphenoxy)-piperidine hydrochloride [(990 mg, 4.3 mmol), *J. Med. Chem.* (1978), 21, 309] and N,N-diisopropylethylamine (0.79 mL, 4.7 mmol) in dichloromethane (10 mL) and the mixture was stirred for 3 hours at room temperature. The organic solution was then diluted with dichloromethane and washed with sodium hydrogen carbonate solution and brine. The organic solution was dried over magnesium sulfate and concentrated in vacuo. Tritu-

Preparation 36: 4-[(2,3-Dimethylpyridin-4-yl)oxy]-N-(6-methoxypyridin-3-yl)piperidine-1-carbothioamide

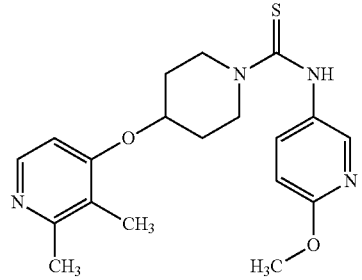 [SMILES: COc1ccc(NC(=S)N2CCC(Oc3ccnc(C)c3C)CC2)cn1]

5-Isothiocyanato-2-methoxypyridine [(476 mg, 2.86 mmol), *J. Org. Chem.* (1980), 45, 4219] was added to a solution of the product of preparation 31 (800 mg, 2.86 mmol) and N,N-diisopropylethylamine (1.45 mL, 8.58 mmol) in dichloromethane (10 mL) and the mixture was stirred for 3 hours at room temperature. The reaction mixture was then partitioned between dichloromethane and water and the organic layer was separated and washed with sodium hydrogen carbonate solution and brine. The organic solution was dried over magnesium sulfate and concentrated in vacuo. Trituration of the residue with diethyl ether afforded the title compound as a solid in 80% yield, 857 mg. $^1$H NMR (CDCl$_3$, 400 MHz) δ: 1.92-2.13 (m, 4H), 1.97 (s, 3H), 2.50 (s, 3H), 3.88-3.97 (m, 5H), 4.10-4.19 (m, 2H), 4.69-4.75 (m, 1H), 6.61 (d, 1H), 6.77 (m, 1H), 7.10 (s, 1H), 7.58 (dd, 1H), 7.98 (m, 1H), 8.22 (m, 1H); LRMS APCI m/z 373 [M+H]$^+$

Preparation 37: N-(6-Methoxypyridin-3-yl)-4-[(3-methylpyridin-4-yl)oxy]piperidine-1-carbothioamide

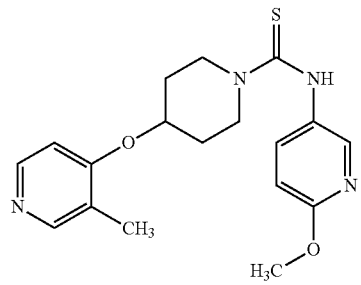 [SMILES: COc1ccc(NC(=S)N2CCC(Oc3ccncc3C)CC2)cn1]

The title compound was prepared from the product of preparation 32 using the same method as that described for 36, as a white solid in 63% yield. $^1$H NMR (CDCl$_3$, 400 MHz) δ: 1.94-2.01 (m, 2H), 2.02-2.13 (m, 2H), 2.19 (s, 3H), 3.85-3.97 (m, 5H), 4.08-4.15 (m, 2H), 4.72-4.79 (m, 1H), 6.71-6.6.74 (m, 2H), 7.16 (m, 1H), 7.56 (dd, 1H), 7.95 (m, 1H), 8.25 (m, 1H), 8.34 (m, 1H); LRMS APCI m/z 359 [M+H]$^+$

Preparation 38: Methyl N-(6-methoxypyridin-3-yl)-4-[(3-methylpyridin-2-yl)oxy]piperidine-1-carbimidothioate

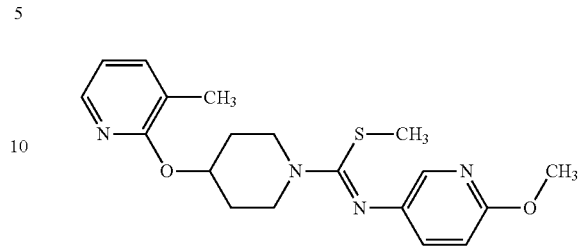

Potassium tert-butoxide (160 mg, 1.43 mmol) was added to a solution of the product of preparation 33 (465 mg, 1.30 mmol) in tetrahydrofuran (5 mL) and the mixture was stirred at room temperature for 1 hour. Methyl p-toluenesulfonate (271 mg, 1.43 mmol) was then added and the mixture was stirred for 3 hours at room temperature. The reaction mixture was concentrated in vacuo and the residue was partitioned between with water and dichloromethane. The organic layer was separated and washed with sodium hydrogen carbonate solution and brine. The organic solution was then dried over sodium sulfate and concentrated in vacuo to afford the title compound as a yellow oil in 93% yield, 450 mg. $^1$H NMR (CDCl$_3$, 400 MHz) δ: 1.81-1.95 (m, 2H), 2.05-2.15 (m, 5H), 2.20 (s, 3H), 3.59-3.65 (m, 2H), 3.72-3.79 (m, 2H), 3.95 (s, 3H), 5.38-5.43 (m, 1H), 6.69-6.81 (m, 1H), 6.77-7.01 (m, 1H), 7.20 (dd, 1H), 7.40 (m, 1H), 7.76 (m, 1H), 7.79 (m, 1H); LRMS APCI m/z 373 [M-F1-1]$^+$

Preparation 39: Methyl N-(6-methoxypyridin-3-yl)-4-(2-methylphenoxy)piperidine-1-carbimidothioate

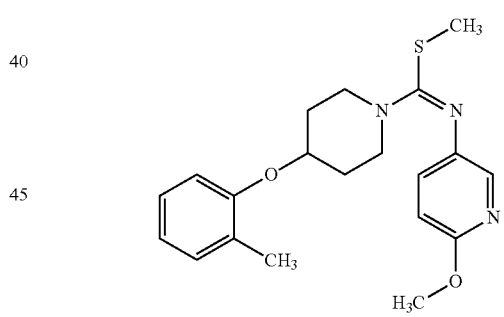

The title compound was prepared from the product of preparation 35 and methyl toluenesulfonate, using the same method as that described for 38, as an oil in quantitative yield. LRMS ESI m/z 394 [M+H]$^+$

Preparation 40: Methyl 4-hydroxy-N-(6-methoxypyridin-3-yl)piperidine-1-carbimidothioate

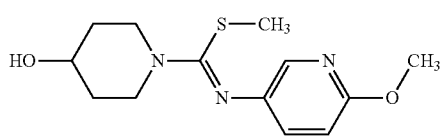

The title compound was prepared from the product of preparation 19, using the same method as that of preparation 38. The crude compound was purified by column chromatography on silica gel, eluting with dichloromethane:methanol, 95:5, to afford the title compound as a colourless oil in 57% yield. $^1$H NMR (CDCl$_3$, 400 MHz): 1.50 (d, 1H), 1.55-1.65 (m, 2H), 1.92-2.00 (m, 2H), 2.10 (s, 3H), 3.21-3.29 (m, 2H), 3.89-3.99 (m, 4H), 4.00-4.09 (m, 2H), 6.65 (d, 1H), 7.18 (d, 1H), 7.71 (s, 1H); LRMS APCI m/z 282 [M+H]$^+$ Preparation 41: Methyl 4-[(2,3-dimethylpyridin-4-yl)oxy]-N-(6-methoxypyridin-3-yl)piperidine-1-carbimidothioate

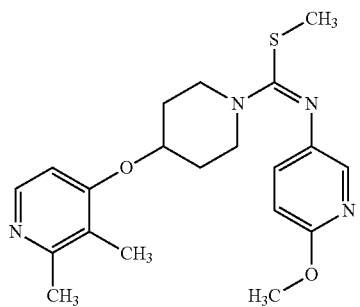 [SMILES: COc1ccc(/N=C(/SC)N2CCC(Oc3ccnc(C)c3C)CC2)cn1]

The title compound was prepared from the product of preparation 36, using the same method as that of preparation 38, as a colourless oil in quantitative yield. $^1$H NMR (CDCl$_3$, 400 MHz): 1.82-1.95 (m, 2H), 2.01-2.10 (m, 2H), 2.12 (s, 3H), 2.18 (s, 3H), 2.50 (s, 3H), 3.65-3.82 (m, 4H), 3.82 (s, 3H), 4.63-4.69 (m, 1H), 6.62 (d, 1H), 6.69 (d, 1H), 7.18 (dd, 1H), 7.76 (m, 1H), 8.22 (m, 1H); LRMS APCI m/z 387 [M+H]$^+$ Preparation 42: 1-[5-(Methoxymethyl)-4-(6-methoxypyridin-3-yl)-4H-1,2,4-triazol-3-yl]piperidin-4-ol

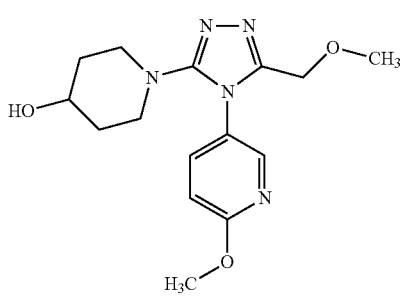 [SMILES: COCc1nnc(N2CCC(O)CC2)n1-c1ccc(OC)nc1]

The title compound was prepared from the product of preparation 40, using the same method as that described for preparation 4, in 55% yield. $^1$H NMR (CDCl$_3$, 400 MHz): 1.41 (d, 1H), 1.47-1.55 (m, 2H), 1.77-1.85 (m, 2H), 2.84-2.95 (m, 2H), 3.28-3.35 (m, 5H), 3.73-4.01 (m, 1H), 3.98 (s, 3H), 4.30 (s, 2H), 6.82 (d, 1H), 7.62 (m, 1H), 8.22 (m, 1H); LRMS APCI m/z 320 [M+H]$^+$ Preparation 43: 1-Benzyl-4-(2-chlorophenoxy)piperidine

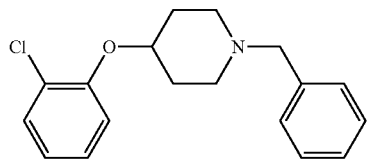 [SMILES: Clc1ccccc1OC1CCN(Cc2ccccc2)CC1]

Triphenylphosphine (1.91 g, 7.31 mmol) was added to an ice-cooled solution of di-isopropylazodicarboxylate (1.48 g, 7.31 mmol) in dichloromethane (15 mL) and the mixture was stirred for 10 minutes. A solution of 2-chlorophenol (806 mg, 6.27 mmol) and 1-benzyl-4-hydroxypiperidine (1 g, 5.22 mmol) in dichloromethane (5 mL) was then added dropwise to the ice-cooled reaction mixture and stirring continued for a further 72 hours. The reaction mixture was then concentrated in vacuo and the residue was dissolved in diethyl ether and extracted with saturated citric acid solution (5×10 mL). The combined aqueous solution was then basified with sodium hydroxide and extracted with dichloromethane (2×20 mL). The combined organic solution was dried over magnesium sulfate and concentrated in vacuo to afford the title compound as a clear oil in 89% yield, 1.4 g. $^1$H NMR (CDCl$_3$, 400 MHz): 1.85-1.95 (m, 2H), 1.97-2.08 (m, 2H), 2.32-2.47 (m, 2H), 3.58 (s, 2H), 4.46-4.34 (m, 1H), 6.87-6.95 (m, 2H), 7.16-7.22 (m, 1H), 7.20 (dd, 1H), 7.26-7.37 (m, 6H)

Preparation 44: 1-Benzyl-4-(3,5-difluorophenoxy)piperidine

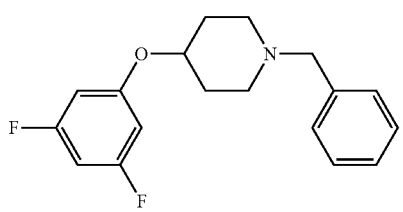 [SMILES: Fc1cc(F)cc(OC2CCN(Cc3ccccc3)CC2)c1]

The title compound was prepared from 1-benzyl-4-hydroxypiperidine and 3,5-difluorophenol, using the same method as that described for preparation 43. The crude compound was purified by column chromatography on silica gel, eluting with dichloromethane:methanol, 95:5, to afford the desired product in 63% yield. LRMS APCI m/z 304 [M+H]$^+$ Preparation 45: 4-(2-Chlorophenoxy)piperidine hydrochloride

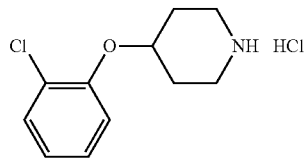 [SMILES: Clc1ccccc1OC1CCNCC1 ; Cl]

1-Chloroethyl chloroformate (0.95 g, 6.65 mmol) was added to an ice-cooled solution of the product of preparation 43 (1.34 g, 4.43 mmol) and "proton sponge", 1,8-bis(dimethylamino)naphthalene, (951 mg, 4.43 mmol) in dichloromethane (15 mL) and mixture was stirred for 45 minutes at room temperature. The reaction mixture was then washed with 10% citric acid solution (2×5 mL) and brine (5 mL), dried over magnesium sulfate and concentrated in vacuo. The residue was then dissolved in methanol and heated under reflux for 30 minutes. The reaction mixture was cooled to room temperature concentrated in vacuo, and the residue was triturated with diethyl ether to afford the title compound as a white solid in 69% yield, 890 mg. $^1$H NMR (DMSO-$d_6$, 400 MHz) δ: 1.80-1.95 (m, 2H), 2.05-2.20 (m, 2H), 3.05-3.30 (m, 4H), 4.70-4.85 (m, 1H), 6.90-7.00 (m, 1H), 7.15-7.30 (m, 2H), 7.35-7.45 (m, 1H), 8.70-9.20 (brm, 2H); LRMS APCI m/z 212/248 [M+H]$^+$ Preparation 46: 4-(3,5-Difluorophenoxy)piperidine hydrochloride

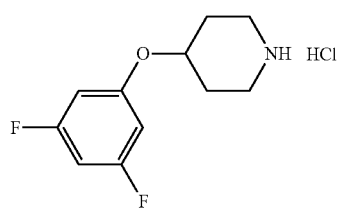 [SMILES: Fc1cc(F)cc(OC2CCNCC2)c1 ; Cl]

The title compound was prepared from the product of preparation 44, using the same method as that described for preparation 45, as a white solid in quantitative yield. $^1$H NMR (DMSO-$d_6$, 400 MHz) δ: 1.77-1.88 (m, 2H), 2.02-2.18 (m, 2H), 2.95-3.10 (m, 2H), 3.13-3.23 (m, 2H), 4.62-4.71 (m, 1H), 6.73-6.82 (m, 3H), 9.00-9.19 (brm, 2H); LRMS APCI m/z 214 [M+H]$^+$ Preparation 47: 4-(2-Chlorophenoxy)-N-(6-methoxypyridin-3-yl)piperidine-1-carbothioamide

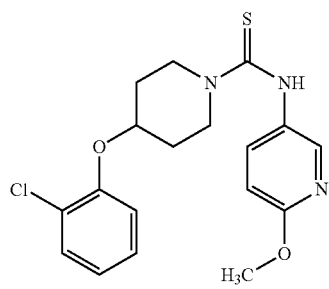 [SMILES: COc1ccc(NC(=S)N2CCC(Oc3ccccc3Cl)CC2)cn1]

The title compound was prepared from the product of preparation 45 and 5-isothiocyanato-2-methoxypyridine [(829 mg, 4.99 mmol), J. Org. Chem. (1980), 45, 4219], using the same procedure as that described for 35. The crude compound was purified by column chromatography on silica gel, eluting with dichloromethane:methanol:0.88 ammonia, 100:0:0 to 99:1:0.5, to afford the title compound as a white solid in 74% yield. $^1$H NMR (CDCl$_3$, 400 MHz) δ: 1.95-2.10 (m, 4H), 3.90-4.10 (m, 5H), 4.20-4.30 (m, 2H), 4.65-4.75 (m, 1H), 6.80 (d, 1H), 6.90-7.05 (m, 3H), 7.15-7.30 (m, 1H), 7.37 (d, 1H), 7.75-7.90 (m, 1H), 8.05 (s, 1H)

Preparation 48: 4-(3,5-difluorophenoxy)-N-(6-methoxypyridin-3-yl)piperidine-1-carbothioamide

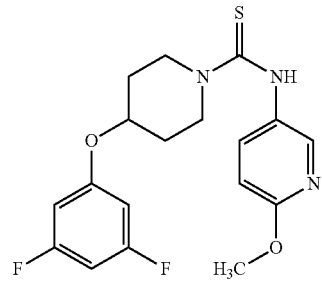 [SMILES: COc1ccc(NC(=S)N2CCC(Oc3cc(F)cc(F)c3)CC2)cn1]

The title compound was prepared from the product of preparation 46 and 5-Isothiocyanato-2-methoxypyridine [(829 mg, 4.99 mmol), J. Org. Chem. (1980), 45, 4219], using the same procedure as that described for 35, as a solid in 85% yield. LRMS APCI m/z 380 [M+H]$^+$ Preparation 49: tert-Butyl 4-[methyl(pyridin-2-yl)amino]piperidine-1-carboxylate

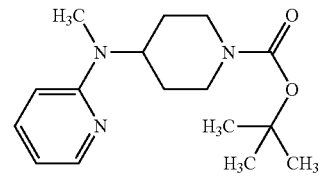 [SMILES: CN(c1ccccn1)C1CCN(C(=O)OC(C)(C)C)CC1]

A mixture of tert-butyl 4-(methylamino)piperidine-1-carboxylate (WO 03/089412, p22), (2 g, 9.33 mmol), 2-bromopyridine (1.35 mL, 13.99 mmol) and N,N-diisopropylethylamine (2.5 mL, 13.99 mmol) was heated at 130° C. for 3 hours. Potassium carbonate (2 g, 14 mmol) was added and the reaction mixture was heated at 130° C. for a further 8 hours. 2-Bromopyridine (1 mL, 10.36 mmol) was then added to the mixture and heating continued at 130° C. for 36 hours. The reaction mixture was then cooled and partitioned between ethyl acetate (30 mL) and water (15 mL). The organic layer was separated and extracted with saturated citric acid solution (2×15 mL), and the combined aqueous solution was basified with sodium hydrogen carbonate and extracted with dichloromethane (2×30 mL). The combined organic solution was dried over magnesium sulfate, concentrated in vacuo and the residue was purified by column chromatography on silica gel, eluting with ethyl acetate:pentane, 0:100 to 50:50, to afford the title compound in 24% yield, 646 mg. $^1$H NMR (CDCl$_3$, 400 MHz) δ: 1.45 (s, 9H), 1.55-1.70 (m, 4H), 2.78-2.90 (m, 5H), 4.10-4.30 (m, 2H), 4.65-4.80 (m, 1H), 6.45-6.55 (m, 2H), 7.40-7.45 (m, 1H), 8.10-8.15 (m, 1H); LRMS APCI m/z 292 [M+H]$^+$

Preparation 50: N-methyl-N-piperidin-4-ylpyridin-2-amine dihydrochloride

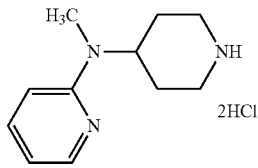

Hydrogen chloride gas was passed through an ice-cold solution of the product of preparation 49 (640 mg, 2.19 mmol) in dichloromethane (10 mL) until saturation was reached. The reaction mixture was then stirred at room temperature for 18 hours before the solvent was removed under reduced pressure. The residue was azeotroped with dichloromethane (×3), dissolved in methanol and heated under reflux for 5 minutes. The reaction mixture was then concentrated in vacuo and the residue was triturated with diethyl ether, and dried under vacuum at 60° C. to afford the title compound as a solid in 95% yield, 550 mg. $^1$H NMR (CDCl$_3$, 400 MHz) δ: 1.70-1.90 (m, 2H), 2.00-2.20 (m, 2H), 2.70-3.20 (m, 5H), 3.25-3.80 (m, 2H), 4.50-4.70 (m, 1H), 6.80-7.00 (m, 1H), 7.20-7.50 (m, 1H), 7.90-8.20 (m, 1H), 8.90-9.40 (m, 2H); LRMS APCI m/z 192 [M+H]$^+$

Preparation 51: N-(6-Methoxypyridin-3-yl)-4-[methyl(pyridin-2-yl)amino]piperidine-1-carbothioamide

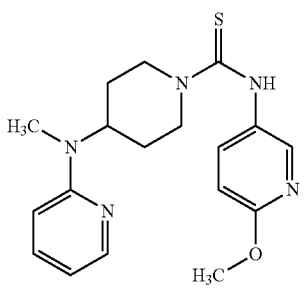 [SMILES: COc1ccc(NC(=S)N2CCC(N(C)c3ccccn3)CC2)cn1]

The title compound was prepared from 5-amino-2-methoxypyridine, 1'1-thiocarbonyldi-2(1H)-pyridone and the product of preparation 50, using the same method as that described for preparation 2, in quantitative yield. $^1$H NMR (CDCl$_3$, 400 MHz) δ: 1.78-2.10 (m, 4H), 2.84 (s, 3H), 3.19-3.31 (m, 2H), 3.94 (s, 3H), 4.77-4.85 (m, 2H), 4.96-5.15 (m, 1H), 6.50 (d, 1H), 6.58 (m, 1H), 6.74 (d, 1H), 7.04 (m, 1H), 7.45 (m, 1H), 7.59 (m, 1H), 7.99 (m, 1H), 8.15 (m, 1H); LRMS APCI m/z 358 [M+H]$^+$

Preparation 52: tert-Butyl 4-(methylamino)piperidine-1-carboxylate

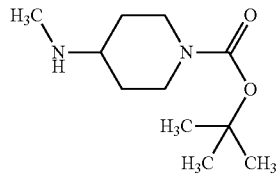

10% Pd/C (2 g) was added to a solution of tert-butyl 4-oxopiperidine-1-carboxylate (20 g, 100 mmol) in methylamine (33% in ethanol, 10 mL) and the mixture was stirred at room temperature, under 60 psi of hydrogen, for 18 hours. The reaction mixture was then filtered through Arbocel® and the filtrate was concentrated in vacuo. The residue was azeotroped with dichloromethane (×3) and the dried under vacuum for 72 hours to afford the title compound as a solid in 98% yield, 21.1 g. LRMS APCI m/z 215 [M+H]$^+$

Preparation 53: tert-Butyl 4-[[(benzyloxy)carbonyl](methyl)amino]piperidine-1-carboxylate

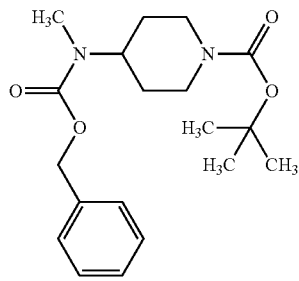 [SMILES: CN(C(=O)OCc1ccccc1)C1CCN(C(=O)OC(C)(C)C)CC1]

N-(Benzyloxycarbonyloxy)succinimide (5.5 g, 22.16 mmol) was added portionwise to a solution of the product of preparation 52 (5 g, 23.33 mmol) in dichloromethane (50 mL) and the mixture was stirred at room temperature for 18 hours. The reaction mixture was then washed with water (2×20 mL), saturated citric acid solution (20 mL) and brine (20 mL). The organic solution was dried over magnesium sulfate, concentrated in vacuo and the residue was triturated in pentane to afford the title compound as a solid in 81% yield, 6.63 g.

$^1$H NMR (CDCl$_3$, 400 MHz) δ: 1.40-1.80 (m, 13H), 2.60-3.00 (m, 5H), 3.95-4.40 (m, 3H), 5.15 (s, 2H), 7.20-7.50 (m, 5H)

Preparation 54: Benzyl methyl(piperidin-4-yl)carbamate

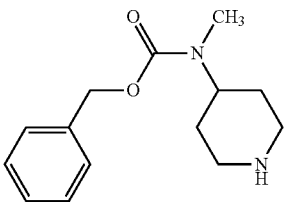 [SMILES: CN(C(=O)OCc1ccccc1)C1CCNCC1]

Trifluoroacetic acid (30 mL) was added to an ice-cooled solution of the product of preparation 53 (6.6 g, 19 mmol) in dichloromethane (30 mL) and the reaction was stirred for 1 hour, allowing the temperature to rise to 25° C. The reaction mixture was then concentrated in vacuo and the residue was partitioned between ethyl acetate (30 mL) and 1M sodium hydroxide solution (20 mL). The organic layer was separated, washed with saturated 1M sodium hydroxide solution and brine, dried over magnesium sulfate and concentrated in vacuo. The residue was then azeotroped with toluene (×2) to afford the title compound as an oil in quantitative yield, 4.64 g. $^1$H NMR (CDCl$_3$, 400 MHz) δ: 1.55-1.75 (m, 4H), 2.15-2.55 (brm, 1H), 2.60-2.90 (m, 5H), 3.10-3.25 (m, 2H), 3.80-4.40 (m, 1H), 5.15 (s, 2H), 7.20-7.45 (m, 5H); LRMS APCI m/z 249 [M+H]$^+$ Preparation 55: Benzyl (1-{[(6-methoxypyridin-3-yl)amino]carbonothioyl}piperidin-4-yl) methylcarbamate

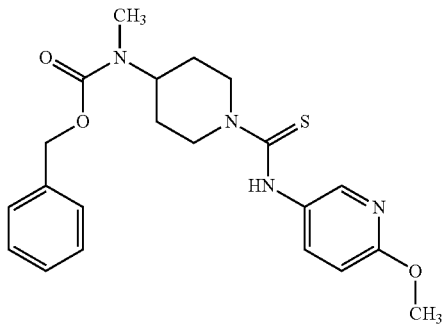 [SMILES: COc1ccc(NC(=S)N2CCC(N(C)C(=O)OCc3ccccc3)CC2)cn1]

The title compound was prepared from 5-amino-2-methoxypyridine, 1'1-thiocarbonyldi-2(1H)-pyridone and the product of preparation 54, using the same method as that described for preparation 2, in 77% yield. $^1$H NMR (CDCl$_3$, 400 MHz) δ: 1.70-1.90 (m, 4H), 2.75-2.90 (brs, 3H), 3.00-3.20 (m, 2H), 3.95 (s, 3H), 4.05-4.50 (m, 1H), 4.70-4.90 (m, 2H) 5.15 (s, 2H), 6.70-6.80 (d, 1H), 7.05-7.15 (brs, 1H), 7.30-7.45 (m, 5H), 7.50-7.60 (d, 1H), 7.95 (s, 1H); LRMS APCI m/z 415 [M+H]$^+$ Preparation 56: Benzyl {1-[4-(6-methoxypyridin-3-yl)-5-methyl-4H-1,2,4-triazol-3-yl]piperidin-4-yl}methylcarbamate

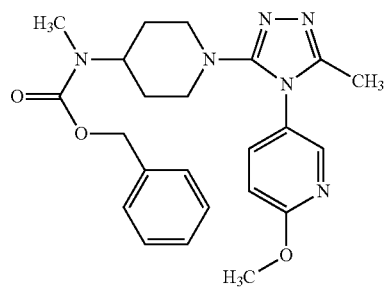 [SMILES: COc1ccc(-n2c(C)nnc2N2CCC(N(C)C(=O)OCc3ccccc3)CC2)cn1]

The title compound was prepared from the product of preparation 55, methyl tosylate and acethydrazide, using the same procedure as that described for preparation 20. The crude compound was purified by column chromatography on silica gel, eluting with dichloromethane:methanol, 100:0 to 93:7, to afford the title compound in 67% yield. $^1$H NMR (CDCl$_3$, 400 MHz) δ: 1.50-1.80 (m, 4H), 2.20 (s, 3H), 2.70-3.00 (m, 5H), 3.30-3.45 (m, 2H), 4.00 (s, 3H), 4.05-4.20 (m, 1H), 5.10 (s, 2H), 6.85-6.95 (m, 1H), 7.20-7.40 (m, 5H), 7.45-7.55 (m, 1H), 8.10 (s, 1H); LRMS APCI m/z 437 [M+H]$^+$ Preparation 57: 1-[4-(6-Methoxypyridin-3-yl)-5-methyl-4H-1,2,4-triazol-3-yl]-N-methylpiperidin-4-amine

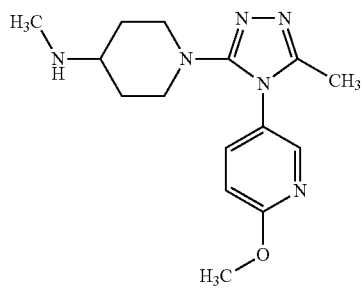

10% Pd/C (200 mg) was added to a solution of the product of preparation 56 (2.13 g, 4.88 mmol) in a mixture of ethanol (25 mL) and hydrochloric acid (2.5 mL) and the reaction mixture was stirred at room temperature, under 60 psi of hydrogen, for 80 hours. The reaction mixture was then filtered through Arbocel® and the filtrate was concentrated in vacuo. The residue was partitioned between dichloromethane (50 mL) and saturated sodium carbonate solution (20 mL), and the aqueous layer was separated and extracted with dichloromethane (3×10 mL). The combined organic solution was dried over magnesium sulfate concentrated in vacuo to afford the title compound as a foam in 87% yield, 1.28 g.

LRMS APCI m/z 303 [M+H]$^+$

Preparation 58: Methyl N-(6-methoxypyridin-3-yl)-4-(pyridin-4-yloxy)piperidine-1-carbimidothioate

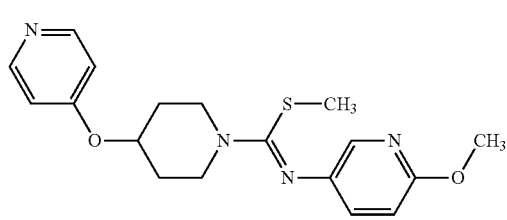 [SMILES: COc1ccc(/N=C(\SC)N2CCC(Oc3ccncc3)CC2)cn1]

The title compound was prepared from the product of preparation 34 and methyl toluenesulfonate, using the same method as that described for 38, as an oil in 99% yield. LRMS APCI m/z 359 [M+H]$^+$

Preparation 59: 2-(Piperidin-4-yloxy)benzonitrile

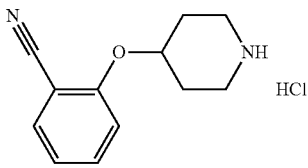 [SMILES: N#Cc1ccccc1OC1CCNCC1 ; Cl]

1-Boc-4-hydroxypiperidine (20 g, 99.35 mmol) and 2-cyanophenol (11.82 g, 99.35 mmol) were added to mixture of triphenylphosphine (26.06 g, 99.35 mmol) and di-tert-butyl azodicarboxylate (19.56 mL, 99.35 mmol) in tetrahydrofuran (800 mL) and the mixture was stirred at room temperature for 18 hours. The reaction mixture was then concentrated in vacuo and the residue was taken up in hydrochloric acid (4M in dioxane, 300 mL). The reaction mixture was stirred at room temperature for 18 hours and was then concentrated in vacuo. The residue was partitioned between water and ethyl acetate and the aqueous layer was separated and washed with ethyl acetate (2×100 mL). The aqueous solution was then basified with 2M sodium hydroxide solution and then extracted with diethyl ether (3×100 mL). The combined organic solution was dried over magnesium sulfate and concentrated in vacuo to afford the title compound as a white solid in quantitative yield. LRMS ESI m/z 203 [M+H]$^+$

Preparation 60: 4-(2-Cyanophenoxy)-N-(6-methoxy-pyridin-3-yl)piperidine-1-carbothioamide

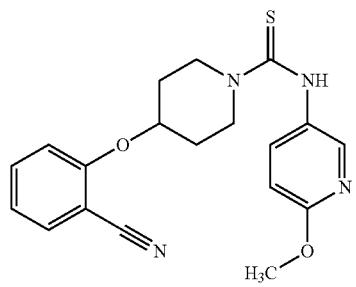 [SMILES: COc1ccc(NC(=S)N2CCC(Oc3ccccc3C#N)CC2)cn1]

The title compound was prepared from the product of preparation 59 and 5-isothiocyanato-2-methoxypyridine (*J. Org. Chem.* (1980), 45, 4219), using the same method as that described for preparation 35, as a white solid in 75% yield LRMS APCI m/z 369 [M+H]$^+$

Preparation 61: Methyl 4-(2-cyanophenoxy)-N-(6-methoxypyridin-3-yl)piperidine-1-carbimidothioate

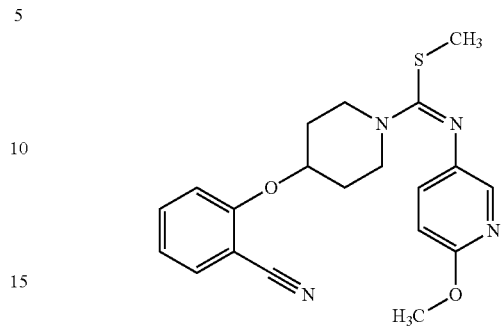

The title compound was prepared from the product of preparation 60 and methyl toluenesulfonate, using the same method as that described for 38. The crude product was the triturated to afford the title compound as a white solid in 73% yield. LRMS APCI m/z 383 [M+H]$^+$

Preparation 62: 1-(Diphenylmethyl)-3-phenoxyazetidine

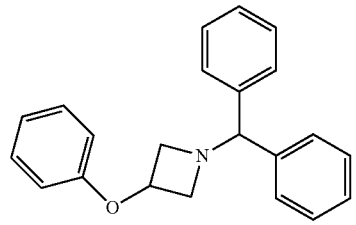 [SMILES: c1ccc(OC2CN(C(c3ccccc3)c3ccccc3)C2)cc1]

Phenol (6.68 g, 75 mmol) was added to a suspension of sodium hydride (60% dispersion in mineral oil, 2.82 g, 75 mmol) in toluene (50 mL) and the mixture was heated at 60° C. for 2 hours. The temperature was then increased to 80° C. and a solution of 1-(diphenylmethyl)-3-azetidinyl methanesulfonate (15 g, 47 mol) in toluene (150 mL) was added dropwise. The reaction mixture was stirred for 2 hours at 80° C., cooled then washed with water and dilute sodium hydroxide solution. The organic solution was dried over magnesium sulfate, concentrated in vacuo and the residue was re-crystallised from water/isopropanol to afford the title compound as a solid in 84% yield, 12.4 g. LRMS APCI m/z 316 [M+H]$^+$

Preparation 63: 3-Phenoxyazetidine

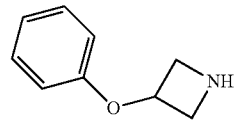 [SMILES: c1ccc(OC2CNC2)cc1]

10% Pd(OH)$_2$/C (500 mg) was added to a solution of the product of preparation 62 (10 g, 37 mmol) in ethanol (160 mL), and the mixture was stirred at 80° C., under 45 psi of hydrogen gas, for 18 hours. The reaction mixture was then filtered through Arbocel®, washing through with ethanol, and the filtrate was concentrated in vacuo. Trituration of the residue pentane afforded the title compound in 69% yield, 3.81 g. LRMS APCI m/z 150 [M+H]⁺

Preparation 64: N-(6-Methoxypyridin-3-yl)-3-phenoxyazetidine-1-carbothioamide

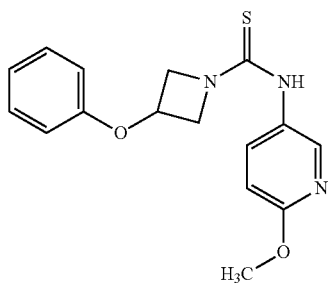 [SMILES: COc1ccc(NC(=S)N2CC(Oc3ccccc3)C2)cn1]

The title compound was prepared from the product of preparation 63 and 5-isothiocyanato-2-methoxypyridine (*J. Org. Chem.* (1980), 45, 4219), using the same method as that described for preparation 35, in 77% yield.
LRMS ESI m/z 316 [M+H]⁺

Preparation 65: Methyl N-(6-methoxypyridin-3-yl)-3-phenoxyazetidine-1-carbimidothioate

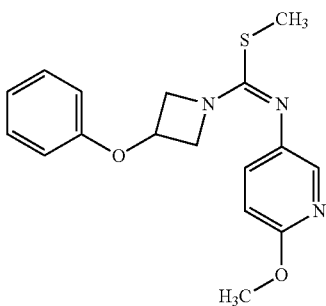 [SMILES: COc1ccc(/N=C(/SC)N2CC(Oc3ccccc3)C2)cn1]

The title compound was prepared from the product of preparation 64 and methyl p-toluenesulfonate, using the same method as that described for preparation 3, in 44% yield.
LRMS ESI m/z 330 [M+H]⁺

Preparation 66: 2-[(Dimethylamino)methyl]-3,5-difluorophenol

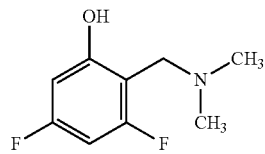

Potassium carbonate (7.82 g, 56.73 mmol) was added to a solution of 3,5-difluorophenol (4.92 g, 37.82 mmol) in acetonitrile (50 mL). N,N-Dimethylmethyleneiminium iodide (7.34 g, 39.71 mmol) was added and the mixture was stirred at room temperature for 2 hours. The resulting precipitate was filtered off, washing through with ethyl acetate and the filtrate was partitioned between ethyl acetate (30 mL) and water (15 mL). The organic layer was separated and extracted with saturated citric acid solution (2×15 mL). The combined aqueous solution was basified to pH 7 with solid sodium hydrogen carbonate and extracted with dichloromethane (2×30 mL). The combined organic solution was dried over magnesium sulfate and concentrated in vacuo to afford the title compound as a clear oil in 54% yield, 3.8 g. LRMS APCI m/z 188 [M+H]⁺

Preparation 67: 2-(Acetyloxy)-4,6-difluorobenzyl acetate

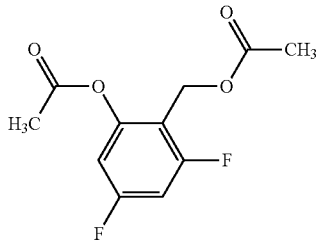 [SMILES: CC(=O)OCc1c(F)cc(F)cc1OC(C)=O]

Acetic anhydride (5.18 g, 50.75 mmol) was added to a solution of the product of preparation 66 (3.80 g, 20.30 mmol) in toluene (25 mL) and the mixture was heated under reflux for 1 hour. The reaction mixture was then cooled to room temperature and concentrated in vacuo. The residue was dissolved in ethyl acetate (20 mL), washed with water (×2) and brine, dried over magnesium sulfate and concentrated in vacuo. Purification of the residue by column chromatography on silica gel, eluting with dichloromethane:methanol 100:0 to 98:2, afforded the title compound in 61% yield, 3 g. ¹H NMR (400 MHz, CDCl₃) δ: 2.05 (s, 3H), 2.35 (s, 3H), 5.08 (s, 2H), 6.70-6.80 (m, 2H); LRMS APCI m/z 262 [M+NH₄]⁺

Preparation 68: 3,5-Difluoro-2-methylphenol

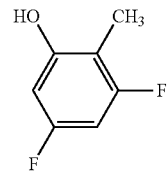

Sodium borohydride (2.28 g, 60.40 mmol) was added to a solution of the product of preparation 67 (2.85 g, 12.08 mmol) in 1,2-dimethoxyethane (25 mL) and the mixture was heated at 45° C. for 18 hours. The reaction mixture was then cooled with an ice/acetone bath and quenched with saturated ammonium chloride solution. The mixture was extracted with diethyl ether (2×20 mL) and the combined organic solution was washed with saturated ammonium chloride solution, dried over magnesium sulfate and concentrated in vacuo to afford the title compound in 75% yield, 1.3 g. ¹H NMR (400 MHz, CDCl₃) δ: 2.10 (s, 3H), 5.10-5.20 (brs, 1H), 6.35-6.45 (m, 2H).

Preparation 69: 2-Hydroxyacetohydrazide

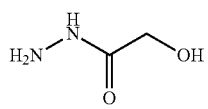

Hydrazine monohydrate (1.08 g, 22.2 mmol) was added to a solution of methyl glycolate (0.84 mL, 11.1 mmol) in methanol (10 mL) and the mixture was heated under reflux for 2 hours and stirred at room temperature for 72 hours. The reaction mixture was then concentrated in vacuo to afford the title compound as a white solid in quantitative yield. $^1$H NMR (400 MHz, CDCl$_3$) δ: 4.04 (s, 2H)

Preparation 70: 4-Hydroxy-3-methylbenzonitrile

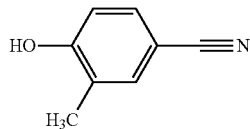

A mixture of 4-hydroxy-3-methylbenzaldehyde (530 mg, 3.91 mmol) and hydroxyl ammonium chloride (406 mg, 5.81 mmol) in acetic acid (5 mL) was heated under reflux for 90 minutes. The cooled reaction mixture was then diluted with diethyl ether (30 mL) and washed with water (30 mL). The combined organic solution was washed with brine, dried over magnesium sulfate, concentrated in vacuo and the residue was purified by column chromatography on silica gel, eluting with dichloromethane:methanol, 100:0 to 97.5:2.5, to afford the title compound as a pale yellow oil in 66% yield, 345 mg.

$^1$H NMR (400 MHz, CDCl$_3$) δ: 2.25 (s, 3H), 6.84 (d, 1H), 7.37 (d, 1H), 7.40 (s, 1H)

Preparation 71: 3-Chloro-4-hydroxybenzonitrile

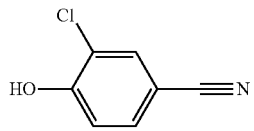

The title compound was prepared from 3-chloro-4-hydroxybenzaldehyde and hydroxyl ammonium chloride, using the same method as that described for preparation 70. The title compound was purified by column chromatography on silica gel, eluting with pentane:ethyl acetate, 100:0 to 90:10, to afford the title compound as a white solid in 76% yield.

$^1$H NMR (400 MHz, CDCl$_3$) δ: 7.10 (d, 1H), 7.52 (d, 1H), 7.66 (s, 1H)

Preparation 72: 2-Chloro-3-hydroxybenzonitrile

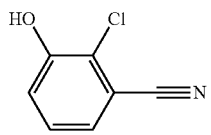

A mixture of 2-chloro-3-hydroxybenzaldehyde [(2 g, 12.8 mmol) WO 2005007633, p34] and hydroxyl ammonium chloride (1.33 g, 19.6 mmol) in acetic acid (20 mL) was heated under reflux for 2 hours. The reaction mixture was then cooled to room temperature and partitioned between diethyl ether and water. The organic layer was separated, washed with brine, dried over magnesium sulfate and concentrated in vacuo to give a white solid. The solid was then dissolved in ethyl acetate washed with water and brine, dried over magnesium sulfate and concentrated in vacuo to afford the title compound as a solid in quantitative yield.

$^1$H NMR (400 MHz, CD$_3$OD) δ: 7.18 (d, 1H), 7.26 (m, 2H)

Preparation 73: 3-Fluoro-2-(trifluoromethyl)phenol

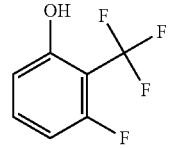 [SMILES: Oc1cccc(F)c1C(F)(F)F]

A solution of 3-fluoro-2-(trifluoromethyl)bromobenzene (1 g, 4.1 mmol) in tetrahydrofuran (25 mL) was added dropwise to "butyl lithium (2.5M in hexanes, 3.2 mL, 8 mmol), at 78° C., and the mixture was stirred at this temperature for 30 minutes. Trimethyl borate (1.84 mL, 16.4 mmol) was added and the reaction mixture was stirred at 78° C. for a further 30 minutes and at room temperature for 18 hours. 2M sodium hydroxide solution (4 mL) and 35% hydrogen peroxide solution (2 mL) were then added and the mixture was heated under reflux for 3 hours. The reaction mixture was cooled to room temperature and diluted with diethyl ether (100 mL). The aqueous layer was separated and the organic solution was washed with 2M sodium hydroxide solution. The combined basic washings were acidified with 2M hydrochloric acid, extracted with diethyl ether (2×50 mL) and the organic solution was concentrated in vacuo to afford the title compound as a yellow oil in 40% yield, 300 mg. $^1$H NMR (400 MHz, CD$_3$OD) δ: 6.64 (m, 1H), 6.75 (d, 1H), 7.36 (q, 1H)

Preparation 74: 3-Hydroxy-2-methylbenzonitrile

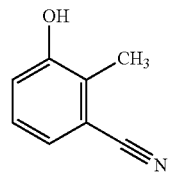

A solution of 3-methoxy-2-methylbenzonitrile [(1 g, 6.79 mmol) U.S. Pat. No. 5,965,766, p6] and tetra ″butyl ammonium iodide (4.12 g, 17 mmol) in dichloromethane (15 mL) was cooled to −78° C. and purged with nitrogen. Boron trichloride (1M in dichloromethane, 17 mL, 17 mmol) was added dropwise and the mixture was stirred for 15 minutes at −78° C. and at room temperature for 3 hours. The reaction mixture was quenched with water, stirred for 30 minutes and concentrated in vacuo. The aqueous residue was extracted with diethyl ether and the organic solution was washed with water (×5), dried over magnesium sulfate and concentrated in vacuo to afford the title compound as a brown solid in 91% yield, 826 mg. $^1$H NMR (400 MHz, CDCl$_3$) δ: 2.20 (s, 3H), 7.10 (m, 1H), 7.20 (d, 1H), 10.10 (s, 1H); LRMS APCI m/z 132 [M−H]$^-$ Preparation 75: 3-Hydroxy-2-methylbenzamide

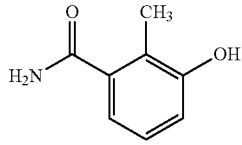

Oxalyl chloride (4.19 ml, 48 mmol) was added to an ice-cold solution of 3-hydroxy-2-methylbenzoic acid (3.62 g, 24 mmol) in dichloromethane (30 mL). N,N-dimethylformamide (2 mL) was then added and the mixture was stirred at room temperature for 18 hours. The reaction mixture was concentrated in vacuo and the residue was concentrated in vacuo three times from toluene. The residue was then suspended in tetrahydrofuran (10 mL), added to ice-cold 0.88 ammonia solution (10 mL) and stirred for 2.5 hours, allowing the temperature to rise to ambient. The reaction mixture was then extracted with ethyl acetate, dried over magnesium sulfate and concentrated in vacuo and the residue was concentrated in vacuo from acetone and triturated with diethyl ether to afford the title compound as a solid in 45% yield. LRMS APCI m/z 152 [M+H]$^+$ Preparation 76: 3-Hydroxy-N,N,2-trimethylbenzamide

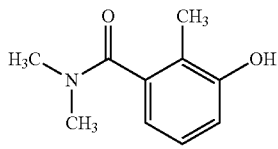

The title compound was prepared from 3-hydroxy-2-methylbenzoic acid and dimethylamine, using the same method as that described for preparation 75, as a solid in 42% yield. $^1$H NMR (400 MHz, CDCl$_3$) δ: 1.95 (s, 3H), 2.70 (s, 3H), 2.95 (s, 3H), 6.55 (d, 1H), 6.80 (d, 1H), 7.00 (m, 1H), 9.50 (s, 1H); LRMS APCI m/z 180 [M+H]$^+$ Preparation 77: 2-(Methoxymethyl)phenol

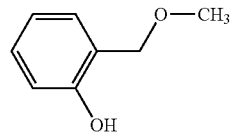

A solution of 2-hydroxybenzyl alcohol (5 g, 40 mmol) in methanol (25 mL) was heated in a sealed vessel at 150° C. for 4 hours. The reaction mixture was then concentrated in vacuo and the residue was purified by fractional distillation (90° C./10 mm Hg) to afford the title compound as a colourless liquid in 58% yield, 3.22 g. LRMS APCI m/z 137 [M−H]$^-$ Preparation 78: 3-(2-Chloro-4-fluorophenoxy)-1-(diphenylmethyl)azetidine

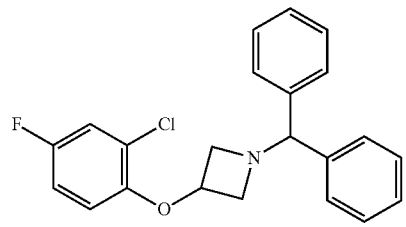 [SMILES: Fc1ccc(OC2CN(C(c3ccccc3)c3ccccc3)C2)c(Cl)c1]

A mixture of 1-(diphenylmethyl)-3-azetidinyl methanesulfonate (363.8 g, 1.15 mol), potassium carbonate (330 g, 2.38 mol) and 2-chloro-4-fluorophenol (140 g, 0.96 mol) in acetonitrile (2.5 L) was heated under reflux for 4.5 hours. The cooled reaction mixture was then concentrated in vacuo and the residue was partitioned between ethyl acetate (10 and water (500 mL). The organic layer was separated, dried over sodium sulfate concentrated in vacuo and the residue was triturated with ethyl acetate/pentane/dichloromethane, 90:10:1, to afford the title compound as a white solid in quantitative yield, 350 g. $^1$H NMR (400 MHz, CDCl$_3$) δ: 3.19 (m, 2H), 3.75 (m, 2H), 4.45 (m, 1H), 4.78 (m, 1H), 6.60 (m, 1H), 6.83 (m, 1H), 7.14 (m, 1H), 7.18-7.50 (m, 10H)

Preparation 79: 3-(2-Chloro-4-fluorophenoxy)azetidine hydrochloride

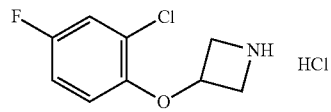 [SMILES: Fc1ccc(OC2CNC2)c(Cl)c1 ; Cl]

A solution of the product of preparation 78 (5 g, 13.59 mmol) and 1,8-bis(dimethylamino)naphthalene (2.91 g, 13.59 mmol) in dichloroethane (50 mL) was treated with chloroethylchloroformate (4.08 g, 28.54 mmol) and the mixture was then heated under reflux for 2 hours. The reaction mixture was cooled to room temperature, diluted with dichloromethane (60 mL), washed with 2N hydrochloric acid (2×30 mL), dried over sodium sulfate and concentrated in vacuo. The residue was then azeotroped with toluene and dichloromethane, triturated with diethyl ether and purified by HPLC using a Phenomenex Luna C18 system, eluting with water/acetonitrile/trifluoroacetic acid (5:95:0.1):acetonitrile, 95:5 to 5:95, to afford the title compound in 52% yield, 1.69 g. $^1$H NMR (400 MHz, CDCl$_3$) δ: 4.22 (m, 2H), 4.58 (m, 2H), 5.18 (m, 1H), 6.92 (m, 1H), 7.04 (m, 1H), 7.30 (m, 1H); LRMS ESI m/z 202 [M+H]$^+$ Preparation 80: 3-(2-Chloro-4-fluorophenoxy)-N-(6-methoxypyridin-3-yl)azetidine-1-carbothioamide

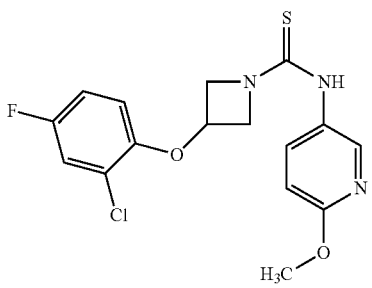 [SMILES: COc1ccc(NC(=S)N2CC(Oc3ccc(F)cc3Cl)C2)cn1]

N-methylmorpholine (16.6 mL, 150.8 mmol) and 5-isothiocyanato-2-methoxypyridine [(20.9 g, 125.7 mmol), J. Org. Chem. (1980), 45, 4219] were added portionwise to a ice-cooled suspension of the product of preparation 79 [(29.93 g, 125.7 mmol) in tetrahydrofuran (150 mL) and the mixture was stirred for 1 hour at room temperature. The reaction mixture was concentrated in vacuo and the residue was re-crystallised from water. The resulting solid was filtered, washing through with water and diethyl ether, and dried under vacuum, at 45° C., for 18 hours to afford the title compound as a solid in 74% yield, 34 g.

LRMS APCI m/z 368 [M+H]$^+$

Preparation 81: Methyl 3-(2-chloro-4-fluorophenoxy)-N-(6-methoxypyridin-3-yl)azetidine-1-carbimidothioate

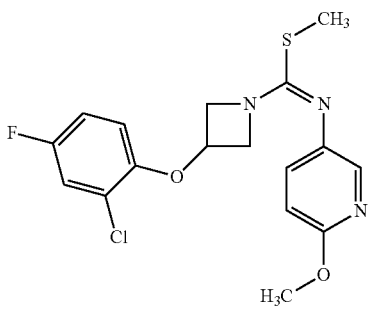 [SMILES: COc1ccc(/N=C(/SC)N2CC(Oc3ccc(F)cc3Cl)C2)cn1]

The title compound was prepared from the product of preparation 80 and potassium tert-butoxide, using the same method as that described for preparation 3, in quantitative yield.

LRMS APCI m/z 382 [M+H]$^+$

Preparation 82: 1-[4-(6-Methoxypyridin-3-yl)-5-methyl-4H-1,2,4-triazol-3-yl]azetidin-3-ol

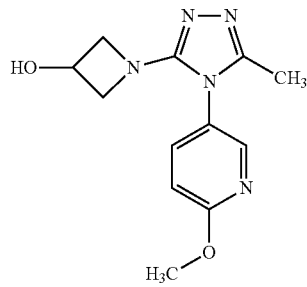 [SMILES: COc1ccc(-n2c(C)nnc2N2CC(O)C2)cn1]

A mixture of the product of preparation 4 (1 g, 2.95 mmol) and 2M sodium hydroxide solution (10 mL) in ethanol (20 mL) was heated under reflux for 24 hours. The reaction mixture was then cooled to room temperature, acidified to pH6 with hydrochloric acid and extracted with dichloromethane. The organic solution was concentrated in vacuo and the residue was purified by column chromatography on silica gel, eluting with dichloromethane:methanol, 100:0 to 50:50, to afford the title compound as a brown oil in 26% yield, 200 mg. $^1$H NMR (400 MHz, CDCl$_3$) δ: 2.17 (s, 3H), 3.80 (m, 2H), 3.95 (m, 2H), 4.03 (s, 3H), 4.57 (m, 1H), 6.88 (d, 1H), 7.52 (dd, 1H), 8.11 (d, 1H); LRMS ESI m/z 262 [M+H]$^+$ Preparation 83: 3-Methoxy-4-[(3R)-pyrrolidin-3-yloxy]benzonitrile

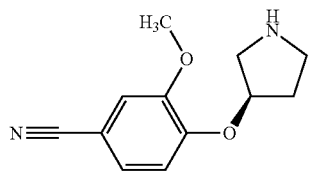 [SMILES: COc1cc(C#N)ccc1O[C@@H]1CCNC1]

4-Hydroxy-3-methoxybenzonitrile (12 g, 80.2 mmol) and triphenylphosphine (21 g, 80.2 mmol) were added portionwise to an ice-cold solution of tert-butyl (3S)-3-hydroxypyrrolidine-1-carboxylate (15 g, 80.2 mmol) in tetrahydrofuran (225 mL). A solution of diisopropyl azodicarboxylate (16.2 g, 80.2 mmol) in tetrahydrofuran (100 mL) was then added dropwise and the mixture was stirred at room temperature for 18 hours. The reaction mixture was then concentrated in vacuo and the residue was treated with hydrochloric acid (4M in dioxane, 250 mL). The mixture was concentrated in vacuo and the residue was partitioned between ethyl acetate and water. The organic layer was separated and washed with water (100 mL), and the combined aqueous solution was washed with ethyl acetate (2×150 mL), basified to pH10 with solid potassium carbonate and extracted with ethyl acetate (2×250 mL). The combined organic solution was washed with brine (100 mL), dried over magnesium sulfate and concentrated in vacuo to afford the title compound as a cream solid in 67% yield, 11.8 g.

LRMS ESI m/z 219 [M+H]$^+$

Preparation 84:
(3R)-3-(2-Chlorophenoxy)pyrrolidine hydrochloride

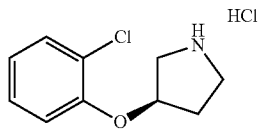 [SMILES: Cl ; Clc1ccccc1O[C@@H]1CCNC1]

Diisopropyl azodicarboxylate (21 mL, 107 mmol) and 4-hydroxy-3-chlorophenol (11.1 mL, 107 mmol) were added portionwise to an ice-cold solution of tert-butyl (3S)-3-hydroxypyrrolidine-1-carboxylate (20 g, 107 mmol) and triphenylphosphine (28.1 g, 107 mmol) in tetrahydrofuran (320 mL) and the mixture was stirred at room temperature for 18 hours. The reaction mixture was then concentrated in vacuo and the residue was treated with hydrochloric acid (4M in dioxane, 250 mL). The mixture was concentrated in vacuo and the residue was partitioned between ethyl acetate (400 mL) and water (400 mL). The organic layer was separated and washed with water (100 mL), and the combined aqueous solution was washed with ethyl acetate (2×300 mL), basified to pH9 with solid potassium carbonate and extracted with ethyl acetate (2×400 mL). The combined organic solution was then washed with water (3×300 mL), dried over magnesium sulfate and concentrated in vacuo. The residual oil was dissolved in diethyl ether (60 mL), treated dropwise with hydrochloric acid (4M in dioxane, 25 mL) and the resulting precipitate was filtered off, washing through with diethyl ether, and dried to afford the title compound as a white solid in 55% yield, 13.69 g. LRMS APCI m/z 198 [M+H]$^+$

Preparation 85:
(3R)-3-(2-methoxyphenoxy)pyrrolidine hydrochloride

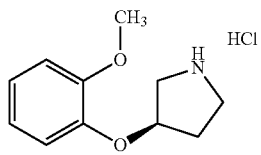

The title compound was prepared from tert-butyl (3S)-3-hydroxypyrrolidine-1-carboxylate and 2-methoxyphenol, using the same method as that described for preparation 84, as a white solid in 45% yield. Microanalysis: found (%) C (57.43), H (7.05), N (6.08); C$_{11}$H$_{15}$NO$_2$ requires: (%) C (57.50), H (6.96), N (6.09)

Preparation 86:
(3R)-3-(2-Methylphenoxy)pyrrolidine hydrochloride

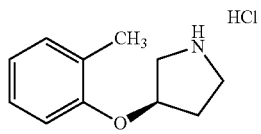

The title compound was prepared from tert-butyl (3S)-3-hydroxypyrrolidine-1-carboxylate and o-Cresol, using the same method as that described for preparation 84, as a pale pink solid in 54% yield. LRMS APCI m/z 178 [M+H]$^+$

Preparation 87:
2-[(3R)-pyrrolidin-3-yloxy]benzonitrile maleate

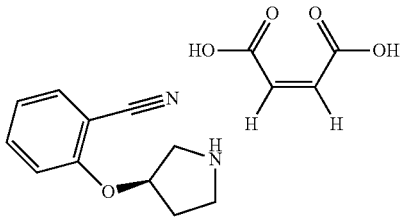

2-Hydroxybenzonitrile (9.5 g, 80.2 mmol) and triphenylphosphine (21 g, 80.2 mmol) were added portionwise to an ice-cold solution of tert-butyl (3S)-3-hydroxypyrrolidine-1-carboxylate (15 g, 80.2 mmol) in tetrahydrofuran (225 mL). A solution of diisopropyl azodicarboxylate (16.2 g, 80.2 mmol) in tetrahydrofuran (100 mL) was then added dropwise and the mixture was stirred at room temperature for 18 hours. The reaction mixture was then concentrated in vacuo and the residue was treated with hydrochloric acid (4M in dioxane, 250 mL). The mixture was concentrated in vacuo and the residue was partitioned between ethyl acetate and water. The organic layer was separated and washed water (100 mL), and the combined aqueous solution was washed with ethyl acetate (2×150 mL), basified to pH10 with solid potassium carbonate and extracted with ethyl acetate (2×250 mL). The combined organic solution was washed with brine (100 mL), dried over magnesium sulfate and concentrated in vacuo. The residue was diluted with ethyl acetate and treated with a solution of maleic acid (6.5 g) in ethyl acetate (200 mL) and the mixture was stirred at room temperature for 30 minutes. The resulting precipitate was then filtered off, washing through with ethyl acetate, and dried to afford the title compound as a cream solid in 49% yield, 12 g.
LRMS ESI m/z 189 [M+H]$^+$

Preparation 88:
4-[(3R)-Pyrrolidin-3-yloxy]benzonitrile maleate

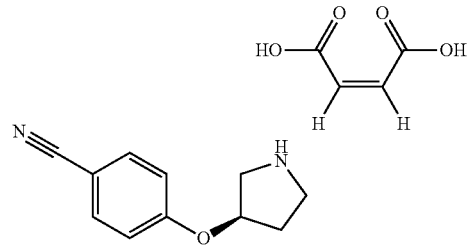

4-Hydroxybenzonitrile (9.5 g, 80.2 mmol) and triphenylphosphine (21 g, 80.2 mmol) were added portionwise to an ice-cold solution of tert-butyl (3S)-3-hydroxypyrrolidine-1-carboxylate (15 g, 80.2 mmol) in tetrahydrofuran (225 mL). A solution of diisopropyl azodicarboxylate (16.2 g, 80.2 mmol) in tetrahydrofuran (100 mL) was then added dropwise and the mixture was stirred at room temperature for 18 hours. The reaction mixture was then concentrated in vacuo and the residue was treated with hydrochloric acid (4M in dioxane, 250 mL). The mixture was concentrated in vacuo and the residue was partitioned between ethyl acetate and water. The organic layer was separated and washed water (100 mL), and the combined aqueous solution was washed with ethyl acetate (2×150 mL), basified to pH10 with solid potassium carbonate and extracted with ethyl acetate (2×250 mL). The combined organic solution was washed with brine (100 mL), dried over magnesium sulfate, concentrated in vacuo and the residue was purified by column chromatography on silica gel, eluting with dichloromethane:methanol: 0.88 ammonia, 97:3:1 to 90:10:1. The appropriate franctions were evaporated under reduced pressure and the residue was diluted with ethyl acetate and treated with a solution of maleic acid (5 g) in ethyl acetate (140 mL). The resulting precipitate was then filtered off, washing through with ethyl acetate, and dried to afford the title compound as a cream solid in 65% yield, 9.87 g. LRMS ESI m/z 189 [M+H]$^+$ Preparation 89:
(3R)-3-(4-Fluorophenoxy)pyrrolidine

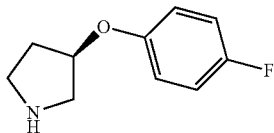 [SMILES: Fc1ccc(O[C@@H]2CCNC2)cc1]

Diethyl azodicarboxylate (60.5 mL, 384 mmol) was added to an ice-cooled mixture of (S)-(−)-1-benzyl-3-pyrrolidinol (56.72 g, 320 mmol), 4-fluorophenol (39.45 g, 352 mmol) and triphenyl phosphine (100.7 g, 384 mmol) in tetrahydrofuran (500 mL) and the mixture was stirred for 18 hours, allowing the temperature to rise to ambient. The reaction mixture was then concentrated in vacuo and the residue was taken up in pentane:dichloromethane, 90:10. The resulting precipitate was filtered off and the filtrate was concentrated in vacuo. The residue was then purified by column chromatography on silica gel, eluting with dichloromethane. The appropriate fractions were evaporated under reduced pressure and a portion of the residue (5 g) was dissolved in methanol (100 mL). 10% Pd/C (0.5 g) and ammonium formate (5.8 g, 92 mmol) were added and the mixture was stirred at room temperature for 3 hours. The mixture was then filtered through Arbocel® and the filtrate was concentrated in vacuo purified by column chromatography on silica gel, eluting with dichloromethane:methanol, 0.88 ammonia, 95:5:0.5 to 90:10:1, to afford the title compound as a colourless oil. $^1$H NMR (400 MHz, DMSO-d$_6$) δ: 2.03 (m, 2H), 3.10-3.29 (m, 3H), 3.36 (m, 1H), 5.01 (m, 1H), 6.96 (m, 2H), 7.08 (m, 2H).

Preparation 90:
(3S)-3-(2-Methoxyphenoxy)pyrrolidine hydrochloride

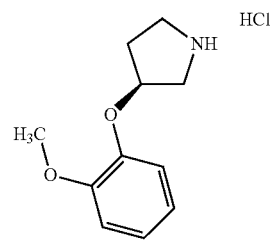

The title compound was prepared from tert-butyl (3R)-3-hydroxypyrrolidine-1-carboxylate and 2-methoxyphenol, using the same method as that described for preparation 84, as a pale pink solid in 40% yield. LCMS APCI m/z 194 [M+H]$^+$ Preparation 91:
(3S)-3-(2-Chlorophenoxy)pyrrolidine hydrochloride

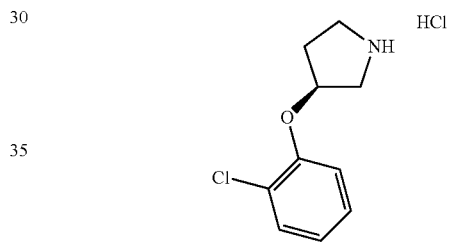

The title compound was prepared from tert-butyl (3R)-3-hydroxypyrrolidine-1-carboxylate and 2-chlorophenol, using the same method as that described for preparation 84, as a pale pink solid in 54% yield. LCMS APCI m/z 198 [M+H]$^+$ Preparation 92:
(3S)-3-(2-Methylphenoxy)pyrrolidine hydrochloride

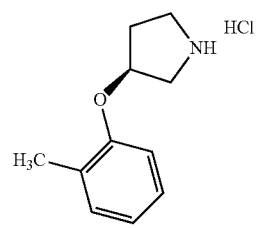

The title compound was prepared from tert-butyl (3R)-3-hydroxypyrrolidine-1-carboxylate and 2-methylphenol, using the same method as that described for preparation 84, as a white solid in 40% yield. LCMS APCI m/z 178 [M+H]$^+$

Preparation 93: (3S)-3-Hydroxy-N-(6-methoxypyridin-3-yl)pyrrolidine-1-carbothioamide

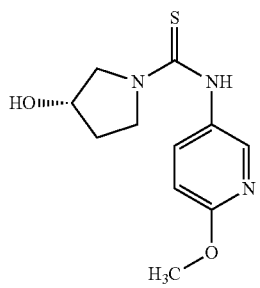 [SMILES: COc1ccc(NC(=S)N2CC[C@H](O)C2)cn1]

The title compound was prepared from (S)-3-hydroxypyrrolidine and 5-isothiocyanato-2-methoxypyridine (*J. Org. Chem.* (1980), 45, 4219), using the same method as that described for preparation 35, in 99% yield. $^1$H NMR (400 MHz, CD$_3$OD) δ: 1.91-2.22 (m, 2H), 3.69-3.81 (m, 4H), 3.88 (s, 3H), 4.40-4.52 (m, 1H), 6.78 (d, 1H), 7.69 (dd, 1H), 8.00 (m, 1H); LCMS m/z 254 [M+H]$^+$

Preparations 94 to 100

The following compounds, of the general formula shown below, were prepared using the same method to that described for preparation 35, using the products of preparations 83-89 and 5-isothiocyanato-2-methoxypyridine (*J. Org. Chem.* (1980), 45, 4219).

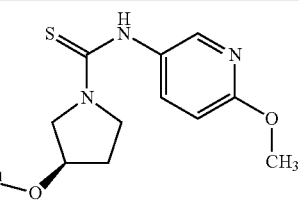

| No. | R$^1$ | Data (LRMS and/or $^1$H NMR) | Yield |
|---|---|---|---|
| 94 | 3-methoxy-4-cyanophenyl | APCI m/z 385 [M + H]$^+$ | 95% |
| 95 | 2-chlorophenyl | δ: 2.30(m, 1H), 2.45(m, 1H), 3.87-4.20(m, 7H), 5.05(m, 1H), 6.80(m, 2H), 6.95(m, 2H), 7.25(m, 1H), 7.40(d, 1H), 7.76(dd, 1H), 8.05(d, 1H); APCI m/z 364 [M + H]$^+$ | 67% |
| 96 | 2-methoxyphenyl | APCI m/z 360 [M + H]$^+$ | 93% |
| 97 | 2-methylphenyl | δ: 2.20(s, 3H), 2.30(m, 1H), 2.45(m, 1H), 3.80-4.00(m, 5H), 4.05(m, 2H), 5.08(m, 1H), 6.78(m, 3H), 6.90(d, 1H), 7.15(m, 1H), 7.70(dd, 1H), 8.05(d, 1H); APCI m/z 344 [M + H]$^+$ | 85% |
| 98 | 2-cyanophenyl | APCI m/z 355 [M + H]$^+$ | 97% |
| 99 | 4-cyanophenyl | APCI m/z 355 [M + H]$^+$ | 59% |
| 100 | 4-fluorophenyl | APCI m/z 348 [M + H]$^+$ | 72% |

NMR spectra were run at 400 MHz in CDCl$_3$

Preparation 101: (3S)-3-(2-Methoxyphenoxy)-N-(6-methoxypyridin-3-yl)pyrrolidine-1-carbothioamide

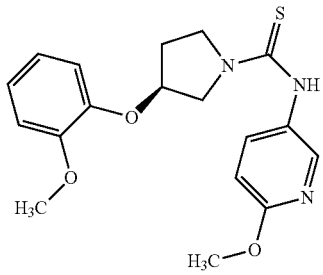 [SMILES: COc1ccc(NC(=S)N2CC[C@H](Oc3ccccc3OC)C2)cn1]

The title compound was prepared from the product of preparation 90 and 5-isothiocyanato-2-methoxypyridine (*J. Org. Chem.* (1980), 45, 4219), using the same method as that described for preparation 35, in 90% yield.

LRMS APCI m/z 360 [M+H]$^+$

Preparation 102: Methyl (3S)-3-hydroxy-N-(6-methoxypyridin-3-yl)pyrrolidine-1-carbimidothioate

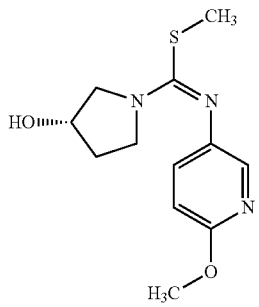 [SMILES: COc1ccc(/N=C(/SC)N2CC[C@H](O)C2)cn1]

The title compound was prepared from the product of preparation 93 and methyl p-toluenesulfonate, using the same method as that described for preparation 3. The crude compound was re-crystallised from diethyl ether/cyclohexane to afford the desired product as a solid in 94% yield.
$^1$H NMR (400 MHz, CD$_3$OD) δ: 1.91-2.20 (m, 2H), 2.01 (s, 3H), 3.58 (m, 1H), 3.63-3.75 (m, 3H), 3.83 (s, 3H), 4.40 (m, 1H), 6.77 (d, 1H), 7.34 (dd, 1H), 7.68 (m, 1H); LCMS m/z 268 [M+H]$^+$

Preparations 103 to 109

The following compounds, of the general formula shown below, were prepared using the same method to that described for preparation 3, using the products of preparations 94 to 100 and methyl p-toluenesulfonate.

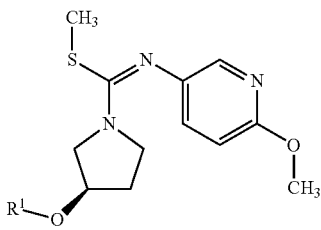

| No. | R$^1$ | Data (LRMS and/or $^1$H NMR) | Yield |
|---|---|---|---|
| 103 | H$_3$C-O-, 4-cyanophenyl | LRMS APCI m/z 399 [M + H]$^+$ | 79% |
| 104 | 2-chlorophenyl | δ: 2.00(s, 3H), 2.20(m, 1H), 2.30(m, 1H), 3.87-4.20(m, 7H), 5.00(m, 1H), 6.65(d, 1H), 6.95(m, 2H), 7.25(m, 2H), 7.40(dd, 1H), 7.80(d, 1H); APCl m/z 378 [M + H]$^+$ | 97% |
| 105 | 2-methoxyphenyl | APCl m/z 374 [M + H]$^+$ | 65% |
| 106 | 2-methylphenyl | δ: 2.00(s, 3H), 2.20(m, 4H), 2.28(m, 1H), 3.80(m, 4H), 3.90(s, 3H), 4.98(m, 1H), 6.68(d, 1H), 6.80 (d, 1H), 6.90(m, 1H), 7.15(m, 2H), 7.25(m, 1H), 7.80(d, 1H); APCl m/z 358 [M + H]$^+$ | 92% |

-continued

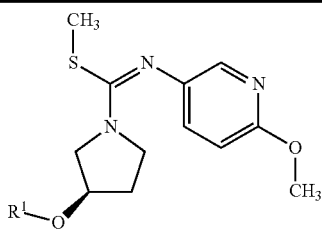

| No. | R¹ | Data (LRMS and/or ¹H NMR) | Yield |
|---|---|---|---|
| 107 | (2-cyanophenylmethyl) | APCl m/z 369 [M + H]⁺ | 92% |
| 108 | (4-cyanophenylmethyl) | APCl m/z 369 [M + H]⁺ | 98% |
| 109 | (4-fluorophenylmethyl) | APCl m/z 362 [M + H]⁺ | 79% |

NMR spectra were run at 400 MHz in CDCl₃

Preparation 110: (3S)-1-[4-(6-Methoxypyridin-3-yl)-5-methyl-4H-1,2,4-triazol-3-yl]pyrrolidin-3-ol

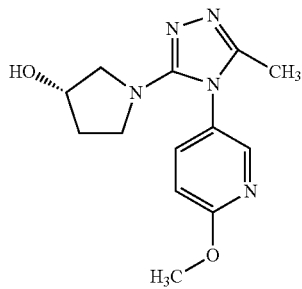 [SMILES: COc1ccc(-n2c(C)nnc2N2CC[C@H](O)C2)cn1]

The title compound was prepared from the product of preparation 102 and acetylhydrazide, using the same method as that described for preparation 4. The crude compound was triturated with pentane to afford the desired product in 44% yield. ¹H NMR (400 MHz, CD₃OD) δ: 1.78-1.87 (m, 1H), 1.90-2.02 (m, 1H), 2.15 (s, 3H), 3.03 (m, 1H), 3.18-3.30 (m, 3H), 4.01 (s, 3H), 4.33 (m, 1H), 6.98 (d, 1H), 7.78 (dd, 1H), 8.23 (m, 1H); LCMS m/z 276 [M+H]⁺

Preparation 111: 2-(Benzyloxy)-6-fluoropyridine

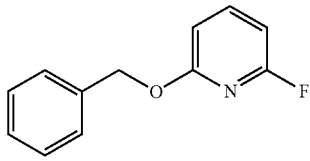 [SMILES: Fc1cccc(OCc2ccccc2)n1]

Benzylalcohol (1.88 g, 17.38 mmol) was added to a suspension of sodium hydride (60% dispersion in mineral oil, 458 mg, 19.11 mmol) in tetrahydrofuran (15 mL) and the mixture was heated to 50° C. for 45 minutes. The reaction mixture was then cooled to room temperature, a solution of 2,6-difluoropyridine (2 g, 17.38 mmol) in tetrahydrofuran (4 mL) was added dropwise and the mixture was stirred at room temperature for 45 minutes. The reaction mixture was then diluted with ethyl acetate, concentrated in vacuo and the residue was partitioned between ethyl acetate (50 mL) and water (20 mL). The organic layer was separated, washed with brine (20 mL), dried over magnesium sulfate and concentrated in vacuo. The residue was then concentrated in vacuo from dichloromethane to afford the title compound as a clear oil in 98% yield, 3.48 g. LRMS APCI m/z 204 [M+H]⁺

Preparation 112: tert-Butyl 4-{[6-(benzyloxy)pyridin-2-yl]oxy}piperidine-1-carboxylate

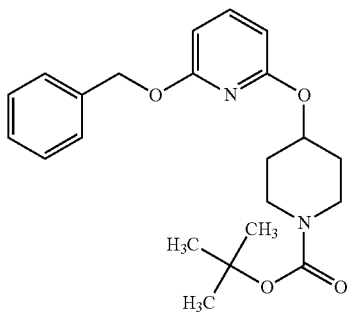 [SMILES: CC(C)(C)OC(=O)N1CCC(Oc2cccc(OCc3ccccc3)n2)CC1]

A solution of 1-boc-4-hydroxypiperidine (501 mg, 2.49 mmol) in tetrahydrofuran (10 mL) was added dropwise to a suspension of sodium hydride (60% dispersion in mineral oil, 65 mg, 2.74 mmol) and the mixture was heated at 55° C. for 1 hour. The reaction mixture was then cooled to room temperature, a solution of the product of preparation 111 (506 mg, 2.49 mmol) in tetrahydrofuran (3 mL) was added dropwise and the mixture was stirred at room temperature for 45 minutes and at 70° C. for 18 hours. The cooled reaction mixture was partitioned between ethyl acetate (20 mL) and water (10 mL), the organic layer was separated, washed with brine, dried over magnesium sulfate and concentrated in vacuo. Purification of the residue by column chromatography on silica gel, eluting with pentane:ethyl acetate, 100:0 to 90:10, afforded the title compound as a white solid in 49% yield, 470 mg. LRMS APCI m/z 385 [M+H]+

Preparation 113: tert-Butyl 4-[(6-oxo-1,6-dihydro-pyridin-2-yl)oxy]piperidine-1-carboxylate

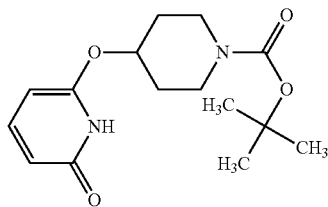 [SMILES: CC(C)(C)OC(=O)N1CCC(Oc2cccc(=O)[nH]2)CC1]

The title compound was prepared from the product of preparation 112, using the same method as that described for preparation 17, in 96% yield.
LRMS APCI m/z 295 [M+H]+

Preparation 114: tert-Butyl 4-[(1-methyl-6-oxo-1,6-dihydropyridin-2-yl)oxy]piperidine-1-carboxylate

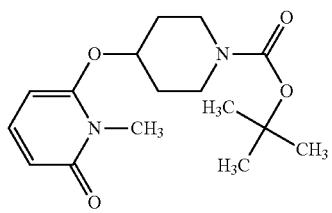 [SMILES: Cn1c(OC2CCN(C(=O)OC(C)(C)C)CC2)cccc1=O]

Sodium hydride (60% dispersion in mineral oil, 27 mg, 1.12 mmol) was added to a solution of the product of preparation 113 (276 mg, 0.93 mmol) in tetrahydrofuran (4 mL) and the mixture was stirred for 30 minutes at room temperature. Methyl p-toluenesulfonate (192 mg, 1.03 mmol) was then added and the mixture was stirred for a 18 hours at room temperature. Further methyl p-toluenesulfonate (87.3 mg, 0.47 mmol) was added and the mixture was stirred at room temperature for 72 hours. The reaction mixture was concentrated in vacuo and the residue was partitioned between ethyl acetate (10 mL) and water (5 mL). The organic layer was separated, washed with water and brine, dried over magnesium sulfate and concentrated in vacuo. Purification of the residue by column chromatography on silica gel, eluting with dichloromethane:methanol, 100:0 to 97:3 afforded the title compound in 59% yield, 170 mg.
LRMS APCI m/z 309 [M+H]+

Preparation 115: 1-Methyl-6-(piperidin-4-yloxy)pyridin-2(1H)-one hydrochloride

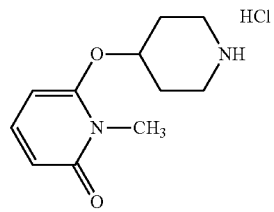

The title compound was prepared from the product of preparation 114, using the same method as that described for preparation 50, as a solid in quantitative yield.
LRMS APCI m/z 209 [M+H]+

Preparation 116: N-(6-Methoxypyridin-3-yl)-4-[(1-methyl-6-oxo-1,6-dihydropyridin-2-yl)oxy]piperidine-1-carbothioamide

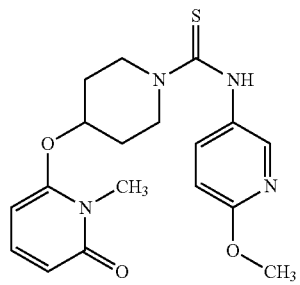 [SMILES: COc1ccc(NC(=S)N2CCC(Oc3cccc(=O)n3C)CC2)cn1]

The title compound was prepared from the product of preparation 115 and 5-isothiocyanato-2-methoxypyridine (*J. Org. Chem.* (1980), 45, 4219), using the same method as that described for preparation 35, in 50% yield.
LRMS APCI m/z 375 [M+H]+

Preparation 117: 1-[5-Methoxymethyl-4-(6-methoxy-pyridin-3-yl)-4H-[1,2,4]triazol-3-yl]pyrrolidin-3-ol

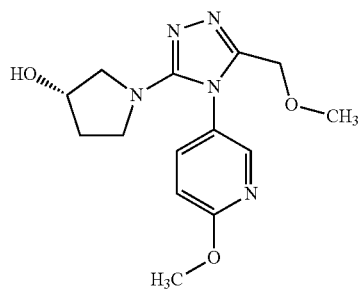 [SMILES: COCc1nnc(N2CC[C@H](O)C2)n1-c1ccc(OC)nc1]

The title compound was prepared from the product of preparation 102 and the compound of preparation 5, using the same method as that described for preparation 4. The crude compound was triturated with pentane to afford the desired product in 58% yield. LCMS m/z 306 [M+H]⁺

Preparation 118: 1-[5-Methoxymethyl-4-(6-methoxy-pyridin-3-yl)-4H-[1,2,4]triazol-3-yl]-azetidin-3-ol

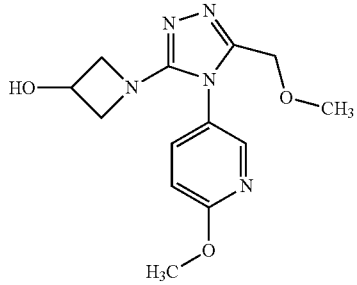 [SMILES: COCc1nnc(N2CC(O)C2)n1-c1ccc(OC)nc1]

The title compound was prepared from the compound of preparation 6, using the same method as that described for preparation 82, in 68% yield.
LRMS ESI m/z 292 [M+H]⁺

EXAMPLE 1: 5-{3-[3-(4-FLUOROPHENOXY)AZETIDIN-1-YL]-5-METHYL-4H-1,2,4-TRIAZOL-4-YL}-2-METHOXYPYRIDINE

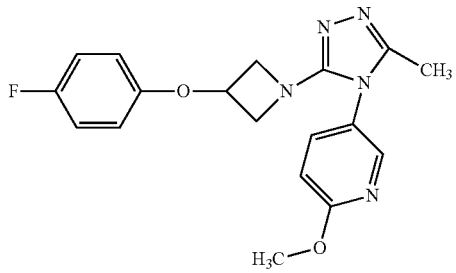 [SMILES: COc1ccc(-n2c(C)nnc2N2CC(Oc3ccc(F)cc3)C2)cn1]

Sodium hydride (60% dispersion in mineral oil, 12 mg, 0.3 mmol) was added to a solution of 4-fluorophenol (33 mg, 0.3 mmol) in N,N-dimethylformamide (2 mL) and the mixture was stirred at room temperature until effervescence had ceased. The product of preparation 4 (50 mg, 0.15 mmol) was then added and the mixture was heated at 100° C. for 40 hours. The cooled reaction mixture was then partitioned between water and dichloromethane and the organic layer was separated and concentrated in vacuo. The residue was purified by column chromatography on silica gel, eluting with dichloromethane:methanol, 100:0 to 95:5, to afford the title compound in 41% yield, 21.8 mg. ¹H NMR (400 MHz, CDCl₃) δ: 2.18 (s, 3H), 3.91 (m, 2H), 3.99 (s, 3H), 4.12 (m, 2H), 4.84 (m, 1H), 6.63 (m, 2H), 6.91 (m, 3H), 7.50 (dd, 1H), 8.10 (d, 1H); LRMS ESI m/z 356 [M+H]⁺

EXAMPLES 2 TO 31

The following compounds, of the general formula shown below, were prepared using the same method to that described for example 1, using either the product of preparation 4 (examples 2-14) or the product of preparation 6 (15-31) and commercially available phenols or compounds known in the literature as outlined below.

| No. | X'$_n$ | R² | Data (LRMS* and/or ¹H NMR) | Yield |
|---|---|---|---|---|
| 2 | 3-OCH₃ | H | δ: 2.18(s, 3H), 3.76(s, 3H), 3.91(m, 2H), 3.99(s, 3H), 4.18(m, 2H), 4.88(m, 1H), 6.23(m, 2H), 6.52(dd, 1H), 6.88(d, 1H), 7.16(m, 1H), 7.54(dd, 1H), 8.13(d, 1H); ESI m/z 367 [M + H]⁺ | 27% |
| 3 | 2-CH₃, 4-CN | H | δ: 1.77(s, 3H), 2.10(s, 3H), 3.96(m, 2H), 4.00(s, 3H), 4.16(m, 2H), 4.95(m, 1H), 6.40(d, 1H), 6.90(m, 1H), 7.39(m, 2H), 7.48(dd, 1H), 8.12(d, 1H); ESI m/z 376 [M + H]⁺ | 40% |
| 4 | 2-CH₃, 4-F | H | δ: 2.17(s, 3H), 2.20(s, 3H), 3.92(m, 2H), 3.99(s, 3H), 4.08(m, 2H), 4.83(m, 1H), 6.30(d, 1H), 6.74(m, 1H), 6.85(dd, 1H), 6.89(d, 1H), 7.49(dd, 1H), 8.12(d, 1H); ESI m/z 370 [M + H]⁺ | 45% |
| 5 | 4-CH₃ | H | δ: 2.18(s, 3H), 2.24(s, 3H), 3.93(m, 2H), 4.00(s, 3H), 4.11(m, 2H), 4.86(m, 1H), 6.58(m, 2H), 6.89(d, 1H), 7.03(d, 2H), 7.50(dd, 1H), 8.10(d, 1H); ESI m/z 352 [M + H]⁺ | 41% |
| 6 | 2-CH₃, 5-F | H | δ: 2.16(s, 3H), 2.21(s, 3H), 3.95(m, 2H), 4.02(s, 3H), 4.14(m, 2H), 4.84(m, 1H), 6.11(d, 1H), 6.57(m, 1H), 6.90(dd, 1H), 7.04(d, 1H), 7.49(dd, 1H), 8.12(d, 1H); ESI m/z 370 [M + H]⁺ | 35% |
| 7 | 4-Cl | H | δ: 2.19(s, 3H), 3.93(m, 2H), 4.00(s, 3H), 4.12(m, 2H), 4.84(m, 1H), 6.60(d, 2H), 6.87(d, 1H), 7.19(d, 2H), 7.48(dd, 1H), 8.10(d, 1H); ESI m/z 372 [M + H]⁺ | 23% |
| 8 | 3-F | H | ESI m/z 356 [M + H]⁺ | 35% |
| 9 | 3-F, 5-F | H | ESI m/z 374 [M + H]⁺ | 10% |
| 10 | 2-Cl | H | δ: 2.20(s, 3H), 4.00(m, 5H), 4.16(m, 2H), 4.94(m, 1H), 6.53(d, 1H), 6.90(m, 2H), 7.14(m, 1H), 7.35(d, 1H), 7.52(dd, 1H), 8.11(d, 1H); ESI m/z 372 [M + H]⁺ | 32% |
| 11 | 2-CN | H | ESI m/z 363 [M + H]⁺ | 31% |
| 12 | 2-Cl, 4-F | H | δ: 2.20(s, 3H), 4.02(m, 5H), 4.14(m, 2H), 4.88(m, 1H), 6.53(d, 1H), 6.88(m, 2H), 7.11(m, 1H), 7.52(dd, 1H), 8.13(d, 1H); ESI m/z 390 [M + H]⁺ | 20% |
| 13 | 2-F, 6-F | H | ESI m/z 374 [M + H]⁺ | 27% |
| 14 | 2-F, 4-F | H | ESI m/z 374 [M + H]⁺ | 54% |
| 15 | 3-F, 4-F | OCH₃ | δ: 3.27(s, 3H), 3.94(m, 2H), 4.01(s, 3H), 4.18(m, 2H), 4.32(s, 2H), 4.85(m, 1H), 6.38(m, 1H), 6.54(m, 1H), 6.85(d, 1H), 7.03(m, 1H), 7.59 (dd, 1H), 8.10(d, 1H); LCMS m/z 368 [M + H]⁺ | 48% |
| 16 | 3-CH₃ | OCH₃ | δ: 2.17(s, 3H), 3.30(s, 3H), 3.97(m, 2H), 4.00(s, 3H), 4.18(m, 2H), 4.32(s, 2H), 4.90(m, 1H), 6.45(m, 2H), 6.52(dd, 1H), 6.78(d, 1H), 7.14(m, 1H), 7.59(dd, 1H), 8.21(d, 1H); ESI m/z 382 [M + H]⁺ | 53% |
| 17 | 3-OCH₃ | OCH₃ | δ: 3.28(s, 3H), 3.76(s, 3H), 3.94(m, 2H), 3.99(s, 3H), 4.16(m, 2H), 4.31(s, 2H), 4.90(m, 1H), 6.23(m, 2H), 6.53(dd, 1H), 6.85(d, 1H), 7.14(m, 1H), 7.58(dd, 1H), 8.19(d, 1H); ESI m/z 398 [M + H]⁺ | 54% |
| 18 | 3-Cl | OCH₃ | δ: 3.27(s, 3H), 3.95(m, 2H), 3.99(s, 3H), 4.22(m, 2H), 4.31(s, 2H), 4.92(m, 1H), | 38% |

-continued

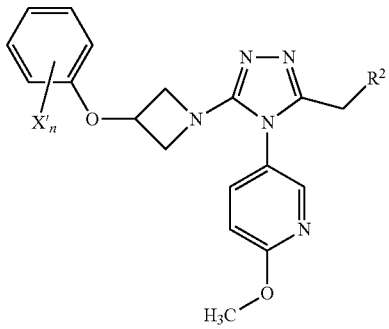

| No. | X'$_n$ | R² | Data (LRMS* and/or ¹H NMR) | Yield |
|---|---|---|---|---|
| 19 | 3-CF₃ | OCH₃ | 6.56(dd, 1H), 6.68(m, 1H), 6.86(d, 1H), 6.95(dd, 1H), 7.18(m, 1H), 7.64(dd, 1H), 8.02(d, 1H); ESI m/z 402 [M + H]⁺ δ: 3.30(s, 3H), 3.97(m, 2H), 3.99(s, 3H), 4.20(m, 2H), 4.32(m, 2H), 4.96(m, 1H), 6.85(m, 2H), 6.94(s, 1H), 7.25(m, 1H), 7.37(m, 1H), 7.60(dd, 1H) 8.22(d, 1H); ESI m/z 436 [M + H]⁺ | 57% |
| 20 | 3-F | OCH₃ | δ: 3.32(s, 3H), 3.97(m, 2H), 4.02(s, 3H), 4.18(m, 2H), 4.34(m, 2H), 4.95(m, 1H), 6.42(m, 1H), 6.44(m, 1H), 6.68(m, 1H), 6.86(d, 1H), 7.19(m, 1H), 7.60(dd, 1H), 8.21(d, 1H); ESI m/z 408 [M + Na] | 49% |
| 21 | 4-F | OCH₃ | δ: 3.29(s, 3H), 3.96(m, 2H), 3.99(s, 3H), 4.14(m, 2H), 4.32(m, 2H), 4.86(m, 1H), 6.62(m, 2H), 6.85(d, 1H), 6.92(m, 2H), 7.59(dd, 1H), 8.19(d, 1H); ESI m/z 386 [M + H]⁺ | 51% |
| 22 | 2-Cl | OCH₃ | δ: 3.30(s, 3H), 3.99(s, 3H), 4.05(dd, 2H), 4.18(dd, 2H), 4.32(s, 2H), 4.95(m, 1H), 6.52(m, 1H), 6.86(d, 1H), 6.92(m, 1H), 7.15(m, 1H), 7.36(dd, 1H), 7.60(dd, 1H), 8.21(d, 1H); APCl m/z 402/404 [M + H]⁺ | 48% |
| 23 | 2-CN | OCH₃ | APCl m/z 393 [M + H]⁺ | 70% |
| 24 | 2-F, 4-F | OCH₃ | APCl m/z 404 [M + H]⁺ | 53% |
| 25 | 2-Cl, 4-F | OCH₃ | δ: 3.29(s, 3H), 3.99(s, 3H), 4.05(dd, 2H), 4.24(dd, 2H), 4.31(s, 2H), 4.92(m, 1H), 6.50(m, 1H), 6.77(m, 1H), 6.87(d, 1H), 7.12(dd, 1H), 7.65(dd, 1H), 8.22(d, 1H); APCl m/z 420/422 [M + H]⁺ | 28% |
| 26 | 2-F, 6-F | OCH₃ | APCl m/z 404 [M + H]⁺ | 83% |
| 27 | 2-CH₃, 5-Cl, | OCH₃ | δ: 2.13(s, 3H), 3.29(s, 3H), 3.99(dd, 2H), 4.00(s, 3H), 4.23(dd, 2H), 4.31(s, 2H), 4.91(m, 1H), 6.34(d, 1H), 6.84(dd, 1H), 6.88(d, 1H), 7.03(d, 1H), 7.64(d, 1H), 8.22(d, 1H); APCl m/z 416/418 [M + H]⁺ | 57% |
| 28 | 2-CH₃, 3-CH₃ | OCH₃ | δ: 2.10(s, 3H), 2.24(s, 3H), 3.29(s, 3H), 3.99-4.01(m, 5H), 4.19(dd, 2H), 4.31(s, 2H), 4.90(m, 1H), 6.23(d, 1H), 6.78(d, 1H), 6.86(d, 1H), 6.96(m, 1H), 7.61(dd, 1H), 8.20(d, 1H); APCl m/z 396 [M + H]⁺ | 70% |
| 29 | 2-CH₃, 6-CH₃ | OCH₃ | δ: 2.15(s, 6H), 3.29(s, 3H), 4.00(s, 3H), 4.06(dd, 2H), 4.13(dd, 2H), 4.31(s, 2H), 4.57(m, 1H), 6.85-6.92(m, 1H), 6.95-6.99(m, 2H), 7.63(dd, 1H), 8.22(d, 1H); APCl m/z 396 [M + H]⁺ | 45% |
| 30 | 2-CH₂CH₃ | OCH₃ | δ: 1.16(t, 3H), 2.60(q, 2H), 3.29(s, 3H), 3.98-4.00(m, 5H), 4.22(dd, 2H), 4.31(s, 2H), 4.95(m, 1H), 6.38(d, 1H), 6.86(d, 1H), 6.90(m, 1H), 7.07(m, 1H), 7.14(m, 1H), 7.63(dd, 1H), 8.21(d, 1H); APCl m/z 396 [M + H]⁺ | 70% |
| 31 | 2-CH₃, 3-OCH₃ | OCH₃ | APCl m/z 412 [M + H]⁺ | 76% |

NMR spectra were run at 400 MHz in CDCl₃; *except example 15 (LCMS)

Example 3: 4-hydroxy-3-methyl-benzonitrile can be prepared as described in *J. Med. Chem.*; 1999, 42, 3572

Example 31: 3-methoxy-2-methyl-phenol can be prepared as described in *J. Org. Chem.*, 1990, 55(5), 1466-71

EXAMPLE 25A (CRYSTALLISATION OF EXAMPLE 25)

The compound of Example 25 was dissolved in hot ethyl acetate and allowed to cool, with gentle stirring, to room temperature. The crystalline material was isolated by filtration.

Single Crystal X-Ray Diffraction Experimental

The crystal structure was determined by Single Crystal X-Ray diffraction at room temperature and ambient relative humidity using a Bruker SMART APEX Single Crystal X-Ray diffractometer and Mo Kα radiation. Intensities were integrated (SMART v5.622 (control) and SAINT v6.02 (integration) software, Bruker AXS Inc., Madison, Wis. 1994) from several series of exposures where each exposure covered 0.3° in ω, with an exposure time of 30 s and the total data set was more than a sphere. Data were corrected for absorption using the multiscans method (SADABS, Program for scaling and correction of area detector data, G. M. Sheldrick, University of Göttingen, 1997 (based on the method of R. H. Blessing, *Acta Cryst.* 1995, A51, 33-38)).

The crystal structure was successfully solved by direct methods using SHELXS-97 (SHELXS-97, Program for crystal structure solution. G. M. Sheldrick, University of Göttingen, Germany, 1997, release 97-2), in Space Group P $\bar{1}$ and refined by the method of least-squares using SHELXL-97 (SHELXL-97, Program for crystal structure refinement. G. M. Sheldrick, University of Göttingen, Germany, 1997, release 97-2), to a final refined R-Factor of 5.16% (I>3σI).

Powder X-Ray Diffraction

The X-ray diffraction data were collected at room temperature using a Bruker AXS D4 powder X-ray diffractometer (Cu Kα radiation) fitted with an automatic sample changer, a theta-theta goniometer, automatic beam divergence slits, a secondary monochromator and a scintillation counter. The powder was mounted on a 12 mm diameter a silicon wafer specimen holder. The sample was rotated while being irradiated with Copper Kα1 X-rays (wavelength=1.5406 Ångstroms) with the X-ray tube operated at 40 kV/40 mA. The analyses were performed with the goniometer running in continuous mode set for a 5 second count per 0.02° step over a two theta range of 2° to 55°. The PXRD pattern of Example 25A exhibited the following characteristic diffraction peaks

| 2θ ± 0.1 (/°) |
|---|
| 23.7 |
| 24.6 |
| 10.7 |
| 16.2 |
| 14.1 |
| 18.3 |
| 8.5 |

Calculation of the Powder X-Ray Diffraction Pattern from the Crystal Structure 2θ angles, d-spacings and relative intensities (Table I) were calculated from the single crystal structure of Example 25A using the "Reflex Powder Diffraction" module of Accelrys MS Modelling™ [version 3.0]. Pertinent simulation parameters were:
  Wavelength=1.5406 Å (Cu Kα)
  Polarisation Factor=0.5
  Pseudo-Voigt Profile (U=0.01, V=−0.001, W=0.002)

The calculated pattern represents that of a pure phase of Example 25A since it is derived from a single crystal structure. A comparison of the measured and calculated patterns is shown in FIGURE I and demonstrates that the bulk is represented by the single crystal structure. Slight discrepancies between peak intensities can be attributed to preferred orientation effects in the measured pattern.

| 2θ (/°) | d-spacing (/Å) | Relative Intensity (%) |
|---|---|---|
| 23.665 | 3.75659 | 100.0 |
| 24.630 | 3.61162 | 57.3 |
| 10.651 | 8.29949 | 54.1 |
| 16.233 | 5.45598 | 46.6 |
| 22.679 | 3.91773 | 46.1 |
| 14.081 | 6.28441 | 45.0 |
| 18.267 | 4.85284 | 45.0 |
| 26.797 | 3.32421 | 44.3 |
| 23.363 | 3.80449 | 43.5 |
| 21.032 | 4.22049 | 43.1 |
| 20.211 | 4.39022 | 38.8 |
| 8.537 | 10.34867 | 36.4 |
| 21.989 | 4.03895 | 36.4 |
| 24.423 | 3.64172 | 36.4 |
| 16.590 | 5.33939 | 35.1 |
| 27.952 | 3.18941 | 35.0 |
| 47.788 | 1.90176 | 35.0 |
| 32.790 | 2.72905 | 34.6 |
| 12.380 | 7.14378 | 34.2 |
| 15.518 | 5.70563 | 34.1 |
| 17.916 | 4.94700 | 34.1 |
| 31.339 | 2.85203 | 32.7 |
| 21.399 | 4.14897 | 32.0 |
| 26.443 | 3.36793 | 30.5 |
| 28.123 | 3.17044 | 29.9 |
| 17.543 | 5.05134 | 29.5 |
| 24.128 | 3.68558 | 29.0 |
| 27.188 | 3.27729 | 28.9 |
| 36.726 | 2.44512 | 28.2 |
| 43.671 | 2.07100 | 28.1 |
| 19.807 | 4.47873 | 27.7 |
| 13.309 | 6.64728 | 27.5 |
| 26.125 | 3.40815 | 27.4 |
| 35.806 | 2.50582 | 27.1 |
| 33.788 | 2.65067 | 26.9 |
| 42.356 | 2.13222 | 26.7 |
| 41.711 | 2.16367 | 26.4 |
| 17.151 | 5.16594 | 26.3 |
| 43.147 | 2.09496 | 26.3 |
| 34.291 | 2.61300 | 26.2 |
| 15.162 | 5.83898 | 26.1 |
| 31.085 | 2.87480 | 26.1 |
| 32.306 | 2.76883 | 26.1 |
| 50.445 | 1.80765 | 26.0 |
| 25.827 | 3.44685 | 25.9 |
| 49.156 | 1.85200 | 25.6 |
| 11.767 | 7.51482 | 25.5 |
| 38.739 | 2.32257 | 25.5 |
| 7.731 | 11.42585 | 24.5 |

EXAMPLE 32: 1-[5-ISOPROPYL-4-(6-METHOXYPYRIDIN-3-YL)-4H-1,2,4-TRIAZOL-3-YL]AZETIDIN-3-YL METHANESULFONATE

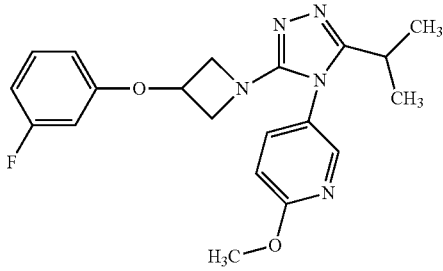 [SMILES: COc1ccc(-n2c(C(C)C)nnc2N2CC(Oc3cccc(F)c3)C2)cn1]

The title compound was prepared from the product of preparation 7 and 3-fluorophenol, using a similar method to that of example 1. After 16 hours (c.f. 40 hours in example 1), tlc analysis indicated that the reaction was complete, affording the desired product in 38% yield.

$^1$H NMR (400 MHz, CDCl$_3$) δ: 1.23 (d, 6H), 2.67 (m, 1H), 3.92 (m, 2H), 4.00 (s, 3H), 4.12 (m, 2H), 4.85 (m, 1H), 6.38 (d, 1H), 6.44 (dd, 1H), 6.66 (m, 1H), 6.91 (d, 1H), 7.18 (m, 1H), 7.49 (dd, 1H), 8.11 (d, 1H); LRMS ESI m/z 384 [M+H]$^+$

EXAMPLE 33: 3-{3-[3-(5-FLUOROPHENOXY)AZETIDIN-1-YL]-5-METHYL-4H-1,2,4-TRIAZOL-4-YL}-6-METHOXY-2-METHYLPYRIDINE

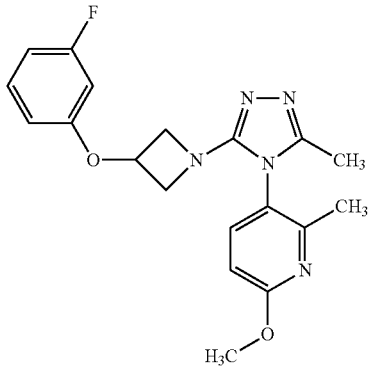 [SMILES: COc1ccc(-n2c(C)nnc2N2CC(Oc3cccc(F)c3)C2)c(C)n1]

Sodium hydride (60% dispersion in mineral oil, 22.4 mg, 0.56 mmol) was added to a solution of 5-fluorophenol (62.8 mg, 0.56 mmol) in N,N-dimethylformamide (2 mL) and the mixture was stirred at room temperature until effervescence had ceased. The product of preparation 16 (100 mg, 0.28 mmol) was then added and the mixture was heated at 100° C. for 18 hours. Further sodium hydride (60% dispersion in mineral oil, 11.2 mg, 0.28 mmol) and 5-fluorophenol (31.4 mg, 0.28 mmol) was then added and heating continued for a further 24 hours. The cooled reaction mixture was then diluted with water (20 mL) and brine (40 mL) and was extracted with ethyl acetate (2×30 mL). The combined organic solution was then magnesium sulfate and concentrated in vacuo. The residue was purified by column chromatography on silica gel, eluting with dichloromethane:methanol, 100:0 to 95:5, to afford the title compound in 27% yield, 30 mg. ¹H NMR (CDCl₃, 400 MHz) δ: 2.15 (s, 3H), 2.24 (s, 3H), 3.92 (m, 2H), 3.98 (s, 3H), 4.14 (m, 1H), 4.19 (m, 1H), 4.90 (m, 1H), 6.40 (m, 1H), 6.44 (d, 1H), 6.70 (m, 2H), 7.20 (m, 1H), 7.41 (d, 1H); LRMS ESI⁺ m/z 369 [M+H]⁺

EXAMPLE 34: 3-{3-[3-(4-FLUORO-2-METHYL-PHENOXY)AZETIDIN-1-YL]-5-METHYL-4H-1,2,4-TRIAZOL-4-YL}-6-METHOXY-2-METHYL-PYRIDINE

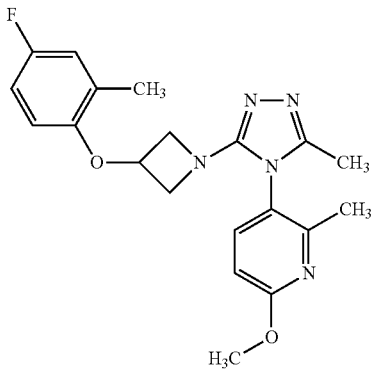 [SMILES: COc1ccc(-n2c(C)nnc2N2CC(Oc3ccc(F)cc3C)C2)c(C)n1]

The title compound was prepared from the product of preparation 16 and 4-fluoro-3-methylphenol, using the same method as that described for example 33, in 34% yield.

¹H NMR (CDCl₃, 400 MHz) δ: 2.13 (s, 3H), 2.18 (s, 3H), 2.24 (s, 3H), 3.91 (m, 1H), 3.96 (m, 1H), 3.99 (s, 3H), 4.04 (m, 1H), 4.14 (m, 1H), 4.85 (m, 1H), 6.32 (m, 1H), 6.75 (m, 2H), 6.84 (m, 1H), 7.39 (d, 1H); LRMS ESI⁺ m/z 383 [M+H]⁺

EXAMPLE 35: 5-{3-[3-(3-FLUOROPHENOXY)-3-METHYLAZETIDIN-1-YL]-5-METHYL-4H-1,2,4-TRIAZOL-4-YL}-2-METHOXYPYRIDINE

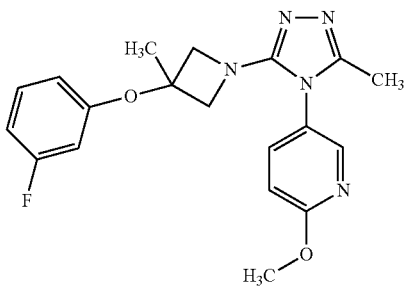 [SMILES: COc1ccc(-n2c(C)nnc2N2CC(C)(Oc3cccc(F)c3)C2)cn1]

A solution of the product of preparation 12 (75 mg, 0.2 mmol), acetylhydrazide (44.4 mg, 0.6 mmol) in ethanol (3 mL) was heated over 4 Å molecular sieves, at 50° C. for 18 hours. The reaction mixture was then concentrated in vacuo and the residue was purified by column chromatography on silica gel, eluting with dichloromethane:methanol, 100:0 to 95:5, to afford the title compound in 26% yield. ¹H NMR (CDCl₃, 400 MHz) δ: 1.65 (s, 3H), 2.21 (s, 3H), 3.82 (d, 2H), 4.04 (s, 3H), 4.18 (d, 2H), 6.40 (m, 2H), 6.66 (t, 1H), 6.92 (d, 1H), 7.19 (m, 1H), 7.59 (m, 1H), 8.16 (d, 1H); LRMS ESI⁺ m/z 369 [M+H]⁺

EXAMPLE 36: 5-[3-[3-(3-FLUOROPHENOXY)-3-METHYLAZETIDIN-1-YL]-5-(METHOXYMETHYL)-4H-1,2,4-TRIAZOL-4-YL]-2-METHOXY-PYRIDINE

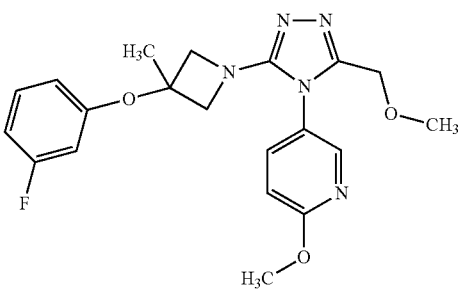 [SMILES: COCc1nnc(N2CC(C)(Oc3cccc(F)c3)C2)n1-c1ccc(OC)nc1]

The title compound was prepared from the products of preparations 12 and 5, using the same method as that described for example 35, in 27% yield. ¹H NMR (CDCl₃, 400 MHz) δ: 1.63 (s, 3H), 3.30 (s, 3H), 3.84 (d, 2H), 3.99 (s, 3H), 4.18 (d, 2H), 4.30 (s, 2H), 6.38 (m, 2H), 6.65 (t, 1H), 6.86 (d, 1H), 7.17 (m, 1H), 7.62 (m, 1H), 8.21 (d, 1H); LRMS ESI⁺ m/z 400 [M+H]⁺

EXAMPLE 37: 5-{3-[4-(3,4-DIFLUOROPHENOXY)PIPERIDIN-1-YL]-5-METHYL-4H-1,2,4-TRIAZOL-4-YL}-2-METHOXYPYRIDINE

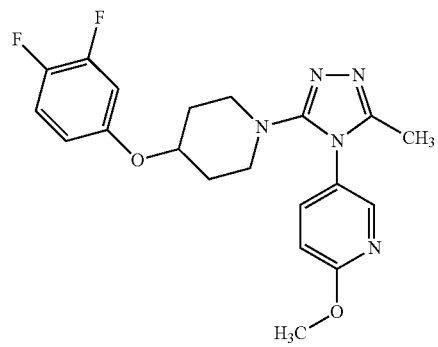 [SMILES: COc1ccc(-n2c(C)nnc2N2CCC(Oc3ccc(F)c(F)c3)CC2)cn1]

The product of preparation 21 (67.4 mg, 0.23 mmol) and 3,4-difluorophenol (50.85 mg, 0.47 mmol) were added to mixture of polymer supported triphenylphosphine (403 mg, 0.61 mmol) and di-tert-butyl azodicarboxylate (107 mg, 0.47 mmol) in dichloromethane (2 mL) and the mixture was stirred at room temperature for 4 hours. Trifluoroacetic acid (0.78 mL) was then added and the mixture was stirred for a further hour. The reaction mixture was basified with 2M sodium hydroxide solution (5 mL) and the organic layer was separated and concentrated in vacuo. Purification of the residue by HPLC using a Phenomenex Luna C18 system, eluting with water/acetonitrile/trifluoroacetic acid (5:95:0.1):acetonitrile, 95:5 to 5:95, afforded the title compound as a gum in 32% yield, 29.8 mg. ¹H NMR (CDCl₃, 400 MHz) δ: 1.69-1.80 (m, 2H), 1.89-1.95 (m, 2H), 2.31 (s, 3H), 3.02-3.12 (m, 2H), 3.31-3.40 (m, 2H), 4.01 (s, 3H), 4.30-4.80 (m, 1H), 6.52-6.60 (m, 1H), 6.64-6.70 (m, 1H), 6.80 (d, 1H), 6.98-7.02 (m, 1H), 7.56 (dd, 1H), 8.08 (s, 1H); LRMS ESI m/z 402 [M+H]⁺

EXAMPLES 38 TO 53

The following compounds, of the general formula shown below, were prepared from the products of preparation 21 (examples 38-45) and preparation 42 (examples 39-53) and the appropriate commercial phenol or phenol known in the literature as outlined below, using the same method to that described example 37.

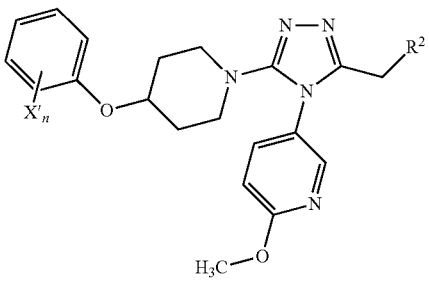

| No. | X'$_n$ | R$^2$ | Data (LRMS* and/or $^1$H NMR) | Yield |
|---|---|---|---|---|
| 38 | 2-CH$_3$, 6-CH$_3$ | H | δ: 1.69-1.80 (m, 2H), 1.88-1.97 (m, 2H), 2.03 (s, 6H), 2.09 (s, 3H), 2.85-2.96 (m, 2H), 3.38-3.45 (m, 2H), 3.82-3.91 (m, 1H), 4.01 (s, 3H), 6.87-7.01 (m, 4H), 7.59 (d, 1H), 8.18 (s, 1H); APCI m/z 394 [M + H]$^+$ | 10% |
| 39 | 2-CH$_3$, 3-OCH$_3$ | H | δ: 1.71-1.81 (m, 2H), 1.86-1.97 (m, 2H), 2.07 (s, 3H), 2.25 (s, 3H), 3.00-3.10 (m, 2H), 3.00-3.39 (m, 2H), 3.80 (s, 3H), 4.00 (s, 3H), 4.36-4.42 (m, 1H), 6.46-6.51 (m, 2H), 6.90 (d, 1H), 7.01-7.10 (m, 1H), 7.59 (dd, 1H), 8.16 (m, 1H); APCI m/z 410 [M + H]$^+$ | 36% |
| 40 | H | H | δ: 1.68-1.76 (m, 2H), 1.89-1.96 (m, 2H), 2.25 (s, 3H), 2.97-3.03 (m, 2H), 3.30-3.36 (m, 2H), 3.99 (s, 3H), 4.37-4.42 (m, 1H), 6.85-6.94 (m, 4H), 7.22-7.27 (m, 2H), 7.54 (dd, 1H), 8.12 (m, 1H); APCI m/z 366 [M + H]$^+$ | 22% |
| 41 | 2-F, 3-F | H | APCI m/z 402 [M + H]$^+$ | 19% |
| 42 | 3-F, 5-F | H | HRMS m/z found 402.1736; C$_{20}$H$_{21}$F$_2$N$_5$O$_2$ requires 402.1726 [M + H]$^+$ | 7% |
| 43 | 2-CH$_3$, 4-F | H | HRMS m/z found 398.1967; C$_{21}$H$_{24}$FN$_5$O$_2$ requires 398.1987 [M + H]$^+$ | 18% |
| 44 | 2 CH$_3$, 5-CN | H | HRMS m/z found 405.2034; C$_{22}$H$_{24}$N$_6$O$_2$ requires 405.2017 [M + H]$^+$ | 15% |
| 45 | 2 CH$_3$, 3-F | H | HRMS m/z found 398.1974; C$_{21}$H$_{24}$FN$_5$O$_2$ requires 398.1987 [M + H]$^+$ | 14% |
| 46 | 2-CH$_3$, 5-CN | OCH$_3$ | ESI m/z 435 [M + H]$^+$ | 5% |
| 47 | 2-CH$_3$, 5-F | OCH$_3$ | ESI m/z 428 [M + H]$^+$ | 7% |
| 48 | 2-CH$_3$, 3-F | OCH$_3$ | ESI m/z 428 [M + H]$^+$ | 5% |
| 49 | 2-CH$_3$, 4-F | OCH$_3$ | ESI m/z 428 [M + H]$^+$ | 13% |
| 50 | 2-CH$_3$, 5-OCH$_3$ | OCH$_3$ | ESI m/z 439 [M + H]$^+$ | 7% |
| 51 | 2-CH$_3$, 4-CN | OCH$_3$ | ESI m/z 435 [M + H]$^+$ | 7% |
| 52 | 3-F, 5-F | OCH$_3$ | ESI m/z 432 [M + H]$^+$ | 12% |
| 53 | 3-F, 4-F | OCH$_3$ | δ: 1.71-1.81 (m, 2H), 1.90-1.99 (m, 2H), 3.14-3.22 (m, 2H), 3.31 (s, 3H), 3.39-3.48 (m, 2H), 4.00 (s, 3H), 4.30-4.39 (m, 3H), 6.58 (m, 1H), 6.63-6.69 (m, 1H), 6.80 (d, 1H), 7.00-7.09 (m, 1H), 7.77 (dd, 1H), 8.29 (m, 1H); ESI m/z 432 [M + H]$^+$ | 21% |

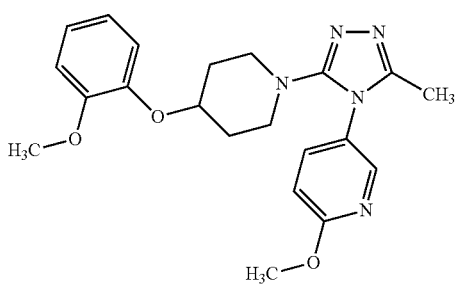

NMR spectra were run at 400 MHz in CDCl3;
*except examples 42-45 (HRMS)

Example 40: diisopropyl azodicarboxylate used instead of di-tert-butyl azodicarboxylate Examples 43: crude products were purified by HPLC using a Phenomenex Luna C18 system, eluting with 0.1% formic acid (aqueous):0.1% formic acid/acetonitrile, 100:0 to 2:98.

Example 44: 3-hydroxy-4-methyl-benzonitrile can be prepared as described in WO 96/24609, p20

Example 45: 3-fluoro-2-methyl-phenol can be prepared as described EP 511036, p32

Examples 46-52: crude compounds were purified by HPLC using a Phenomenex Luna C18 system, eluting with 0.1% formic acid (aqueous):0.1% formic acid/acetonitrile, 100:0 to 2:98.

EXAMPLE 54: 2-METHOXY-5-{3-[4-(2-METHOXYPHENOXY)PIPERIDIN-1-YL]-5-METHYL-4H-1,2,4-TRIAZOL-4-YL}PYRIDINE

Diisopropylazodicarboxylate (176 μL, 0.69 mmol) in tetrahydrofuran (2 mL) was added to an ice-cooled mixture of the product of preparation 21 (200 mg, 0.69 mmol), 2-methoxyphenol (86 mg, 0.69 mmol) and polymer supported triphenylphosphine (238 mg, 0.83 mmol) in tetrahydrofuran (2 mL)/dichloromethane (0.6 mL) and the mixture was stirred at room temperature for 72 hours. The reaction mixture was then diluted with dichloromethane, basified with 2M sodium hydroxide solution and passed through a phase separation tube. The organic solution was concentrated in vacuo and the residue was purified by column chromatography on silica gel, eluting with dichloromethane:methanol:0.88 ammonia, 99:1:0.1 to 95:5:0.5. The appropriate fractions were evaporated under reduced pressure and the residue was further purified by HPLC using a Phenomenex Luna C18 system, eluting with water/acetonitrile/trifluoroacetic acid (5:95:0.1):acetonitrile, 95:5 to 5:95. The appropriate fractions were evaporated under reduced pressure and the residue was washed with sodium hydrogen carbonate solution and extracted with dichloromethane. The organic solution was then dried over sodium sulfate and concentrated in vacuo to give an oil. Trituration of the oil afforded the title compound as a solid in 21% yield, 58 mg. $^1$H NMR (CDCl$_3$, 400 MHz) δ: 1.70-1.79 (m, 2H), 1.90-1.97 (m, 2H), 2.25 (s, 3H), 2.94-3.00 (m, 2H), 3.34-3.40 (m, 2H), 3.82 (s, 3H), 4.00 (s, 3H), 4.29-4.35 (m, 1H), 6.82-6.96 (m, 5H), 7.55 (dd, 1H), 8.12 (m, 1H); LRMS APCI m/z 396 [M+H]$^+$ EXAMPLE 55: 3-({1-[4-(6-METHOXYPYRIDIN-3-YL)-5-METHYL-4H-1,2,4-TRIAZOL-3-YL]PIPERIDIN-4-YL}OXY)-2-METHYLPYRIDINE

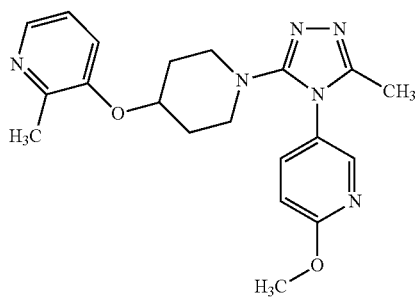 [SMILES: COc1ccc(-n2c(C)nnc2N2CCC(Oc3cccnc3C)CC2)cn1]

Potassium tert-butoxide (31 mg, 0.28 mmol) was added to a solution of the product of preparation 24 (90.1 mg, 0.25 mmol) in tetrahydrofuran (3 mL) and the reaction was stirred at room temperature for 30 minutes. Methyl p-toluenesulfonate (51.4 mg, 0.28 mmol) was then added and the mixture was stirred for 3 hours. The reaction mixture was then concentrated in vacuo and re-dissolved in dichloromethane. The organic solution was washed with sodium hydrogen carbonate solution, dried over magnesium sulfate and concentrated in vacuo. The residue was re-dissolved in tetrahydrofuran (3 mL) and trifluoroacetic acid (one drop) and acethydrazide (42 mg, 0.56 mmol) was added and the mixture was heated under reflux for 4 hours. The reaction mixture was then concentrated in vacuo and re-dissolved in dichloromethane. The organic solution was washed with sodium hydrogen carbonate solution and brine, dried over magnesium sulfate and concentrated in vacuo to give an oil. The oil was purified by column chromatography on silica gel, eluting with dichloromethane:methanol, 90:10, to afford the title compound as a red oil in 52% yield, 46.5 mg. $^1$H NMR (DMSO-d$_6$, 400 MHz) δ: 1.69-1.81 (m, 2H), 1.90-2.02 (m, 2H), 2.25 (s, 3H), 2.50 (s, 3H), 3.00-3.10 (m, 2H), 3.30-3.39 (m, 2H), 4.00 (s, 3H), 4.40 (m, 1H), 6.90 (d, 1H), 7.12 (m, 2H), 7.55 (d, 1H), 8.10 (m, 1H), 8.15 (m, 1H); LRMS APCI m/z 381 [M+H]$^+$

EXAMPLES 56 TO 63

The following compounds, of the general formula shown below, were prepared using the same method to that described for example 55. The products of preparations 37, 47 and 51 were treated with acethydrazide to afford examples 56 to 58. Likewise, the products of preparations 35, 37, 47, 48 and 51 were treated with 2-methoxyacetylhydrazide (preparation 5) to afford examples 59 to 63.

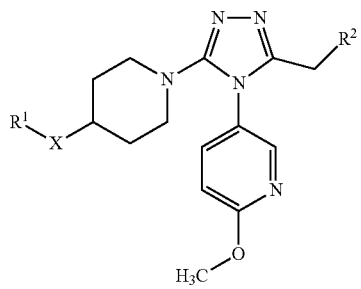

| No. | R$^1$ | R$^2$ | X | Data (LRMS* and/or $^1$H NMR | Yield |
|---|---|---|---|---|---|
| 56 | 3-methylpyridin-4-yl | H | O | δ: 1.72-1.82 (m, 2H), 1.92-2.00 (m, 2H), 2.15 (s, 3H), 2.26 (s, 3H), 3.02-3.09 (m, 2H), 3.29-3.37 (m, 2H), 3.98 (s, 3H), 4.52-4.59 (m, 1H), 6.65 (d, 1H), 6.91 (d, 1H), 7.75 (d, 1H), 8.16 (m, 1H), 8.22-8.31 (m, 2H); APCI m/z 381 [M + H]$^+$ | 7% |
| 57 | 2-chlorophenyl | H | O | δ: 1.75-1.85 (m, 2H), 1.90-2.05 (m, 2H), 2.25 (s, 3H), 3.05-3.15 (m, 2H), 3.35-3.45 (m, 2H), 4.00 (s, 3H), 4.40-4.50 (m, 1H), 6.85-6.95 (m, 3H), 7.15-7.20 (m, 1H), 7.30-7.35 (d, 1H) (7.57-7.62 (m, 1H), 8.15 (s, 1H); APCI m/z 400 [M + H]$^+$ | 55% |

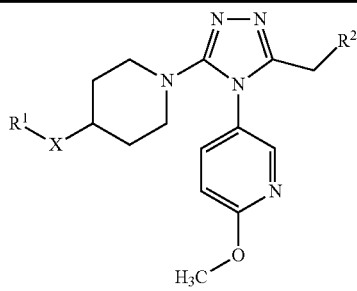

| No. | R¹ | R² | X | Data (LRMS* and/or ¹H NMR | Yield |
|---|---|---|---|---|---|
| 58 | 2-pyridyl | H | NCH₃ | APCI m/z 380 [M + H]⁺ | 52% |
| 59 | 2-methylphenyl | OCH₃ | O | δ: 1.75-1.82 (m, 2H), 1.89-1.99 (m, 2H), 2.20 (s, 3H), 3.02-3.09 (m, 2H), 3.30-3.41 (m, 5H), 3.99 (s, 3H), 4.32 (s, 3H), 4.40-4.45 (m, 1H), 6.78-6.85 (m, 3H), 7.08-7.15 (m, 2H), 7.65 (dd, 1H), 8.25 (m, 1H); APCI m/z 410 [M + H]⁺ | 48% |
| 60 | 3-methyl-4-pyridyl | OCH₃ | O | δ: 1.77-1.86 (m, 2H), 1.93-2.01 (m, 2H), 2.15 (s, 3H), 2.06 (s, 3H), 3.06-3.15 (m, 2H), 3.22-3.40 (m, 5H), 3.99 (s, 3H), 4.36 (s, 2H), 6.63 (d, 1H), 6.89 (d, 1H), 7.64 (d, 1H), 8.23-8.31 (m, 3H); APCI m/z 411 [M + H]⁺ | 54% |
| 61 | 2-chlorophenyl | OCH₃ | O | δ: 1.80-1.90 (m, 2H), 1.95-2.05 (m, 2H), 3.12-3.22 (m, 2H), 3.32 (s, 3H), 3.40-3.50 (m, 2H), 4.00 (s, 3H), 4.35 (s, 2H), 4.45-4.55 (m, 1H), 6.85-6.95 (m, 3H), 7.15-7.20 (m, 1H), 7.35-7.38 (m, 1H), 7.70-7.75 (m, 1H), 8.27 (s, 1H); APCI m/z 430 [M + H]⁺ | 30% |
| 62 | 3,5-difluorophenyl | OCH₃ | O | δ: 1.75-1.85 (m, 2H), 1.92-2.04 (m, 2H), 3.18-3.09 (m, 2H), 3.32 (s, 3H), 3.40-3.49 (m, 2H), 4.00 (s, 3H), 4.35 (s, 2H), 4.39-4.44 (m, 1H), 6.35-6.44 (m, 3H), 6.92 (d, 1H), 6.88 (m, 1H), 7.78 (m, 1H), 8.29 (m, 1H); ESI m/z 432 [M + H]⁺ | 58% |
| 63 | 2-pyridyl | OCH₃ | NCH₃ | APCI m/z 410 [M + H]⁺ | 25% |

NMR spectra were run at 400 MHz in CDCl₃ or DMSO-d₆ (examples 56 and 60)

Example 58: further trifluoroacetic acid (few drops) and 2.0 eq acethydrazide after heating under reflux for 2 hours.

Example 63: further trifluoroacetic acid (few drops) and 2.0 eq 2-methoxyacetylhydrazide (preparation 5) after heating under reflux for 2 hours.

EXAMPLES 64 TO 72

The following compounds, of the general formula shown below, were prepared using the same method to that described preparation 4. The products of preparations 38, 39, 41 58 and 61 were treated with acethydrazide to afford examples 64 to 68. Likewise, the products of preparation 38, 41 58 and 61 were treated with 2-methoxyacetylhydrazide (preparation 5) to afford examples 69 to 72.

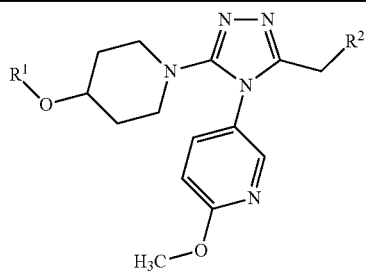

| No. | R² | R¹ | Data (LRMS and/or ¹H NMR) | Yield |
|---|---|---|---|---|
| 64 | 3-CH₃-pyridin-2-yl | H | ESI m/z 381 [M + H]⁺ | 53% |
| 65 | 2-CH₃-phenyl | H | APCI m/z 380 [M + H]⁺ | |
| 66 | 2,3-di-CH₃-pyridin-4-yl | H | APCI m/z 395 [M + H]⁺ | 20% |
| 67 | pyridin-4-yl | H | ESI m/z 367 [M + H]⁺ | 30% |
| 68 | 2-CN-phenyl | H | APSI m/z 391 [M + H]⁺ | 37% |
| 69 | 3-CH₃-pyridin-2-yl | OCH₃ | δ: 1.71-1.83 (m, 2H), 1.92-2.00 (m, 2H), 2.17 (s, 3H), 3.08-3.15 (m, 2H), 3.31-3.40 (m, 5H), 3.99 (s, 3H), 4.36 (s, 2H), 5.20-5.25 (m, 1H), 6.75 (m, 1H), 6.85 (m, 1H), 7.38 (m, 1H), 7.65 (dd, 1H), 7.92 (m, 1H), 8.27 (m, 1H); ESI m/z 411 [M + H]⁺ | 56% |
| 70 | 2,3-di-CH₃-pyridin-4-yl | OCH₃ | APCI m/z 425 [M + H]⁺ | 33% |
| 71 | pyridin-4-yl | OCH₃ | δ: 1.71-1.81 (m, 2H), 1.90-2.00 (m, 2H), 2.99-3.10 (m, 2H), 3.29 (s, 3H), 3.31-3.39 (m, 2H), 3.99 (s, 3H), 4.32 (s, 2H), 4.52-4.59 (m, 1H), 6.79-6.87 (m, 3H), 6.63 (m, 1H), 7.38 (m, 1H), 7.65 (dd, 1H), 7.92 (m, 1H), 8.22 (m, 1H), 8.38-8.45 (m, 1H); ESI m/z 397 [M + H]⁺ | 31% |
| 72 | 2-CN-phenyl | OCH₃ | APSI m/z 421 [M + H]⁺ | 67% |

NMR spectra were run at 400 MHz in CDCl₃

EXAMPLE 73: N-{1-[4-(6-METHOXYPYRIDIN-3-YL)-5-METHYL-4H-1,2,4-TRIAZOL-3-YL]PIPERIDIN-4-YL}-N-METHYLPYRIMIDIN-2-AMINE

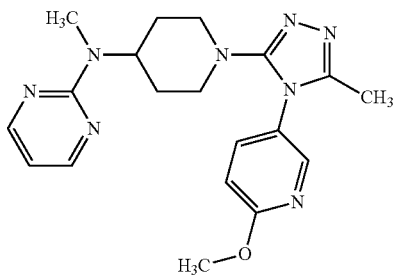 [SMILES: COc1ccc(-n2c(C)nnc2N2CCC(N(C)c3ncccn3)CC2)cn1]

A mixture of the product of preparation 57 (101 mg, 0.33 mmol), 2-chloropyrimidine (46 mg, 0.40 mmol) and N,N-diisopropylethylamine (87 μL, 0.5 mmol) in dimethylsulfoxide (2 mL) was heated at 100° C. for 2 hours. Further 2-chloropyrimidine (46 mg, 0.4 mmol) and N,N-diisopropylethylamine (87 μL, 0.5 mmol) were added and heating continued at 100° C. for 4 hours and at 120° C. for 12 hours. The reaction mixture was then partitioned between dichloromethane and water and the organic layer was separated and washed with 10% citric acid (2×5 mL). The aqueous solution was basified with sodium hydrogen carbonate solution and extracted with dichloromethane (3×10 mL). The combined organic solution was dried over magnesium sulfate, concentrated in vacuo and the residue was purified by column chromatography on silica gel, eluting with dichloromethane:methanol:0.88 ammonia, 99:1:0.1 to 95:5:0.5, to afford the title compound as a foam in 56% yield, 70 mg. LRMS APCI 381 [M+H]$^+$

EXAMPLES 74 TO 108

The following compounds, of the general formula shown below, were prepared using the same method to that described for example 1, using either the product of preparation 4 (examples 74-91) or the product of preparation 6 (examples 92-108) with 3 to 5 equivalents of commercially available phenols or compounds known in the literature, as outlined below.

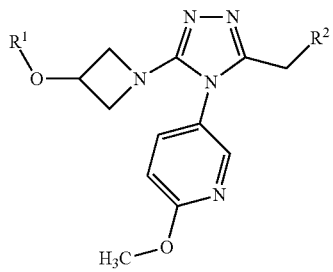

| No. | R$^1$ | R$^2$ | Data (LRMS and/or $^1$H NMR) | Yield |
|---|---|---|---|---|
| 74 | (1-methyl-3-(trifluoromethyl)pyrazol-5-yl) | H | ESI m/z 410 [M + H]$^+$ | 8% |
| 75 | (4-chloro-2-methylphenyl) | H | ESI m/z 386 [M + H]$^+$ | 33% |
| 76 | (2,3-dimethylphenyl) | H | δ: 2.04 (s, 3H), 2.13 (s, 3H), 2.20 (s, 3H), 3.97 (m, 2H), 4.00 (s, 3H), 4.14 (m, 2H), 4.86 (m, 1H), 6.25 (d, 1H), 6.78 (d, 1H), 6.89 (d, 1H), 6.95 (m, 1H), 7.53 (dd, 1H), 8.12 (d, 1H); ESI m/z 366 [M + H]$^+$ | 23% |
| 77 | (2,6-dimethylphenyl) | H | δ: 2.16 (s, 6H), 2.23 (s, 3H), 4.04 (m, 5H), 4.13 (m, 2H), 4.58 (m, 1H), 6.91 (m, 2H), 6.97 (m, 2H), 7.58 (dd, 1H), 8.15 (d, 1H); ESI m/z 366 [M + H]$^+$ | 19% |

-continued

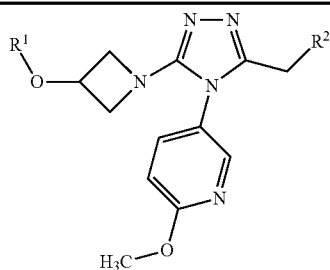

| No. | R¹ | R² | Data (LRMS and/or ¹H NMR) | Yield |
|---|---|---|---|---|
| 78 | 2-ethylphenyl | H | ESI m/z 366 [M + H]⁺ | 26% |
| 79 | 5-fluoro-2-ethylphenyl | H | δ: 1.16 (t, 3H), 2.20 (s, 3H), 2.57 (m, 2H), 3.94 (m, 2H), 4.03 (s, 3H), 4.12 (m, 2H), 4.86 (m, 1H), 6.34 (m, 1H), 6.73 (m, 1H), 6.86 (m, 2H), 7.50 (dd, 1H), 8.13 (d, 1H); ESI m/z 384 [M + H]⁺ | 26% |
| 80 | 4-fluoro-2-methylphenyl | H | δ: 2.18 (s, 3H), 4.00 (m, 5H), 4.15 (m, 2H), 4.88 (m, 1H), 6.23 (dd, 1H), 6.63 (m, 1H), 6.89 (d, 1H), 7.27 (m, 1H), 7.52 (dd, 1H), 8.13 (m, 1H); APCI m/z 390 [M + H]⁺ | 67% |
| 81 | 2-chloro-6-fluorophenyl | H | δ: 2.19 (s, 3H), 4.00 (m, 5H), 4.08 (m, 2H), 4.85 (m, 1H), 6.88 (d, 1H), 6.96 (m, 2H), 7.13 (m, 1H), 7.51 (dd, 1H), 8.11 (d, 1H); APCI m/z 390 [M + H]⁺ | 35% |
| 82 | 2-chloro-3,5-difluorophenyl | H | δ: 2.21 (s, 3H), 4.02 (m, 5H), 4.18 (m, 2H), 4.91 (m, 1H), 6.08 (m, 1H), 6.58 (m, 1H), 6.92 (d, 1H), 7.13 (m, 1H), 7.52 (dd, 1H), 8.14 (d, 1H); APCI m/z 408 [M + H]⁺ | 39% |
| 83 | 3,5-dimethyl-4-cyanophenyl | H | APCI m/z 391 [M + H]⁺ | 64% |
| 84 | 3-methoxy-2-methylphenyl | H | APCI m/z 382 [M + H]⁺ | 60% |
| 85 | 2,6-dichlorophenyl | H | δ: 2.12 (s, 3H), 4.01 (m, 5H), 4.20 (m, 2H), 4.78 (m, 1H), 6.90 (d, 1H), 6.96 (m, 1H), 7.25 (d, 2H), 7.53 (dd, 1H), 8.12 (d, 1H); APCI m/z 406 [M + H]⁺ | 34% |

-continued

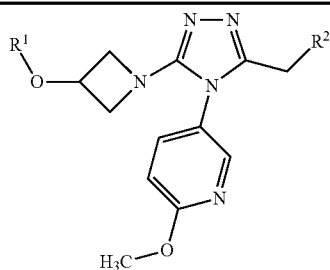

| No. | R¹ | R² | Data (LRMS and/or ¹H NMR) | Yield |
|---|---|---|---|---|
| 86 | Cl-, F (3-Cl-4-F-phenyl) | H | δ: 2.21 (s, 3H), 3.92 (m, 2H), 4.02 (s, 3H), 4.15 (m, 2H), 4.82 (m, 1H), 6.55 (m, 1H), 6.70 (m, 1H), 6.90 (d, 1H), 7.02 (m, 1H), 7.50 (dd, 1H), 8.13 (d, 1H); APCI m/z 390 [M + H]⁺ | 92% |
| 87 | H₃C-, F (3-Me-4-F-phenyl) | H | APCI m/z 370 [M + H]⁺ | 43% |
| 88 | F-, F (2,5-diF-phenyl) | H | APCI m/z 374 [M + H]⁺ | 65% |
| 89 | Cl-, F (4-Cl-2-F-phenyl) | H | APCI m/z 390 [M + H]⁺ | 43% |
| 90 | F, CH₃ (4-F-3-Me-phenyl) | H | APCI m/z 370 [M + H]⁺ | 72% |
| 91 | Cl-pyridyl | H | APCI m/z 373 [M + H]⁺ | 67% |
| 92 | F, CH₃ (2,5-F, 4-Me) | OCH₃ | δ: 2.16 (s, 3H), 3.29 (s, 3H), 3.99 (s, 3H), 3.92-4.02 (m, 2H), 4.17 (m, 2H), 4.31 (s, 2H), 4.87 (m, 1H), 6.28 (m, 1H), 6.73 (m, 1H), 6.82-6.90 (m, 2H), 7.62 (m, 1H), 8.21 (m, 1H); APCI m/z 400 [M + H]⁺ | 67% |
| 93 | F, CH₃ | OCH₃ | δ: 2.12 (s, 3H), 3.29 (s, 3H), 3.99 (s, 3H), 3.94-4.01 (m, 2H), 4.18 (m, 2H), 4.31 (s, 2H), 4.88 (m, 1H), 6.09 (m, 1H), 6.56 (m, 1H), 6.87 (m, 1H), 7.04 (m, 1H), 7.60 (m, 1H), 8.20 (d, 1H); APCI m/z 400 [M + H]⁺ | 71% |
| 94 | F, Cl | OCH₃ | δ: 3.29 (s, 3H), 4.00 (s, 3H), 4.06 (dd, 2H), 4.28 (m, 2H), 4.31 (s, 2H), 4.95 (m, 1H), 6.29 (dd, 1H), 6.65 (m, 1H), 6.87 (m, 1H), 7.30 (dd, 1H), 7.65 (dd, 1H), 8.22 (m, 1H); APCI m/z 420/422 [M + H]⁺ | 71% |

-continued

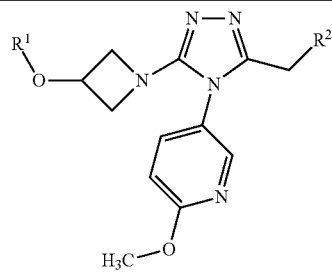

| No. | R¹ | R² | Data (LRMS and/or ¹H NMR) | Yield |
|-----|----|----|---------------------------|-------|
| 95 | 2-chloro-6-fluorophenyl | OCH₃ | δ: 3.29 (s, 3H), 4.00 (s, 3H), 4.13 (m, 4H), 4.31 (s, 2H), 4.91(m, 1H), 6.86 (d, 1H), 6.94-7.00 (m, 2H), 7.13 (s, 1H), 7.63 (dd, 1H), 8.21 (m, 1H); APCI m/z 420/422 [M + H]⁺ | 54% |
| 96 | 3-chloro-2,5-difluorophenyl | OCH₃ | δ: 3.29 (s, 3H), 4.00 (s, 3H), 4.05 (m, 2H), 4.28 (m, 2H), 4.31 (s, 2H), 4.95 (m, 1H), 6.11 (m, 1H), 6.58 (m, 1H), 6.87 (d, 1H), 7.64 (dd, 1H), 8.22 (m, 1H); APCI m/z 438/440 [M + H]⁺ | 47% |
| 97 | 2,6-dichlorophenyl | OCH₃ | δ: 3.29 (s, 3H), 4.00 (s, 3H), 4.15 (m, 2H), 4.26 (m, 2H) 4.31 (s, 2H), 4.83 (m, 1H), 6.87 (d, 1H), 6.98 (dd, 2H), 7.23-7.29 (m, 2H), 7.64 (dd, 1H), 8.22 (m, 1H); APCI m/z 436/438/440 [M + H]⁺ | 61% |
| 98 | 4-cyano-2,6-dimethylphenyl | OCH₃ | APCI m/z 421 [M + H]⁺ | 53% |
| 99 | 4-fluoro-3-methylphenyl | OCH₃ | APCI m/z 400 [M + H]⁺ | 73% |
| 100 | 3-chloro-4-fluorophenyl | OCH₃ | APCI m/z 420/422 [M + H]⁺ | 82% |
| 101 | 4-chloro-2-fluorophenyl | OCH₃ | APCI m/z 420/422 [M + H]⁺ | 70% |
| 102 | 4-fluoro-2-methylphenyl | OCH₃ | APCI m/z 400 [M + H]⁺ | 84% |

-continued

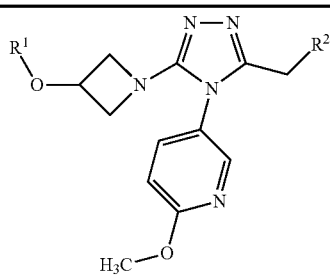

| No. | R¹ | R² | Data (LRMS and/or ¹H NMR) | Yield |
|---|---|---|---|---|
| 103 | 2,5-difluorophenyl | OCH₃ | APCI m/z 404 [M + H]⁺ | 73% |
| 104 | 3-(trifluoromethyl)-1-methyl-1H-pyrazol-5-yl | OCH₃ | ESI m/z 440 [M + H]⁺ | 6% |
| 105 | 5-(trifluoromethyl)-1-methyl-1H-pyrazol-3-yl | OCH₃ | ESI m/z 440 [M + H]⁺ | 28% |
| 106 | 1,5-dimethyl-1H-pyrazol-3-yl | OCH₃ | ESI m/z 386 [M + H]⁺ | 28% |
| 107 | 2-methylpyridin-3-yl | OCH₃ | APCI m/z 383 [M + H]⁺ | 75% |
| 108 | 4-chloro-5-methylpyrimidin-6-yl | OCH₃ | APCI m/z 418 [M + H]⁺ | 99% |

NMR spectra were run at 400 MHz in CDCl₃

Example 84: 3-methoxy-2-methyl-phenol can be prepared as described in *J. Med. Chem.* 1990, 33, 614

Examples 95-98: Crude compounds were triturated with diethyl ether

Example 106: 1,5-dimethyl-1H-pyrazol-3-ol can be prepared as described in Tetrahedron, 1998, 54, 9393

EXAMPLE 109: 4-({1-[4-(6-METHOXY-2-METHYLPYRIDIN-3-YL)-5-METHYL-4H-1,2,4-TRIAZOL-3-YL]AZETIDIN-3-YL}OXY)-3-METHYLBENZONITRILE

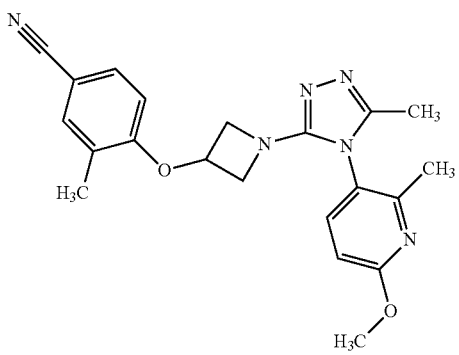 [SMILES: COc1ccc(-n2c(C)nnc2N2CC(Oc3ccc(C#N)cc3C)C2)c(C)n1]

The title compound was prepared from the products of preparations 16 and 70, using the same method as that described for example 1, as a pale brown solid in 51% yield. $^1$H NMR (400 MHz, CDCl$_3$) δ: 2.12 (s, 3H), 2.18 (s, 3H), 2.23 (s, 3H), 3.88 (s, 1H), 3.95 (s, 4H), 4.06 (s, 1H), 4.15 (s, 1H), 4.93 (s, 1H), 6.41 (d, 1H), 6.69 (d, 1H), 7.37 (d, 1H), 7.40 (m, 2H)

EXAMPLE 110: 2-METHOXY-5-[3-METHYL-5-(3-PHENOXYAZETIDIN-1-YL)-4H-1,2,4-TRIAZOL-4-YL]PYRIDINE

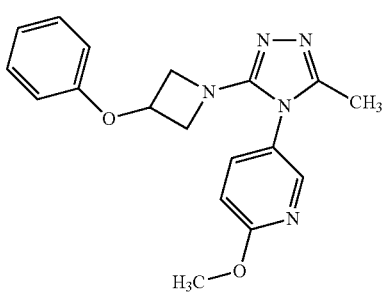 [SMILES: COc1ccc(-n2c(C)nnc2N2CC(Oc3ccccc3)C2)cn1]

The title compound was prepared from the product of preparation 65 and acetylhydrazide, using the same method as that described for preparation 4, in 89% yield. LRMS ESI m/z 358 [M+H]$^+$

EXAMPLE 111: [5-[3-(2-CHLORO-4-FLUOROPHENOXY)AZETIDIN-1-YL]-4-(6-METHOXYPYRIDIN-3-YL)-4H-1,2,4-TRIAZOL-3-YL]METHANOL

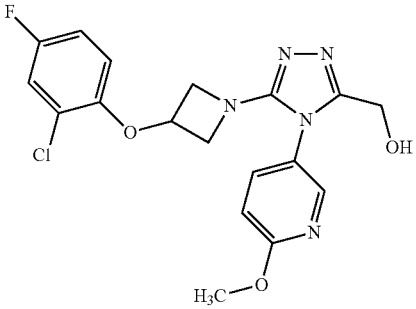 [SMILES: COc1ccc(-n2c(CO)nnc2N2CC(Oc3ccc(F)cc3Cl)C2)cn1]

A mixture of the products of preparations 81 (300 mg, 0.8 mmol) and 80 (360 mg, 4 mmol) in butanol (5 mL) was heated under reflux for 18 hours. The reaction mixture was then cooled to room temperature concentrated in vacuo and the residue was purified by HPLC using a Phenomenex Luna C18 system, eluting with water/acetonitrile/trifluoroacetic acid (5:95:0.1):acetonitrile, 95:5 to 5:95, to afford the title compound as a clear oil in 6% yield. LRMS ESI m/z 406 [M+H]$^+$

EXAMPLE 112: 5-[3-[3-(2-CHLORO-4-FLUOROPHENOXY)AZETIDIN-1-YL]-5-(METHOXYMETHYL)-4H-1,2,4-TRIAZOL-4-YL]-2-METHOXYPYRIDINE

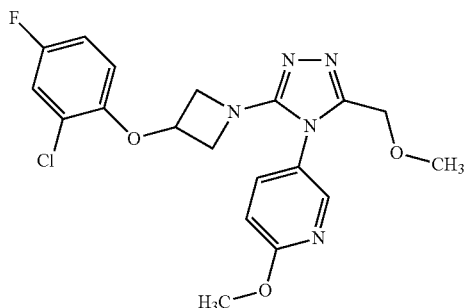

Potassium tert-butoxide (4 g, 35.42 mmol) was added portionwise to an ice-cooled solution of the product of preparation 80 (10.86 g, 29.52 mmol) in tetrahydrofuran (100 mL) and the reaction was stirred at room temperature for 20 minutes. Methyl p-toluenesulfonate (51.4 mg, 0.28 mmol) was then added and the mixture was stirred for 40 minutes. The reaction mixture was then concentrated in vacuo and partitioned between ethyl acetate (150 mL) and water (50 mL). The organic layer was separated washed with water and brine, dried over magnesium sulfate and concentrated in vacuo. The residue was re-dissolved in tetrahydrofuran (75 mL) and trifluoroacetic acid (1.2 mL), 2-methoxyacetylhydrazide (preparation 5, 6.15 g, 59.04 mmol) was added and the mixture was heated under reflux for 90 minutes. The reaction mixture was then concentrated in vacuo and re-dissolved in ethyl acetate. The organic solution was washed with sodium hydrogen carbonate solution and brine, dried over magnesium sulfate and concentrated in vacuo to give an oil. The oil was then triturated with diethyl ether to afford the title compound as a solid in 52% yield, 6.5 g. $^1$H NMR (400 MHz, CDCl$_3$) δ: 3.29 (s, 3H), 3.99 (s, 3H), 4.05 (dd, 2H), 4.18 (m, 2H), 4.31 (s, 2H), 4.92 (m, 1H), 6.50 (m, 1H), 6.85 (m, 2H), 7.15 (dd, 1H), 7.61 (dd, 1H), 8.22 (d, 1H); LRMS APCI m/z 420/422 [M+H]$^+$

EXAMPLES 113 TO 124

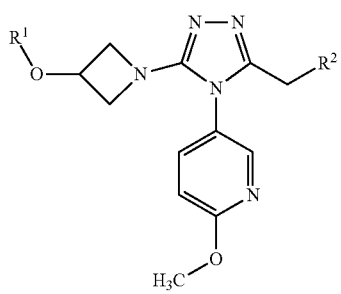

A mixture of the appropriate phenol [commercial, unless stated below, (1 eq)], caesium carbonate (4 eq) and either the product of preparation 4 (1 eq) or preparation 6 (1 eq) in acetonitrile (2 mL) was heated under an atmosphere of nitrogen, at reflux for 24 hours. The crude mixture then was partitioned between dichloromethane and water and passed through a phase separation tube. The organic solution was concentrated in vacuo and the residue was purified by HPLC using a Phenomenex Luna C18 column, eluting with water/ 0.1% formic acid:acetonitrile/0.1% formic acid, 95:5 to 5:95, to afford the title compound.

| No. | R¹ | R² | Data (LRMS and/or ¹H NMR) | Yield |
|---|---|---|---|---|
| 113 | (2-fluoro-3-methylphenyl) | OCH$_3$ | δ: 2.10 (s, 3H), 3.29 (s, 3H), 4.00 (m, 5H), 4.20 (m, 2H), 4.34 (s, 2H), 4.93 (m, 1H), 6.18 (d, 1H), 6.67 (m, 1H), 6.88 (d, 1H), 7.02 (m, 1H), 7.61 (dd, 1H), 8.23 (d, 1H); APCI m/z 400 [M + H]⁺ | 48% |
| 114 | (3,5-difluoro-4-methylphenyl) | OCH$_3$ | δ: 3.30 (s, 3H), 4.00 (m, 5H), 4.23 (m, 2H), 4.35 (s, 2H), 4.90 (m, 1H), 5.95 (d, 1H), 6.43 (m, 1H), 6.88 (d, 1H), 7.62 (dd, 1H), 8.23 (d, 1H); APCI m/z 418 [M + H]⁺ | 53% |
| 115 | (2,3-difluorophenyl) | OCH$_3$ | APCI m/z 404 [M + H]⁺ | 70% |
| 116 | (2-chloro-3-cyanophenyl) | OCH$_3$ | δ: 3.32 (s, 3H), 4.03 (m, 5H), 4.26 (m, 2H), 4.36 (s, 2H), 5.00 (m, 1H), 6.78 (d, 1H), 6.89 (d, 1H), 7.30 (m, 2H), 7.62 (dd, 1H), 8.12 (d, 1H); APCI m/z 427 [M +H]⁺ | 41% |
| 117 | (3-chloro-4-cyanophenyl) | OCH$_3$ | APCI m/z 427 [M + H]⁺ | 41% |
| 118 | (2,6-difluoro-3-trifluoromethylphenyl) | OCH$_3$ | δ: 3.28 (s, 3H), 4.02 (m, 5H), 4.30 (m, 4H), 5.00 (m, 1H), 6.37 (d, 1H), 6.80 (m, 1H), 6.88 (d, 1H), 7.37 (m, 1H), 7.65 (dd, 1H), 8.23 (d, 1H); APCI m/z 454 [M + H]⁺ | 50% |
| 119 | (2-fluoro-3-methylphenyl) | H | δ: 2.10 (s, 3H), 2.22 (s, 3H), 3.98 (m, 2H), 4.02 (s, 3H), 4.18 (m, 2H), 4.91 (m, 1H), 6.17 (d, 1H), 6.66 (m, 1H), 6.91 (d, 1H), 7.02 (m, 1H), 7.55 (dd, 1H), 8.14 (d, 1H); APCI m/z 370 [M + H]⁺ | 48% |

-continued

| No. | R¹ | R² | Data (LRMS and/or ¹H NMR) | Yield |
|---|---|---|---|---|
| 120 | 3,5-difluoro-2-methylphenyl | H | δ: 2.04 (s, 3H), 2.22 (s, 3H), 3.97 (m, 2H), 4.03 (s, 3H), 4.22 (m, 2H), 4.90 (m, 1H), 5.97 (d, 1H), 6.43 (s, 1H), 6.90 (d, 1H), 7.58 (dd, 1H), 8.16 (d, 1H); APCI m/z 388 [M + H]⁺ | 39% |
| 121 | 2-chloro-3-cyanophenyl | H | APCI m/z 397 [M + H]⁺ | 11% |
| 122 | 4-cyano-2-chlorophenyl | H | APCI m/z 397 [M + H]⁺ | 19% |
| 123 | 2-fluoro-6-(trifluoromethyl)phenyl | H | APCI m/z 424 [M + H]⁺ | 22% |
| 124 | 5-fluoro-2-(trifluoromethyl)phenyl | H | APCI m/z 424 [M + H]⁺ | 0.1% |

NMR spectra were run at 400 MHz in CDCl₃

Example 120: 3,5-Difluoro-2-methylphenol was prepared as described in preparation 68

Example 121: 2-chloro-3-hydroxybenzonitrile was prepared as described in preparation 72

Example 122: 3-chloro-4-hydroxybenzonitrile was prepared as described in preparation 71

Example 123: 3-fluoro-2-(trifluoromethyl)phenol was prepared as described in preparation 73

EXAMPLE 125: 1-[4-(6-METHOXYPYRIDIN-3-YL)-5-METHYL-4H-1,2,4-TRIAZOL-3-YL]AZETIDIN-3-OL

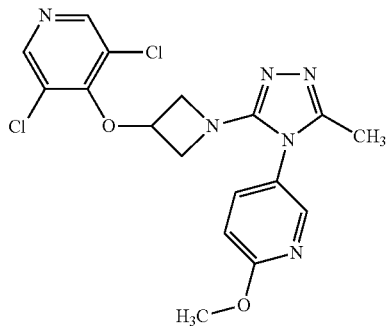 [SMILES: COc1ccc(-n2c(C)nnc2N2CC(Oc3c(Cl)cncc3Cl)C2)cn1]

A mixture of the product of preparation 82 (135 mg, 0.52 mmol) and 3,4,5-trichloropyridine (94 mg, 0.52 mmol) in dimethylsulfoxide (5 mL) was stirred at room temperature for 24 hours. The reaction mixture was then partitioned between dichloromethane and water and the organic layer was separated, washed with brine, dried over magnesium sulfate and concentrated in vacuo. Purification of the residue by column chromatography on silica gel, eluting with dichloromethane:methanol, 100:0 to 95:5, afforded the title compound as a crystalline solid in 43% yield, 90 mg.

$^1$H NMR (400 MHz, CDCl$_3$) δ: 2.21 (s, 3H), 4.00 (s, 3H), 4.07 (m, 2H), 4.14 (m, 2H), 4.96 (m, 1H), 6.88 (d, 1H), 7.50 (dd, 1H), 8.10 (d, 1H); LRMS ESI m/z 409 [M+H]$^+$

EXAMPLES 126 TO 128

The following compounds, of the general formula shown below, were prepared using the same method to that described for example 125, using the product of preparation 82 with commercially available phenols or compounds known in the literature, as outlined below.

| No. | R$^1$ | R$^2$ | Data (LRMS) | Yield |
|---|---|---|---|---|
| 126 | 3-chloropyridin-2-yl | H | APCI m/z 373 [M + H]$^+$ | 50% |
| 127 | 3-(trifluoromethyl)pyridin-2-yl | H | APCI m/z 407 [M + H]$^+$ | 12% |
| 128 | 4-chloro-5-methylpyrimidin-... | H | APCI m/z 388 [M + H]$^+$ | 44% |

Example 127: crude compound was twice triturated with diethyl ether

EXAMPLES 129 TO 138

The following compounds, of the general formula shown below, were prepared from the products of preparation 21 (examples 129-133) and preparation 42 (examples 134-138) and 1 to 2 equivalents of the appropriate commercial phenol (or phenol known in the literature as outlined below), using the same method to that described example 37.

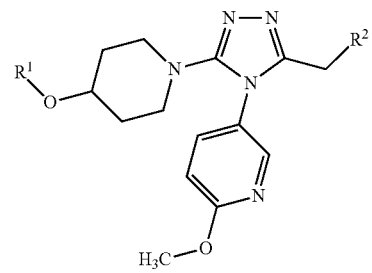

| No. | R$^1$ | R$^2$ | Data (LRMS and/or $^1$H NMR) | Yield |
|---|---|---|---|---|
| 129 | 3-cyano-2-methylphenyl | H | δ: 1.75 (m, 2H) 1.95 (m, 2H), 2.25 (s, 3H) 2.40 (s, 3H), 3.30 (m, 2H), 3.50 (m, 2H), 4.00 (s, 3H), 4.45 (m, 1H), 6.90 (d, 1H), 6.98 (m, 1H), 7.18 (d, 2H), 7.55 (d, 1H), 8.15 (s, 1H); APCI m/z 405 [M + H]$^+$ | 19% |

-continued

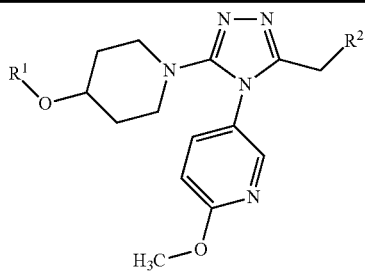

| No. | R¹ | R² | Data (LRMS and/or ¹H NMR) | Yield |
|---|---|---|---|---|
| 130 | (3-pyridyl with 4-CH₃) | H | APCI m/z 381 [M + H]⁺ | 16% |
| 131 | (phenyl with 2-CH₃, 3-CONH₂) | H | APCI m/z 423 [M + H]⁺ | 16% |
| 132 | (phenyl with 2-CH₃, 3-C(O)N(CH₃)₂) | H | δ: 1.60-2.00 (m, 4H), 2.10 (s, 3H), 2.25 (s, 3H), 2.80 (s, 3H), 3.00 (m, 2H), 3.10 (s, 3H), 3.2-3.40 (m, 2H), 4.00 (s, 3H), 4.40 (m, 1H), 6.80 (m, 2H), 6.90 (d, 1H), 7.15 (m, 1H), 7.58 (d, 1H), 8.17 (s, 1H); APCI m/z 451 [M + H]⁺ | 8% |
| 133 | (phenyl with 2-CH₂OCH₃) | H | APCI m/z 410 [M + H]⁺ | 4% |
| 134 | (phenyl with 2-CH₃, 3-CN) | OCH₃ | δ: 1.80-2.00 (m, 4H), 2.40 (s, 3H), 3.00-3.40 (m, 7H), 4.00 (s, 3H), 4.30 (m, 2H), 4.50 (m, 1H), 6.90 (d, 1H), 7.00 (m, 1H), 7.20 (m, 2H), 7.70 (d, 1H), 8.25 (s, 1H); APCI m/z 435 [M + H]⁺ | 33% |
| 135 | (phenyl with 2-CH₃, 3-C(O)N(CH₃)₂) | OCH₃ | APCI m/z 481 [M + H]⁺ | 17% |
| 136 | (pyrimidine with 4-CH₃, 2-N(CH₃)₂) | OCH₃ | APCI m/z 455 [M + H]⁺ | 12% |
| 137 | (2,3-difluorophenyl) | OCH₃ | δ: 1.80 (m, 2H), 1.90 (m, 2H), 3.00 (m, 2H), 3.38 (s, 3H), 3.40 (m, 2H), 4.00 (s, 3H), 4.30 (s, 2H), 4.40 (m, 1H), 6.70-6.80 (m, 2H), 6.85 (d, 1H), 6.90 (m, 1H), 7.55 (dd, 1H), 8.25 (d, 1H); APCI m/z 432 [M + H]⁺ | 39% |

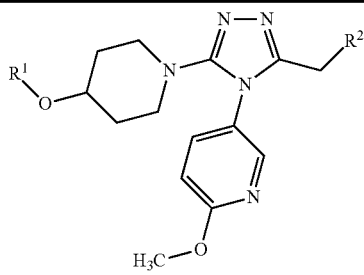

| No. | R[1] | R[2] | Data (LRMS and/or $^1$H NMR) | Yield |
|---|---|---|---|---|
| 138 | (3-pyridyl-4-methyl) | OCH$_3$ | δ: 1.80 (m, 2H), 1.90 (m, 2H), 2.20 (s, 3H), 3.10 (m, 2H), 3.30-3.40 (m, 5H), 4.00 (s, 3H), 4.25 (s, 2H), 4.40 (m, 1H), 6.80 (d, 1H), 7.05 (d, 1H), 7.60 (dd, 1H), 8.08 (d, 1H), 8.25 (d, 1H); APCI m/z 411 [M + H]$^+$ | 52% |

NMR spectra were run at 400 MHz in CDCl$_3$

Example 129: 3-Hydroxy-2-methylbenzonitrile was prepared as described in preparation 74

Example 131: 3-Hydroxy-2-methylbenzamide was prepared as described in preparation 75

Example 132 and 135: 3-Hydroxy-N,N,2-trimethylbenzamide was prepared as described in preparation 76

Example 133: 2-(Methoxymethyl)phenol was prepared as described in preparation 77.

Example 136: 2-(Dimethylamino)-4-methyl-5-pyrimidinol may be prepared as described in EP 138464, p22.

EXAMPLE 139: 5-{3-[(3S)-3-(2-CHLOROPHENOXY)PYRROLIDIN-1-YL]-5-METHYL-4H-1,2,4-TRIAZOL-4-YL}-2-METHOXYPYRIDINE

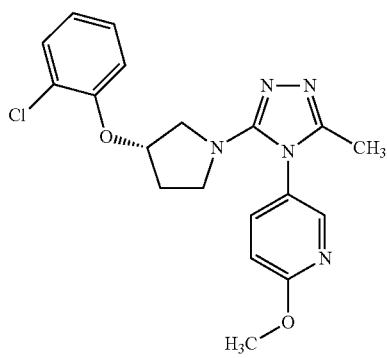 [SMILES: COc1ccc(-n2c(C)nnc2N2CC[C@H](Oc3ccccc3Cl)C2)cn1]

A mixture of the product of preparation 110 (200 mg, 0.73 mmol), 2-chlorophenol (112 mg, 0.87 mmol), di-tert-butyl azodicarboxylate (235 mg, 1.02 mmol) and polymer supported triphenylphosphine (610 mg, 1.83 mmol) in dichloromethane (10 mL) was stirred at room temperature for 18 hours. The reaction mixture was then filtered, concentrated in vacuo and the residue was purified by column chromatography on silica gel, eluting with dichloromethane:methanol, 100:0 to 92:8, to afford the title compound as a glass in 74% yield, 209 mg. $^1$H NMR (400 MHz, CDCl$_3$) δ: 2.10 (m, 5H) 3.20 (m, 1H), 3.40 (m, 1H), 3.50 (m, 2H), 4.00 (s, 3H), 4.80 (m, 1H), 6.80 (m, 3H), 7.15 (m, 1H), 7.30 (d, 1H), 7.50 (d, 1H), 8.10 (s, 1H); LRMS APCI m/z 386 [M+H]$^+$ EXAMPLE 140: 2-METHOXY-5-{3-METHYL-5-[(3S)-3-(2-METHYLPHENOXY)PYRROLIDIN-1-YL]-4H-1,2,4-TRIAZOL-4-YL}PYRIDINE

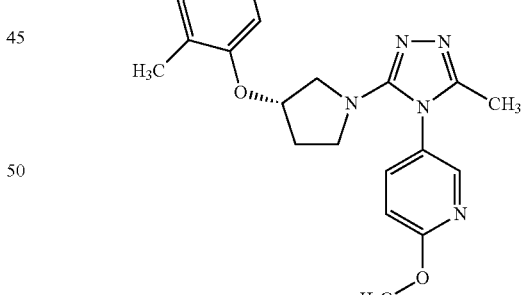

The title compound was prepared from the product of preparation 110 and 2-methylphenol, using the same method as that described for example 139. The crude compound was purified by HPLC using a Phenomenex Luna C18 system, eluting with water/acetonitrile/trifluoroacetic acid (5:95:0.1):acetonitrile, 95:5 to 5:95, to afford the desired product in 31% yield. LRMS APCI m/z 367 [M+H]$^+$

EXAMPLE 141: 3-({1-[4-(6-METHOXYPYRIDIN-3-YL)-5-METHYL-4H-1,2,4-TRIAZOL-3-YL]PIPERIDIN-4-YL}OXY)PHTHALONITRILE

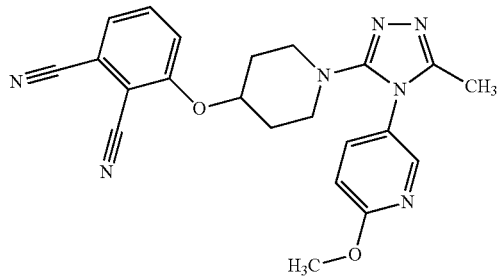 [SMILES: COc1ccc(-n2c(C)nnc2N2CCC(Oc3cccc(C#N)c3C#N)CC2)cn1]

Potassium tert-butoxide (42 mg, 0.57 mmol) was added to a solution of the product of preparation 21 (150 mg, 0.52 mmol) in tetrahydrofuran (5 mL) and the mixture was stirred at room temperature for 30 minutes. 3-Fluorophthalonitrile (76 mg, 0.52 mmol) was added and the mixture was stirred at room temperature for 18 hours. The reaction mixture was then partitioned between ethyl acetate and water and the organic layer was separated, dried over magnesium sulfate and concentrated in vacuo. Purification of the residue by column chromatography on silica gel, eluting with dichloromethane:methanol, 100:0 to 95:5, to afford the title compound as a solid in 37% yield, 79 mg. $^1$H NMR (400 MHz, CDCl$_3$) δ: 1.80 (m, 2H) 2.10 (m, 2H), 2.25 (s, 3H), 3.10 (m, 2H), 3.40 (m, 2H), 4.00 (s, 3H), 4.60 (m, 1H), 6.95 (d, 1H), 7.20 (m, 1H), 7.35 (d, 1H), 7.60 (m, 2H), 8.15 (s, 1H); LRMS APCI m/z 416 [M+H]$^+$

EXAMPLE 142: 3-({1-[5-(METHOXYMETHYL)-4-(6-METHOXYPYRIDIN-3-YL)-4H-1,2,4-TRIAZOL-3-YL]PIPERIDIN-4-YL}OXY)PHTHALONITRILE

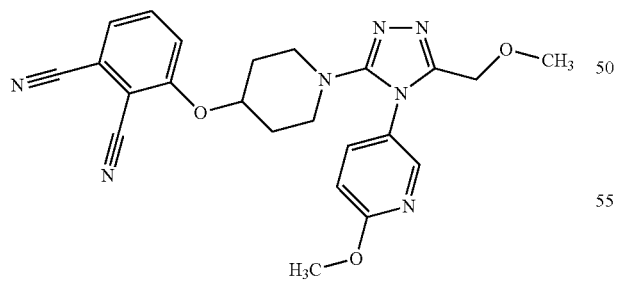

The title compound was prepared from the product of preparation 42 and 3-fluorophthalonitrile, using the same method as that described for example 141 as an oil in 31% yield. LRMS APCI m/z 446 [M+H]$^+$

EXAMPLE 143: 6-({1-[4-(6-METHOXYPYRIDIN-3-YL)-5-METHYL-4H-1,2,4-TRIAZOL-3-YL]PIPERIDIN-4-YL}OXY)-1-METHYLPYRIDIN-2(1H)-ONE

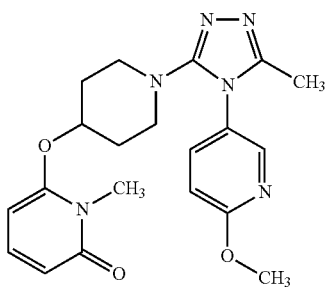 [SMILES: COc1ccc(-n2c(C)nnc2N2CCC(Oc3cccc(=O)n3C)CC2)cn1]

The title compound was prepared by sequential treatment of the product of preparation 116 with potassium tert-butoxide and acetylhydrazide, using the same method as that described for example 55, as a solid in 76% yield. LRMS APCI m/z 397 [M+H]$^+$

EXAMPLE 144: 6-({1-[5-(METHOXYMETHYL)-4-(6-METHOXYPYRIDIN-3-YL)-4H-1,2,4-TRIAZOL-3-YL]PIPERIDIN-4-YL}OXY)-1-METHYLPYRIDIN-2(1H)-ONE

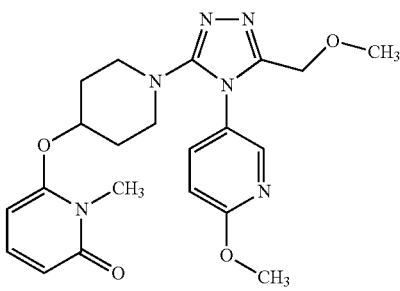 [SMILES: COCc1nnc(N2CCC(Oc3cccc(=O)n3C)CC2)n1-c1ccc(OC)nc1]

The title compound was prepared by sequential treatment of the product of preparation 116 with potassium tert-butoxide and 2-methoxyacetylhydrazide (preparation 5), using the same method as that described for example 55, as a solid in 62% yield. LRMS APCI m/z 427 [M+H]$^+$

EXAMPLES 145 TO 157

The following compounds, of the general formula shown below, were prepared using the same method to that described preparation 4. The products of preparations 103-109 were treated with acetylhydrazide to afford examples 145 to 150 and with 2-methoxyacetylhydrazide (preparation 5) to afford examples 151 to 157.

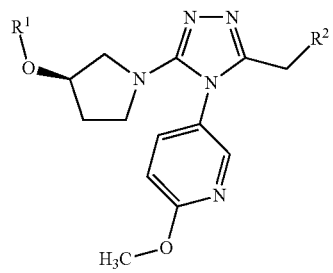

| No. | R¹ | R² | Data (LRMS and/or ¹H NMR) | Yield |
|---|---|---|---|---|
| 145 | 3-methoxy-4-cyanophenyl (N≡C—, OCH₃) | H | APCI m/z 407 [M + H]⁺ | 24% |
| 146 | 2-chlorophenyl | H | δ: 2.10-2.20 (m, 5H), 3.25 (m, 1H), 3.40 (m, 1H), 3.45-3.50 (m, 2H), 4.00 (s, 3H), 4.90 (m, 1H), 6.80-6.90 (m, 3H), 7.15 (m, 1H), 7.35 (dd, 1H), 7.50 (dd, 1H), 8.10 (d, 1H); APCI m/z 386 [M + H]⁺ | 52% |
| 147 | 2-methoxyphenyl | H | APCI m/z 383 [M + H]⁺ | 22% |
| 148 | 2-methylphenyl | H | δ: 2.10 (m, 5H), 2.15 (s, 3H), 3.25 (m, 1H), 3.40 (m, 2H), 3.48 (m, 1H), 4.00 (s, 3H), 4.80 (m, 1H), 6.68 (d, 1H), 6.80 (m, 1H), 7.10 (m, 2H), 7.48 (dd, 1H), 8.10 (d, 1H); APCI m/z 366 [M + H]⁺ | 58% |
| 149 | 2-cyanophenyl | H | APCI m/z 377 [M + H]⁺ | 34% |
| 150 | 4-fluorophenyl | H | APCI m/z 370 [M + H]⁺ | 77% |
| 151 | 3-methoxy-4-cyanophenyl | OCH₃ | APCI m/z 437 [M + H]⁺ | 41% |
| 152 | 2-chlorophenyl | OCH₃ | δ: 2.05-2.15 (m, 2H), 3.25 (s, 3H), 3.38 (m, 1H), 3.45 (m, 1H), 3.58 (d, 1H), 3.65 (dd, 1H), 4.00 (s, 3H), 4.10-4.30 (m, 2H), 4.95 (m, 1H), 6.85 (m, 2H), 6.95 (m, 1H), 7.20 (m, 1H), 7.35 (dd, 1H), 7.65 (dd, 1H), 8.25 (d, 1H); APCI m/z 416 [M + H]⁺ | 52% |

-continued

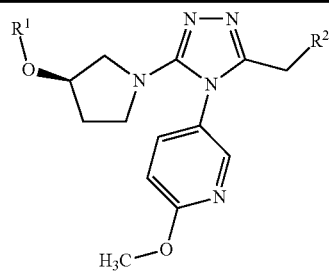

| No. | R¹ | R² | Data (LRMS and/or ¹H NMR) | Yield |
|---|---|---|---|---|
| 153 | 2-methoxyphenyl-CH₂- | OCH₃ | δ: 2.00-2.20 (m, 2H) 2.25 (s, 3H), 3.50 (m, 4H), 3.80 (s, 3H), 4.00 (s, 3H), 4.30 (m, 2H), 4.90 (m, 1H), 6.80 (m, 4H), 6.95 (m, 1H), 7.60 (d, 1H), 8.20 (s, 1H); APCI m/z 412 [M + H]⁺ | 31% |
| 154 | 2-methylphenyl-CH₂- | OCH₃ | δ: 2.05-2.10 (m, 5H), 3.20-3.25 (m, 4H), 3.35-3.45 (m, 2H), 3.50 (m, 1H), 4.00 (s, 3H), 4.25 (s, 2H), 4.88 (m, 1H), 6.71-6.81 (m, 2H), 6.87 (m, 1H), 6.89 (m, 1H), 6.91-6.97 (m, 1H), 7.65 (dd, 1H), 8.26 (d, 1H); APCI m/z 396 [M + H]⁺ | 61% |
| 155 | 2-cyanophenyl-CH₂- | OCH₃ | APCI m/z 407 [M + H]⁺ | 31% |
| 156 | 4-cyanophenyl-CH₂- | OCH₃ | APCI m/z 407 [M + H]⁺ | 59% |
| 157 | 4-fluorophenyl-CH₂- | OCH₃ | APCI m/z 400 [M + H]⁺ | 62% |

NMR spectra were run at 400 MHz in CDCl₃

EXAMPLES 158 TO 159

The following compounds, of the general formula shown below, were prepared using the same method to that described example 55. The product of preparation 101 was treated sequentially with potassium tert-butoxide and either acetylhydrazide to afford example 158 or 2-methoxyacetyl-hydrazide (preparation 5) to afford example 159. The crude compounds were triturated with diethyl ether to afford desired product.

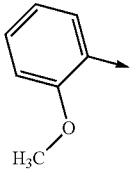

| No. | R¹ | R² | Data (LRMS) | Yield |
|---|---|---|---|---|
| 158 | 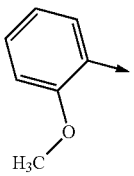 | H | APCI m/z 382 [M + H]⁺ | 29% |
| 159 | 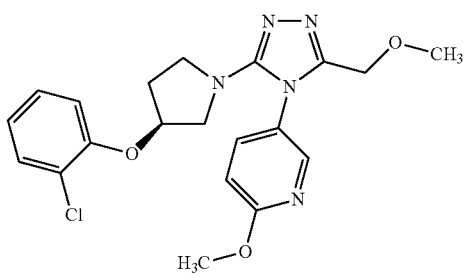 | OCH₃ | APCI m/z 412 [M + H]⁺ | 31% |

EXAMPLE 160: 5-[3-[(3S)-3-(2-CHLOROPHE-NOXY)PYRROLIDIN-1-YL]-5-(METHOXYM-ETHYL)-4H-1,2,4-TRIAZOL-4-YL]-2-METHOXY-PYRIDINE

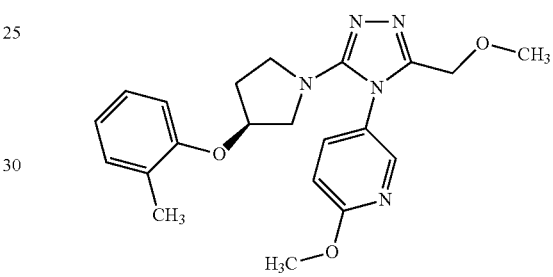

5-Isothiocyanato-2-methoxypyridine [(306 mg, 1.84 mmol), *J. Org. Chem.* (1980), 45, 4219] was added to a solution of the product of preparation 91 [(387 mg, 1.95 mmol) and N,N-diisopropylethylamine (0.32 mL, 1.84 mmol) in dichloromethane (5 mL) and the mixture was stirred for 1 hour at room temperature. The reaction mixture was then washed with water (5 mL), saturated citric acid solution (5 mL) and brine. The organic solution was dried over magnesium sulfate and concentrated in vacuo. Potassium tert-butoxide (217 mg, 1.93 mmol) was added to a solution of the residue in tetrahydrofuran (6 mL) and the reaction was stirred at room temperature for 15 minutes. Methyl p-toluenesulfonate (360 mg, 1.93 mmol) was then added and the mixture was stirred for 45 minutes at room temperature. The reaction mixture was concentrated in vacuo and re-dissolved in dichloromethane. The organic solution was washed with sodium hydrogen carbonate solution, dried over magnesium sulfate and concentrated in vacuo. The residue was re-dissolved in tetrahydrofuran (10 mL), trifluoroacetic acid (67 µL) and 2-methoxyacetylhy-drazide (183 mg, 1.76 mmol) were added and the mixture was heated under reflux for 2 hours. The reaction mixture was then concentrated in vacuo and partitioned between ethyl acetate and water. The organic solution was separated, washed with sodium hydrogen carbonate solution and brine, dried over magnesium sulfate and concentrated in vacuo. Purification of the residue by column chromatography on silica gel, eluting with dichloromethane:methanol, 100:0 to 95:5, afforded the title compound in 25% yield, 191 mg.

¹H NMR (400 MHz, CDCl₃) δ: 2.00-2.10 (m, 2H), 3.20-3.60 (m, 7H), 3.98 (s, 3H), 4.25 (s, 2H), 4.85-4.90 (m, 1H), 6.78-6.90 (m, 3H), 7.10-7.18 (m, 1H), 7.30-7.35 (d, 1H), 7.55-7.60 (d, 1H), 8.20 (s, 1H); APCI m/z 416 [M+H]⁺

EXAMPLE 161: 2-METHOXY-5-{3-(METHOXYMETHYL)-5-[(3S)-3-(2-METHYL-PHENOXY)PYRROLIDIN-1-YL]-4H-1,2,4-TRI-AZOL-4-YL}PYRIDINE

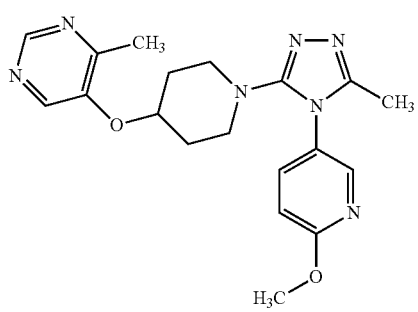 [SMILES: COc1ccc(-n2c(C)nnc2N2CCC(Oc3cncnc3C)CC2)cn1]

The title compound was prepared from the product of preparation 92, 5-Isothiocyanato-2-methoxypyridine (*J. Org. Chem.* (1980), 45, 4219) and 2-methoxyacetylhydraz-ide (preparation 5), using the same method as that described for example 160, as a foam in 52% yield. LRMS APCI m/z 396 [M+H]⁺

EXAMPLE 162: 5-({1-[4-(6-METHOXYPYRI-DIN-3-YL)-5-METHYL-4H-1,2,4-TRIAZOL-3-YL] PIPERIDIN-4-YL}OXY)-4-METHYLPYRIMI-DINE

The title compound was prepared from the product of preparation 21 and 4-methylpyrimidin-5-ol [*Chem. Hetero-cycl. Compd.* (Engl. Transl), 1989, 25, 530], using the same method as that described for example 37, in 41% yield. LRMS APCI m/z 382 [M+H]⁺

EXAMPLE 163: 5-({1-[5-(METHOXYMETHYL)-4-(6-METHOXYPYRIDIN-3-YL)-4H-1,2,4-TRIAZOL-3-YL]PIPERIDIN-4-YL}OXY)-4-METHYLPYRIMIDINE

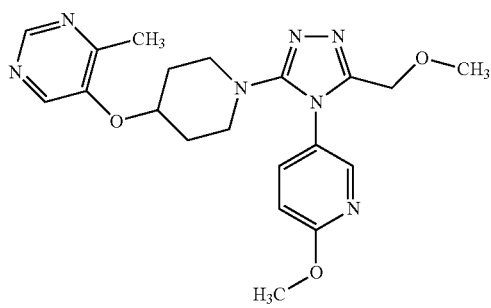 [SMILES: COCc1nnc(N2CCC(Oc3cncnc3C)CC2)n1-c1ccc(OC)nc1]

The title compound was prepared from the product of preparation 42 and 4-methylpyrimidin-5-ol [*Chem. Heterocycl. Compd.* (Engl. Transl), 1989, 25, 530], using the same method as that described for example 37, in 24% yield. $^1$H NMR (400 MHz, CDCl$_3$) δ: 1.78-1.90 (m, 2H), 1.95-2.10 (m, 2H), 2.45 (s, 3H), 3.12-3.25 (m, 2H), 3.32 (s, 3H), 3.38-3.50 (m, 2H), 4.00 (s, 3H), 4.35 (s, 2H), 4.50-4.62 (m, 1H), 6.88-6.92 (d, 1H), 7.70-7.76 (d, 1H), 8.18 (s, 1H), 8.25-8.30 (s, 1H), 8.70 (s, 1H); LRMS APCI m/z 412 [M+H]$^+$

EXAMPLE 164: 5-{3-[4-(3,5-DIFLUORO-2-METHYLPHENOXY)PIPERIDIN-1-YL]-5-METHYL-4H-1,2,4-TRIAZOL-4-YL}-2-METHOXYPYRIDINE

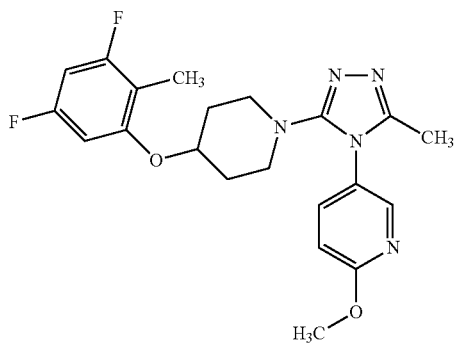 [SMILES: COc1ccc(-n2c(C)nnc2N2CCC(Oc3cc(F)cc(F)c3C)CC2)cn1]

The title compound was prepared from the product of preparation 21 and 68, using the same method as that described for example 37, in 48% yield. $^1$H NMR (400 MHz, CDCl$_3$) δ: 1.70-1.85 (m, 2H), 1.90-2.00 (m, 2H), 2.05 (s, 3H), 2.25 (s, 3H), 3.00-3.08 (m, 2H), 3.28-3.38 (m, 2H), 4.00 (s, 3H), 4.35-4.40 (m, 1H), 6.30-6.42 (m, 2H), 6.88-6.92 (d, 1H), 7.50-7.55 (d, 1H), 8.12 (s, 1H); LRMS APCI m/z 416 [M+H]$^+$

EXAMPLE 165: 5-[3-[4-(3,5-DIFLUORO-2-METHYLPHENOXY)PIPERIDIN-1-YL]-5-(METHOXYMETHYL)-4H-1,2,4-TRIAZOL-4-YL]-2-METHOXYPYRIDINE

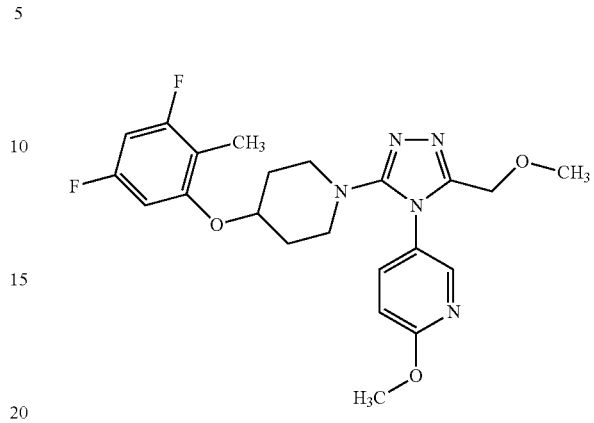

The title compound was prepared from the product of preparation 42 and 68, using the same method as that described for example 37, in 32% yield. $^1$H NMR (400 MHz, CDCl$_3$) δ: 1.72-1.85 (m, 2H), 1.90-2.00 (m, 2H), 2.05 (s, 3H), 3.05-3.12 (m, 2H), 3.30-3.40 (m, 5H), 4.00 (s, 3H), 4.35 (s, 2H), 4.38-4.42 (m, 1H), 6.30-6.42 (m, 2H), 6.87 (d, 1H), 7.67 (d, 1H), 8.25 (s, 1H); LRMS APCI m/z 446 [M+H]$^+$

EXAMPLES 166 TO 171

The following compounds, of the general formula shown below, were prepared using the same method to that described for example 139, using the product of preparation 117 with commercially available phenols.

| No. | R$^1$ | Data (LRMS) | Yield |
|---|---|---|---|
| 166 | phenyl | APCI m/z 382 [M + H]$^+$ | 30% |
| 167 | 2-fluoro-3-methylphenyl | APCI m/z 414 [M + H]$^+$ | 37% |
| 168 | 3,5-difluorophenyl | APCI m/z 418 [M + H]$^+$ | 38% |

131

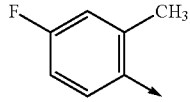

| No. | R¹ | Data (LRMS) | Yield |
|---|---|---|---|
| 169 | 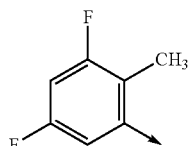 | APCI m/z 414 [M + H]⁺ | 38% |
| 170 | 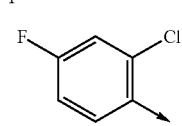 | APCI m/z 432 [M + H]⁺ | 41% |
| 171 | 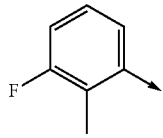 | APCI m/z 434 [M + H]⁺ | 41% |

EXAMPLE 172: 4-CHLORO-6-{1-[5-METHOXYMETHYL-4-(6-METHOXY-PYRIDIN-3-YL)-4H-[1,2,4]TRIAZOL-3-YL]-AZETIDIN-3-YLOXY}-5-METHYL-PYRIMIDINE

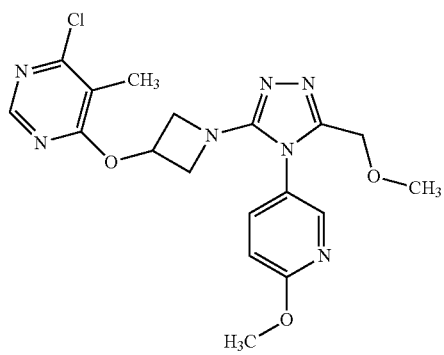 [SMILES: COCc1nnc(N2CC(Oc3ncnc(Cl)c3C)C2)n1-c1ccc(OC)nc1]

The title compound was prepared from the product of preparation 118 and 4,6-dichloro-5-methylpyrimidine, using the same method as that described for example 55, in 100% yield.

LRMS APCI m/z 418 [M+H]⁺

EXAMPLES 173 TO 177

The following compounds, of the general formula shown below, were prepared using the same method to that described for example 139, using the product of preparation 110 with commercially available phenols.

132

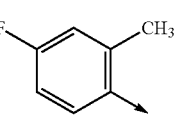

| No. | R¹ | Data (LRMS) | Yield |
|---|---|---|---|
| 173 | 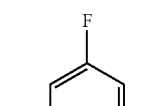 | APCI m/z 384 [M + H]⁺ | 12% |
| 174 | 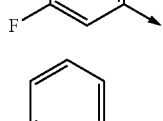 | APCI m/z 384 [M + H]⁺ | 94% |
| 175 | 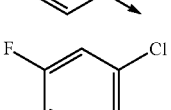 | APCI m/z 388 [M + H]⁺ | 10% |
| 176 | 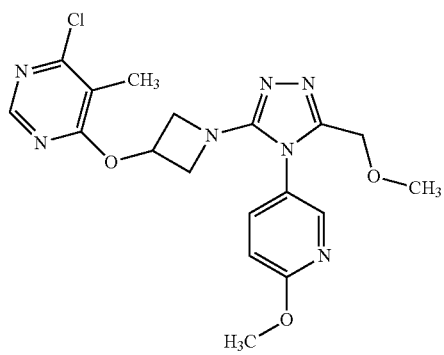 | APCI m/z 352 [M + H]⁺ | 10% |
| 177 | 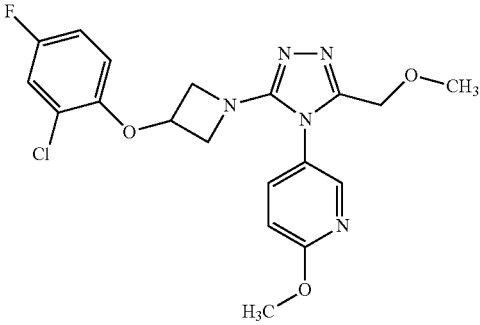 | APCI m/z 404 [M + H]⁺ | 20% |

EXAMPLE 178: 5-{3-[3-(2-CHLORO-4-FLUORO-PHENOXY)-AZETIDIN-1-YL]-5-METHOXYM-ETHYL-[1,2,4]TRIAZOL-4-YL}-PYRIDIN-2-OL

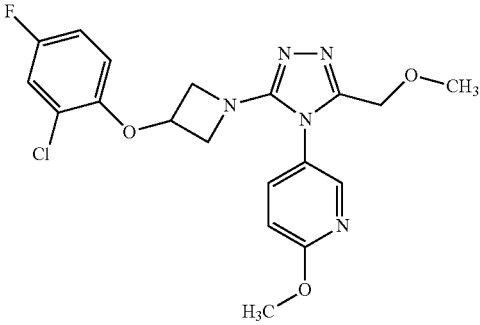 [SMILES: COCc1nnc(N2CC(Oc3ccc(F)cc3Cl)C2)n1-c1ccc(OC)nc1]

Trimethylsilyl iodide (86 µL, 0.29 mmol) was added to a solution of the product of example 25 (100 mg, 0.24 mmol) in acetonitrile (5 mL) at room temperature. The reaction mixture was then heated at 70° C. for 18 hrs then cooled to room temperature. The reaction mixture was diluted with EtOAc (20 mL) then washed with 2N (aq) HCl (10 mL) and brine. Purification of the residue by column chromatography on silica gel, eluting with dichloromethane:methanol, 100:0 to 95:5 then neat MeOH then dichloromethane:methanol: NH₃ 100:10:1, afforded the title compound in 15% yield, 15 mg. ¹H NMR (400 MHz, CDCl₃) δ: 3.35 (s, 3H), 4.10-4.20 (m, 2H), 4.30-4.40 (m, 4H), 4.95-5.00 (m, 1H), 6.50-6.60 (m, 1H), 6.70-6.75 (m, 1H), 6.85-6.95 (m, 1H), 7.10-7.20 (m, 1H), 7.50-7.55 (m, 1H), 7.65-7.80 (m, 1H), 8.10-8.15 (s, 1H); APCI m/z 406 [M+H]⁺

The invention claimed is:
1. A compound of formula (I):

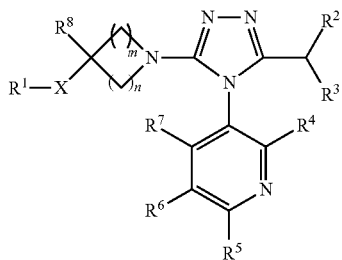

wherein:
m is 2 and n is 2;
X is selected from O, NH, N($C_1$-$C_6$)alkyl, NC(O)($C_1$-$C_6$)alkyl, N(SO₂($C_1$-$C_6$)alkyl), S and SO₂;
R¹ is a 5 to 6 membered aromatic heterocyclic ring containing 1 to 3 hetero atoms independently selected from N, O and S and N-oxides thereof
which is optionally substituted with one or more substituents independently selected from halo, ($C_1$-$C_6$)alkyl, ($C_1$-$C_6$)alkoxy, ($C_1$-$C_6$)alkoxy($C_1$-$C_6$)alkyl, cyano, CF₃, NH($C_1$-$C_6$)alkyl, N(($C_1$-$C_6$)alkyl)₂, CO($C_1$-$C_6$)alkyl, C(O)O($C_1$-$C_6$)alkyl, C(O)NH($C_1$-$C_6$)alkyl, C(O)N(($C_1$-$C_6$)alkyl)₂, C(O)OH and C(O)NH₂;
R² is selected from:
(i) H and hydroxy;
(ii) ($C_1$-$C_6$)alkyl, which is optionally substituted by O($C_1$-$C_6$)alkyl or phenyl;
(iii) O($C_1$-$C_6$)alkyl, which is optionally substituted by O($C_1$-$C_6$)alkyl;
(iv) NH($C_1$-$C_6$)alkyl, said alkyl group being optionally substituted by O($C_1$-$C_6$)alkyl;
(v) N(($C_1$-$C_6$)alkyl)₂, one or both of said alkyl groups being optionally substituted by O($C_1$-$C_6$)alkyl;
(vi) a 5 to 8 membered N-linked saturated or partially saturated heterocycle containing 1 to 3 heteroatoms, each independently selected from N, O and S, wherein at least one heteroatom is N and said ring may optionally incorporate one or two carbonyl groups; said ring being optionally substituted with one or more groups selected from CN, halo, ($C_1$-$C_6$)alkyl, O($C_1$-$C_6$)alkyl, NH($C_1$-$C_6$)alkyl, N(($C_1$-$C_6$)alkyl)₂, C(O)($C_1$-$C_6$)alkyl, C(O)O($C_1$-$C_6$)alkyl, C(O)NH($C_1$-$C_6$)alkyl, C(O)N(($C_1$-$C_6$)alkyl)₂, C(O)OH, C(O)NH₂ and C(O)OCH₂Ph; and
(vii) a 5 to 7 membered N-linked aromatic heterocycle containing 1 to 3 heteroatoms each independently selected from N, O and S, wherein at least one heteroatom is N; said ring being optionally substituted with one or more groups selected from CN, halo, ($C_1$-$C_6$)alkyl, O($C_1$-$C_6$)alkyl, NH($C_1$-$C_6$)alkyl, N(($C_1$-$C_6$)alkyl)₂, C(O)($C_1$-$C_6$)alkyl, C(O)O($C_1$-$C_6$)alkyl, C(O)NH($C_1$-$C_6$)alkyl, C(O)N(($C_1$-$C_6$)alkyl)₂, C(O)OH, C(O)NH₂ and C(O)OCH₂Ph;

R³ is selected from H, ($C_1$-$C_6$)alkyl and ($C_1$-$C_6$)alkoxy($C_1$-$C_6$)alkyl;
R⁴, R⁵, R⁶ and R⁷ are each independently selected from H, halo, hydroxy, CN, ($C_1$-$C_6$)alkyl, NH($C_1$-$C_6$)alkyl, N(($C_1$-$C_6$)alkyl)₂ and O($C_1$-$C_6$)alkyl;
R⁸ is selected from H, ($C_1$-$C_6$)alkyl, ($C_1$-$C_6$)alkoxy($C_1$-$C_6$)alkyl, CH₂OH, CH₂NH₂, CH₂NH($C_1$-$C_6$)alkyl, CH₂N(($C_1$-$C_6$)alkyl)₂, CN, C(O)NH₂, C(O)NH($C_1$-$C_6$)alkyl and C(O)N(($C_1$-$C_6$)alkyl)₂;
a tautomer thereof or a pharmaceutically acceptable salt of said compound or tautomer.

2. A compound according to claim 1 wherein X is selected from O, NH, N($C_1$-$C_3$)alkyl, and N(SO₂($C_1$-$C_3$)alkyl); or a pharmaceutically acceptable salt thereof.

3. A compound according to claim 2 wherein X is O or NCH₃; or a pharmaceutically acceptable salt thereof.

4. A compound according to claim 1 wherein R¹ is a 5 to 6 membered aromatic heterocyclic ring containing 1 to 3 nitrogen atoms which is optionally substituted with one or more substituents independently selected from halo, ($C_1$-$C_6$)alkyl, ($C_1$-$C_6$)alkoxy, ($C_1$-$C_6$)alkoxy($C_1$-$C_6$)alkyl, cyano, CF₃, N(($C_1$-$C_6$)alkyl)₂, C(O)N(($C_1$-$C_6$)alkyl)₂, and C(O)NH₂; or a pharmaceutically acceptable salt thereof.

5. A compound according to claim 4 wherein R¹ is selected from pyridinyl, pyrimidinyl, pyridazinyl, pyrazinyl, pyrazolyl and 2-pyridonyl, each of which is optionally substituted with one or more substituents independently selected from halo, ($C_1$-$C_6$)alkyl, ($C_1$-$C_6$)alkoxy, ($C_1$-$C_6$)alkoxy($C_1$-$C_6$)alkyl, cyano, CF₃, N(($C_1$-$C_6$)alkyl)₂, C(O)N(($C_1$-$C_6$)alkyl)₂, and C(O)NH₂; or a pharmaceutically acceptable salt thereof.

6. A compound according to claim 5 wherein R¹ is selected from pyridinyl, pyrimidinyl, pyridazinyl, pyrazinyl, pyrazolyl and 2-pyridonyl, each of which is optionally substituted with one to three substituents independently selected from chloro, fluoro, methyl, ethyl, isopropyl, methoxy, cyano, CF₃, N(CH₃)₂, C(O)N(CH₃)₂, and C(O)NH₂; or a pharmaceutically acceptable salt thereof.

7. A compound according to claim 1 wherein X is selected from O, NH, N($C_1$-$C_3$)alkyl, and N(SO₂($C_1$-$C_3$)alkyl); or a pharmaceutically acceptable salt thereof.

8. A compound according to claim 7 wherein X is O or NCH₃; or a pharmaceutically acceptable salt thereof.

9. A compound according to claim 8 wherein R¹ is selected from pyridinyl, pyrimidinyl, pyridazinyl, pyrazinyl, pyrazolyl and 2-pyridonyl, each of which is optionally substituted with one to three substituents independently selected from chloro, fluoro, methyl, ethyl, isopropyl, methoxy, cyano, CF₃, N(CH₃)₂, C(O)N(CH₃)₂, and C(O)NH₂; or a pharmaceutically acceptable salt thereof.

10. A compound according to claim 9 wherein R² is selected from:
(i) H or hydroxy;
(ii) ($C_1$-$C_3$)alkyl, which is optionally substituted by O($C_1$-$C_3$)alkyl;
(iii) O($C_1$-$C_3$)alkyl, which is optionally substituted by O($C_1$-$C_3$)alkyl;
(iv) NH($C_1$-$C_3$)alkyl, said alkyl group being optionally substituted by O($C_1$-$C_3$)alkyl;
(v) N(($C_1$-$C_3$)alkyl)₂, one or both of said alkyl groups being optionally substituted by O($C_1$-$C_3$)alkyl;
(vi) a 5 to 6 membered N-linked saturated heterocycle containing 1 to 2 nitrogen atoms; said ring may optionally incorporate one or two carbonyl groups; said ring being optionally substituted by C(O)NH₂ or C(O)OCH₂Ph; and (viii) a 5 to 6 membered N-linked aromatic heterocycle containing 1 to 3 heteroatoms each independently selected from N, O and S, wherein at least one heteroatom is N;

or a pharmaceutically acceptable salt thereof.

11. A compound according to claim 10 wherein $R^2$ is selected from:

(i) H or hydroxy;

(ii) $(C_1\text{-}C_3)$alkyl, which is optionally substituted by $O(C_1\text{-}C_3)$alkyl; and (iii) $O(C_1\text{-}C_3)$alkyl, which is optionally substituted by $O(C_1\text{-}C_3)$alkyl;

or a pharmaceutically acceptable salt thereof.

12. A compound according to claim 11 wherein $R^3$ is H or $(C_1\text{-}C_3)$alkyl; or a pharmaceutically acceptable salt thereof.

13. A compound according to claim 12 wherein $R^4$, $R^5$, $R^6$ and $R^7$ are each independently selected from H, halo, hydroxy, $(C_1\text{-}C_3)$alkyl and $O(C_1\text{-}C_3)$alkyl; or a pharmaceutically acceptable salt thereof.

14. A compound according to claim 13 wherein $R^8$ is selected from H, methyl, ethyl, methoxymethyl, methoxyethyl and CN; or a pharmaceutically acceptable salt thereof.

15. A compound according to claim 1 wherein $R^2$ is selected from:

(i) H or hydroxy;

(ii) $(C_1\text{-}C_3)$alkyl, which is optionally substituted by $O(C_1\text{-}C_3)$alkyl;

(iii) $O(C_1\text{-}C_3)$alkyl, which is optionally substituted by $O(C_1\text{-}C_3)$alkyl;

(iv) $NH(C_1\text{-}C_3)$alkyl, said alkyl group being optionally substituted by $O(C_1\text{-}C_3)$alkyl;

(v) $N((C_1\text{-}C_3)$alkyl$)_2$, one or both of said alkyl groups being optionally substituted by $O(C_1\text{-}C_3)$alkyl;

(vi) a 5 to 6 membered N-linked saturated heterocycle containing 1 to 2 nitrogen atoms; said ring may optionally incorporate one or two carbonyl groups; said ring being optionally substituted by $C(O)NH_2$ or $C(O)OCH_2Ph$; and (vii) a 5 to 6 membered N-linked aromatic heterocycle containing 1 to 3 heteroatoms each independently selected from N, O and S, wherein at least one heteroatom is N;

or a pharmaceutically acceptable salt thereof.

16. A compound according to claim 15 wherein $R^2$ is selected from:

(i) H or hydroxy;

(ii) $(C_1\text{-}C_3)$alkyl, which is optionally substituted by $O(C_1\text{-}C_3)$alkyl; and (iii) $O(C_1\text{-}C_3)$alkyl, which is optionally substituted by $O(C_1\text{-}C_3)$alkyl;

or a pharmaceutically acceptable salt thereof.

17. A compound according to claim 16 wherein $R^2$ is selected from H, hydroxy, methyl, methoxy and ethoxy; or a pharmaceutically acceptable salt thereof.

18. A compound according to claim 1 wherein $R^3$ is H or $(C_1\text{-}C_3)$alkyl; or a pharmaceutically acceptable salt thereof.

19. A compound according to claim 18 wherein $R^3$ is H or $CH_3$; or a pharmaceutically acceptable salt thereof.

20. A compound according to claim 1 wherein $R^4$, $R^5$, $R^6$ and $R^7$ are each independently selected from H, halo, hydroxy, $(C_1\text{-}C_3)$alkyl and $O(C_1\text{-}C_3)$alkyl; or a pharmaceutically acceptable salt thereof.

21. A compound according to claim 20 wherein $R^4$ is H or methyl; $R^5$ is hydroxy or methoxy; and $R^6$ and $R^7$ are both H; or a pharmaceutically acceptable salt thereof.

22. A compound according to claim 1 wherein $R^8$ is selected from H, methyl, ethyl, isopropyl, methoxymethyl, methoxyethyl, $CH_2OH$, $CH_2NH_2$, $CH_2NHCH_3$, $CH_2N(CH_3)_2$, CN, $C(O)NH_2$, $C(O)NHCH_3$, and $C(O)N(CH_3)_2$; or a pharmaceutically acceptable salt thereof.

23. A compound according to claim 22 wherein $R^8$ is selected from H, methyl, ethyl, methoxymethyl, methoxyethyl and CN; or a pharmaceutically acceptable salt thereof.

24. A compound which is 2-methoxy-5-(3-(methoxymethyl)-5-{4-[(3-methylpyridin-4-yl)oxy]piperidin-1-yl}-4H-1,2,4-triazol-4-yl)pyridine; tautomers thereof; and pharmaceutically acceptable salts of said compounds or tautomers.

25. A compound of formula (I):

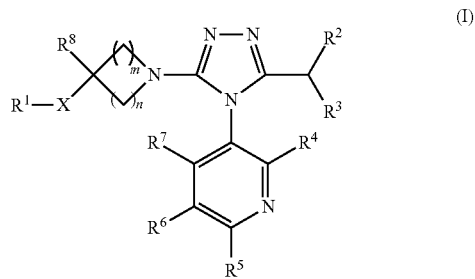

wherein:

m is 2 and n is 2;

X is selected from O and $N(C_1\text{-}C_6)$alkyl;

$R^1$ is a 5 to 6 membered aromatic heterocyclic ring containing 1 to 3 nitrogen atoms which is optionally substituted with one or more substituents independently selected from halo, $(C_1\text{-}C_6)$alkyl, $(C_1\text{-}C_6)$alkoxy, $(C_1\text{-}C_6)$alkoxy$(C_1\text{-}C_6)$alkyl, cyano, $CF_3$, $C(O)N((C_1\text{-}C_6)$alkyl$)_2$ and $C(O)NH_2$;

$R^2$ is selected from H, hydroxyl, $(C_1\text{-}C_6)$alkyl and $O(C_1\text{-}C_6)$alkyl;

$R^3$ is selected from H and $(C_1\text{-}C_6)$alkyl;

$R^4$, $R^5$, $R^6$ and $R^7$ are each independently selected from H, $(C_1\text{-}C_6)$alkyl and $O(C_1\text{-}C_6)$alkyl;

$R^8$ is selected from H and $(C_1\text{-}C_6)$alkyl;

a tautomer thereof or a pharmaceutically acceptable salt of said compound or tautomer.

26. A pharmaceutical composition comprising a compound of formula (I) according to claim 1 or a pharmaceutically acceptable salt thereof, and a pharmaceutically acceptable diluent or carrier.

27. A method of treating hypoactive sexual desire disorder, sexual arousal disorder, orgasmic disorder, sexual pain disorder, premature ejaculation, preterm labour, complications in labour, appetite and feeding disorders, benign prostatic hyperplasia, premature birth, dysmenorrhoea, congestive heart failure, arterial hypertension, liver cirrhosis, nephrotic hypertension, ocular hypertension, obsessive compulsive disorder or neuropsychiatric disorders in a mammal, the method comprising administering to said mammal a therapeutically effective amount of a compound of formula (I) according to claim 1 or a pharmaceutically acceptable salt thereof.

28. The method according to claim 27 wherein the disorder or condition is selected from sexual arousal disorder, orgasmic disorder, sexual pain disorder and premature ejaculation.

\* \* \* \* \*